US010181010B2

(12) United States Patent
Patel et al.

(10) Patent No.: US 10,181,010 B2
(45) Date of Patent: Jan. 15, 2019

(54) SYSTEM FOR GENETIC SURVEILLANCE AND ANALYSIS

(71) Applicant: APPLIED BIOSYSTEMS, LLC, Carlsbad, CA (US)

(72) Inventors: Chirag Patel, Atherton, CA (US); Hans Fuernkranz, Saratoga, CA (US); Michael Greenstein, Los Altos, CA (US)

(73) Assignee: APPLIED BIOSYSTEMS, LLC, Carlsbad, CA (US)

(*) Notice: Subject to any disclaimer, the term of this patent is extended or adjusted under 35 U.S.C. 154(b) by 748 days.

(21) Appl. No.: 14/566,651

(22) Filed: Dec. 10, 2014

(65) Prior Publication Data
US 2015/0213192 A1 Jul. 30, 2015

Related U.S. Application Data

(63) Continuation of application No. 13/611,289, filed on Sep. 12, 2012, which is a continuation of application No. 12/868,704, filed on Aug. 25, 2010, now abandoned, which is a continuation of application No. 11/412,030, filed on Apr. 26, 2006, now abandoned.

(60) Provisional application No. 60/749,003, filed on Dec. 9, 2005, provisional application No. 60/699,950, filed on Jul. 15, 2005, provisional application No. 60/696,157, filed on Jun. 30, 2005, provisional application No. 60/674,876, filed on Apr. 26, 2005, provisional application No. 60/674,750, filed on Apr. 26, 2005.

(51) Int. Cl.
| G06F 19/00 | (2018.01) |
| G06F 19/20 | (2011.01) |
| G06F 19/22 | (2011.01) |
| G06F 19/28 | (2011.01) |
| G16H 10/40 | (2018.01) |
| G16H 50/80 | (2018.01) |

(52) U.S. Cl.
CPC .............. *G06F 19/22* (2013.01); *G06F 19/00* (2013.01); *G06F 19/28* (2013.01); *G16H 50/80* (2018.01); *G06F 19/20* (2013.01); *G16H 10/40* (2018.01); *Y02A 90/24* (2018.01); *Y02A 90/26* (2018.01)

(58) Field of Classification Search
None
See application file for complete search history.

(56) References Cited

U.S. PATENT DOCUMENTS

| 4,859,421 A | 8/1989 | Apicella |
| 5,473,732 A | 12/1995 | Chang |
| 5,868,669 A | 2/1999 | Iliff |
| 5,873,990 A | 2/1999 | Wojciechoswki et al. |
| 5,874,046 A | 2/1999 | Megerle |
| 6,085,576 A | 7/2000 | Sunshine et al. |
| 6,185,561 B1 | 2/2001 | Balaban et al. |
| 6,234,006 B1 | 5/2001 | Sunshine et al. |
| 6,303,297 B1 | 10/2001 | Lincoln et al. |
| 6,364,834 B1 | 4/2002 | Reuss et al. |
| 6,418,783 B2 | 7/2002 | Sunshine et al. |
| 6,422,061 B1 | 7/2002 | Sunshine |
| 6,482,156 B2 | 11/2002 | Iliff |
| 6,490,530 B1 | 12/2002 | Wyatt |
| 6,532,462 B2 | 3/2003 | Balaban |
| 6,567,540 B2 | 5/2003 | Balaban et al. |
| 6,576,459 B2 | 6/2003 | Miles et al. |
| 6,658,915 B2 | 12/2003 | Sunshine et al. |
| 6,687,692 B1 | 2/2004 | Balaban et al. |
| 6,699,713 B2 | 3/2004 | Benett et al. |
| 6,714,925 B1 | 3/2004 | Barnhill et al. |
| 6,757,714 B1 | 6/2004 | Hansen |
| 6,826,296 B2 | 11/2004 | Balaban et al. |
| 6,855,554 B2 | 2/2005 | Fritsche et al. |
| 6,878,755 B2 | 4/2005 | Singh et al. |
| 6,889,165 B2 | 5/2005 | Lind et al. |
| 6,905,816 B2 | 6/2005 | Jacobs et al. |
| 6,990,501 B2 | 1/2006 | Beals |
| 7,005,982 B1 | 2/2006 | Frank |
| 7,035,740 B2 | 4/2006 | Kermani |
| 7,062,076 B1 | 6/2006 | Osborne et al. |
| 7,251,642 B1 | 7/2007 | Szeto |
| 7,329,493 B2 | 2/2008 | Chou et al. |
| 2001/0027389 A1 | 10/2001 | Beverina |
| 2001/0029322 A1 | 10/2001 | Iliff |

(Continued)

FOREIGN PATENT DOCUMENTS

WO 2006/116455 11/2006

OTHER PUBLICATIONS

Sebban et al. A data-minimg approach to spacer oligonucleotide typing of *Mycobacterium* tuberculosis Bioinformatics vol. 18, pp. 235-243 (2002).*

(Continued)

*Primary Examiner* — John S Brusca

(57) ABSTRACT

A genetic surveillance system comprises a communications network and at least one reader-analyzer instrument. The reader-analyzer instrument has a communication interface to communicate over the network. The reader-analyzer instrument is adapted to perform genetic assay analysis of a sample obtained from a member of a population and to generate detection-related data based upon the analysis. The reader-analyzer instrument is adapted to associate qualifying information with the detection-related data and to communicate the associated qualifying information and detection-related data over the network.

17 Claims, 17 Drawing Sheets

(56) References Cited

U.S. PATENT DOCUMENTS

| | | |
|---|---|---|
| 2001/0039824 A1 | 11/2001 | Sunshine |
| 2002/0059030 A1 | 5/2002 | Otworth |
| 2002/0086289 A1* | 7/2002 | Straus ............... C12Q 1/6827 435/6.18 |
| 2002/0095073 A1 | 7/2002 | Jacobs |
| 2002/0123048 A1 | 9/2002 | Sunshine |
| 2002/0124631 A1 | 9/2002 | Sunshine |
| 2002/0137196 A1 | 9/2002 | Miles |
| 2002/0152037 A1 | 10/2002 | Sunshine |
| 2002/0178789 A1 | 12/2002 | Sunshine |
| 2002/0191826 A1 | 12/2002 | Benett |
| 2003/0003441 A1 | 1/2003 | Colston |
| 2003/0023189 A1 | 1/2003 | Kuo |
| 2003/0027244 A1 | 2/2003 | Colston |
| 2003/0064526 A1 | 4/2003 | Niedbala |
| 2003/0069002 A1 | 4/2003 | Hunter |
| 2003/0073931 A1 | 4/2003 | Boecker |
| 2003/0093187 A1 | 5/2003 | Walker |
| 2003/0125998 A1 | 7/2003 | McKenney |
| 2003/0135095 A1 | 7/2003 | Iliff |
| 2003/0153021 A1 | 8/2003 | Lu |
| 2003/0163299 A1 | 8/2003 | Iliff |
| 2003/0163351 A1 | 8/2003 | Brown et al. |
| 2003/0175993 A1 | 9/2003 | Toranto |
| 2003/0186218 A1 | 10/2003 | Singh |
| 2003/0216869 A1 | 11/2003 | Sunshine |
| 2004/0030586 A1 | 2/2004 | Cucchiara |
| 2004/0033501 A1 | 2/2004 | Lappe |
| 2004/0038385 A1 | 2/2004 | Langlois et al. |
| 2004/0053290 A1 | 3/2004 | Terbrueggen et al. |
| 2004/0069046 A1 | 4/2004 | Sunshine |
| 2004/0072263 A1 | 4/2004 | Link |
| 2004/0073459 A1 | 4/2004 | Barthell |
| 2004/0078146 A1 | 4/2004 | Lombardo |
| 2004/0078219 A1* | 4/2004 | Kaylor ............... G06Q 50/22 705/2 |
| 2004/0089616 A1 | 5/2004 | Kellogg |
| 2004/0100376 A1 | 5/2004 | Lye |
| 2004/0106164 A1 | 6/2004 | Brown |
| 2004/0132220 A1 | 7/2004 | Fish |
| 2004/0135684 A1 | 7/2004 | Steinthal |
| 2004/0161370 A1 | 8/2004 | Sunshine et al. |
| 2004/0181346 A1 | 9/2004 | Sunshine et al. |
| 2004/0204915 A1 | 10/2004 | Steinthal et al. |
| 2004/0219517 A1 | 11/2004 | Ecker et al. |
| 2004/0236604 A1 | 11/2004 | McNair |
| 2004/0260204 A1 | 12/2004 | Boecker et al. |
| 2005/0043894 A1 | 2/2005 | Fernandez |
| 2005/0053950 A1 | 3/2005 | Ubani et al. |
| 2005/0059105 A1 | 3/2005 | Alocilja et al. |
| 2005/0060599 A1 | 3/2005 | Inami et al. |
| 2005/0061056 A1 | 3/2005 | Sunshin et al. |
| 2005/0085257 A1 | 4/2005 | Laird et al. |
| 2005/0101841 A9 | 5/2005 | Kaylor et al. |
| 2005/0112557 A1 | 5/2005 | Liu et al. |
| 2005/0123563 A1 | 6/2005 | Doranz et al. |
| 2005/0148090 A1 | 7/2005 | Knezevic et al. |
| 2005/0159922 A1 | 7/2005 | Hsiung et al. |
| 2005/0161669 A1 | 7/2005 | Jovanovich et al. |
| 2011/0070587 A1 | 3/2011 | Fuernkranz et al. |

OTHER PUBLICATIONS

Liu et al. Self-Contained, Fully Integrated Biochip for Sample Preparation, Polymerase Chain Reaction Amplification, and DNA Microarray Detection Analytical Chemistry vol. 76, pp. 1824-1831 (2004).*

Templeton et al. Evaluation of Real-Time PCR for Detection of and Discrimination between Bordetella pertussis, Bordetella parapertussis, and Bordetella holmesii for Clinical Diagnosis Journal of Clinical Microbiology vol. 41, pp. 4121-4126 (2003).*

Higgins et al. A handheld real time thermal cycler for bacterial pathogen detection Biosensors and Bioelectronics vol. 18, pp. 1115-1123 (Year: 2003).*

Robertson et al. Identification and interrogation of highly informative single nucleotide polymorphism sets defined by bacterial multilocus sequence typing databases Journal of Medical Microbiology vol. 53, pp. 35-45 (Year: 2004).*

Mariella, "LLNL Center for Microtechnology: Capabilities, customers, case study—HANAA (Handheld Nucleic Acid Analyzer)", *Proceedings of SPIE*, vol. 5001, 22-33.

PCT/US2006/015732, "International Preliminary Report on Patentability dated", Mar. 17, 2009, 1-5.

PCT/US2006/015732, "International Search Report and Written Opinion dated", Aug. 4, 2008, 1-6.

* cited by examiner

SYSTEM FOR GENETIC SURVEILLANCE AND ANALYSIS

CROSS-REFERENCE TO RELATED APPLICATIONS

This application is a continuation of U.S. application Ser. No. 13/611,289, filed Sep. 12, 2012, now abandoned, which is a continuation of U.S. application Ser. No. 12/868,704, filed Aug. 25, 2010, now abandoned, which is a continuation of U.S. application Ser. No. 11/412,030, filed Apr. 26, 2006, now abandoned, which claims the benefit of U.S. Provisional Application No. 60/674,750, filed Apr. 26, 2005; U.S. Provisional Application No. 60/699,950, filed Jul. 7, 2005; U.S. Provisional Application No. 60/749,003, filed Dec. 9, 2005; U.S. Provisional Application No. 60/674,876, filed Apr. 26, 2005; and U.S. Provisional Application No. 60/696,157, filed Jun. 30, 2005. The disclosures of the above applications are incorporated herein by reference.

All literature and similar materials cited in this application, including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

INTRODUCTION

Currently, improved emergency preparedness and response to bioterrorism, pathogenic epidemics, and other such public health emergencies have become of great concern to governments, public health organizations, and the public at large. Governments, public health institutions, and other such laboratories are in need of tools to aid in building networks for determining threats to the public. Such entities are also in need of rapid, automated and bidirectional communications and analysis methods to identify threats and their spatial and temporal patterns for timely efficient response and preventative measures.

DRAWINGS

The skilled artisan will understand that the drawings, described below, are for illustration purposes only. The drawings are not intended to limit the scope of the present teachings in any way.

DESCRIPTION OF VARIOUS EMBODIMENTS

While the present teachings are described in conjunction with various embodiments, it is not intended that the present teachings be limited to such embodiments. On the contrary, the present teachings encompass various alternatives, modifications, and equivalents, as will be appreciated by those of skill in the art. In the event that one or more of the incorporated references differs from or contradicts this application, including, but not limited to, defined terms, term usage, described techniques, or the like, this application controls.

Figure 1:
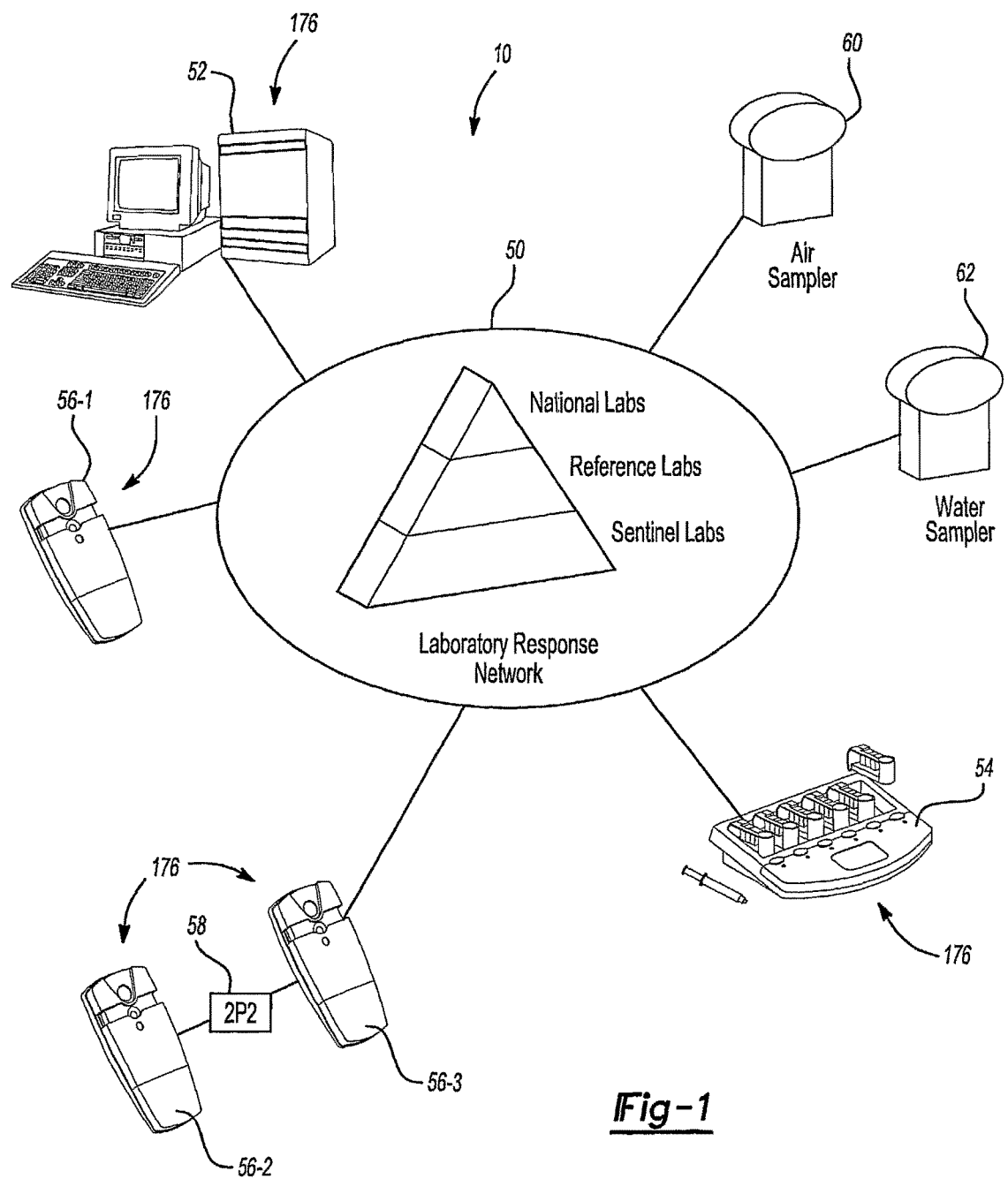
FIG. 1 is a high level system diagram illustrating a genetic surveillance and analysis system working in conjunction with a laboratory response network.

In various embodiments, a genetic surveillance and analysis system 10 shown in FIG. 1 illustrates the system 10 working in conjunction with a laboratory response network 50. The laboratory response network 50 has been illustrated as a three-tiered, pyramidal, hierarchical arrangement of laboratories. However, the genetic surveillance and analysis system 10 is not limited to operating only with networks configured in this fashion. The hierarchical pyramid relationship is illustrated to provide a better understanding of how a genetic surveillance and analysis system 10, according to the present teachings, might be integrated with a contemporary laboratory response network 50, such as that promulgated by the U.S. Department of Health and Human Services' (HHS) Centers for Disease Control and Prevention (CDC).

For example, in 1999, the CDC established a Laboratory Response Network (LRN) 50. The LRN's purpose is to coordinate a network of laboratories that can respond to biological and chemical terrorism. The LRN 50 has grown since it was first established, and now includes a wide variety of different types of laboratories, such as state and local public health laboratories, veterinary laboratories, military laboratories, and international laboratories.

The participating laboratories are designated as either national, reference, or sentinel, depending on each individual laboratory's function within the LRN 50. Sentinel labs, at the broad base of the pyramid, represent the thousands of hospital- and clinic-based labs that have direct contact with patients. In an unannounced or covert terrorist attack, specimens provided by patients during routine care might indicate the onset of a bioterrorist attack. Similarly, specimens from patients visiting hospitals and clinics may signal the spread of a disease. Sentinel labs are thus often the first facility to spot a suspicious specimen. The sentinel lab's responsibility is to refer that specimen to the proper reference lab.

Reference labs, also referred to as confirmatory reference labs, are equipped to perform tests to detect and confirm the presence of a threat agent (including those related to bioterrorism and epidemics). These labs ensure a timely local response in the event of a terrorist incident or epidemic. Rather than having to rely on confirmation from national labs at the CDC, reference labs are capable of producing conclusive results upon which public health authorities are able to act. In some cases, unique abilities may be required, such as handling a highly infectious agent or identifying and analyzing specific agent strains. This is the function of the national laboratories, which are positioned at the narrow top of the pyramid.

The named laboratory response network 50 might suggest that an integrated computer network joins the participating laboratories. Although computer networks and telecommunication networks, such as the Internet and the public telephone infrastructure, are utilized, there is currently no unified, dedicated computer network for the collection and analysis of aggregated genetic data. The genetic surveillance and analysis system 10 can serve this function, linking together participating members of the LRN and may also link other public health, safety, and military organizations, which may have their own separate computer networks.

In various embodiments, the genetic surveillance and analysis system 10 may be a population security and epidemiological analysis system. In various embodiments, epidemiology can be the study of the distribution and determinants of disease frequency in human populations. This can include two main areas of investigation, one, the study of distribution and disease and two, the search for the determinants (causes of the disease and its distribution). The first area can include describing the distribution of health status in terms of age, gender, race, geography, time, weather conditions, and other demographics. The second area can involve an explanation of the patterns into the disease distribution in the terms of causal factors.

Epidemiology can include the search for concordance between known and suspected cause of a disease, and known patterns of distribution of disease, or use of these patterns to postulate elements of the environment that should be investigated for possible causal roles. An excessive frequency, or even the mere occurrence of biological contaminants in environmental or biological samples, may be a feature of many infectious and non-infectious diseases, as well as diseases known to be associated with microorganisms or pathogens. Identifying the frequency of a particular disease as being excessive may be developed by following its frequency over time, by comparing its frequency in different places, or by comparing its frequencies among subgroups in a single population at a particular time. Such identification may include identifying the excessive frequency that comes about in a short period of time and in a narrowly defined geographic area. Other terms that may relate to excessive frequency include epidemic, pandemic, incidence, and prevalence. In addition to frequency, mere occurrence of biological contaminants in environmental or biological samples may also be of concern.

The genetic surveillance and analysis system 10 can utilize genetic assay technology capable of detecting and analyzing a variety of different strains of bacteria, viruses, and pathogens. As will be more fully explained below, genetic assay technology can be deployed using an assortment of different types of reader-analyzer instruments 176 that can be adapted for bidirectional communication through an integrating software platform named EpiMonitor.

The system 10 supports a plurality of reader-analyzer instruments 176 of different sizes and capabilities, including those ranging from sophisticated laboratory instruments 52 to portable multi-cartridge units (a portable instrument 54) to small, shirt-pocket-sized units such as handheld instruments 56-1, 56-2, and 56-3. The reader-analyzer instruments 176 analyze samples, whether taken from a patient or from the environment, and have varying processing ability to process the results. In various embodiments, at least some of the reader-analyzer instruments 176 are capable of peer-to-peer (P2P) interaction with one another, as illustrated diagrammatically at 58 between handheld instruments 56-2 and 56-3. In various embodiments, at the base of the pyramid, sentinel laboratories may employ primarily handheld 56 and portable instruments 54 and, as such, these instruments may be present in numbers on the order of thousands to tens of thousands to accommodate the large number of sentinel laboratories. In various embodiments, the next layer of the pyramid, reference laboratories, may employ portable instruments 54 and more powerful laboratory instruments 52 and, as such, hundreds or thousands of these instruments may be present. In various embodiments, national laboratories may employ hundreds of laboratory instruments 52.

In various embodiments, the laboratory instrument 52 can be implemented using any one of a variety of different reader-analyzer instruments 176, such as genetic assay analysis platforms. Suitable platforms include the model 7500 fast real-time PCR system and the 7900 HT fast real-time PCR system, both available from Applied Biosystems, Foster City, Calif. Other genetic assay analysis platforms can also be used such as, for example, PCR instruments commercially available from Bio Rad, Strategene, Roche Applied Science, Techne Quantica, and Cepheid, as well as, PCR instruments that operate using isothermal methods. Still, examples of other genetic analysis platforms that may be useful herein include microarray technology such as those commercially available from Applied Biosystems, Affymetrix, Agilent, Illumina, and Xeotron. Typically, the laboratory instrument 52 would be deployed, for example, in hospital laboratory, at a university, or in a government public health laboratory, which may or may not be a participating member of the laboratory response network.

In various embodiments, a reader-analyzer instrument 176 can be portable instrument 54, which can be physically smaller than the laboratory instrument 52 to make it suitable for deployment in a doctor's office or small clinic. It can be connected to a computer, eliminating the need for on-board processing. The portable instrument 54 is generally capable of analyzing fewer samples for fewer target sequences than the laboratory instrument 52.

In various embodiments, a reader-analyzer instrument 176 can be a handheld instrument 56 and may represent an economical end of the instrument spectrum. In various embodiments, the handheld instrument 56 may be of convenient, portable size (e.g., approximately the size of a deck of playing cards). It can be configured to detect a specific disease such as multidrug-resistant tuberculosis. The handheld instrument 56 can be capable of analyzing samples obtained in a variety of different forms including sputum samples, blood samples, and the like. The handheld instrument 56 can be battery powered and can include an embedded internal controller so that no external computer is required.

Reader-analyzer instruments 176 that may be used in the system are not limited to such instruments that can perform PCR. Any instrument that can provide data on the analysis of pathogens such as identifying a strain of bacteria, fungi, virus, and the like, may be integrated into the genetic surveillance and analysis system 10. Examples of other such reader-analyzer instruments 176 include mass spectrometers, which may include the use of MADLI, chromatography, pyrolization, and other such techniques for introducing a sample, DNA micro arrays such as, for example, those commercially available from Affymetrix, Agilent, Illumina, Xeotron, and Applied Biosystems, as well as those systems that may be developed in-house by a particular laboratory, and may also include instruments capable of detection using an antibody such as ELISA, and the like.

While the instruments described above are adapted for processing a sample obtained from a human, plant or animal, the genetic surveillance and analysis system 10 can be readily adapted to utilize other types of input devices, such as environmental sensors. Environmental sensors such as, for example, air samplers 60, water samplers 62 for bodies of water (e.g., reservoirs, tanks, lakes, etc.), as well as other sampling configurations, can be readily adapted for use with the present teachings. The environmental samplers 60, 62 can be adapted to analyze samples taken from strategic locations. The results obtained by analyzing those samples can be integrated with the data being collected by reader-analyzer instruments 176 via the EpiMonitor software platform 100, described more fully below.

Figure 2:
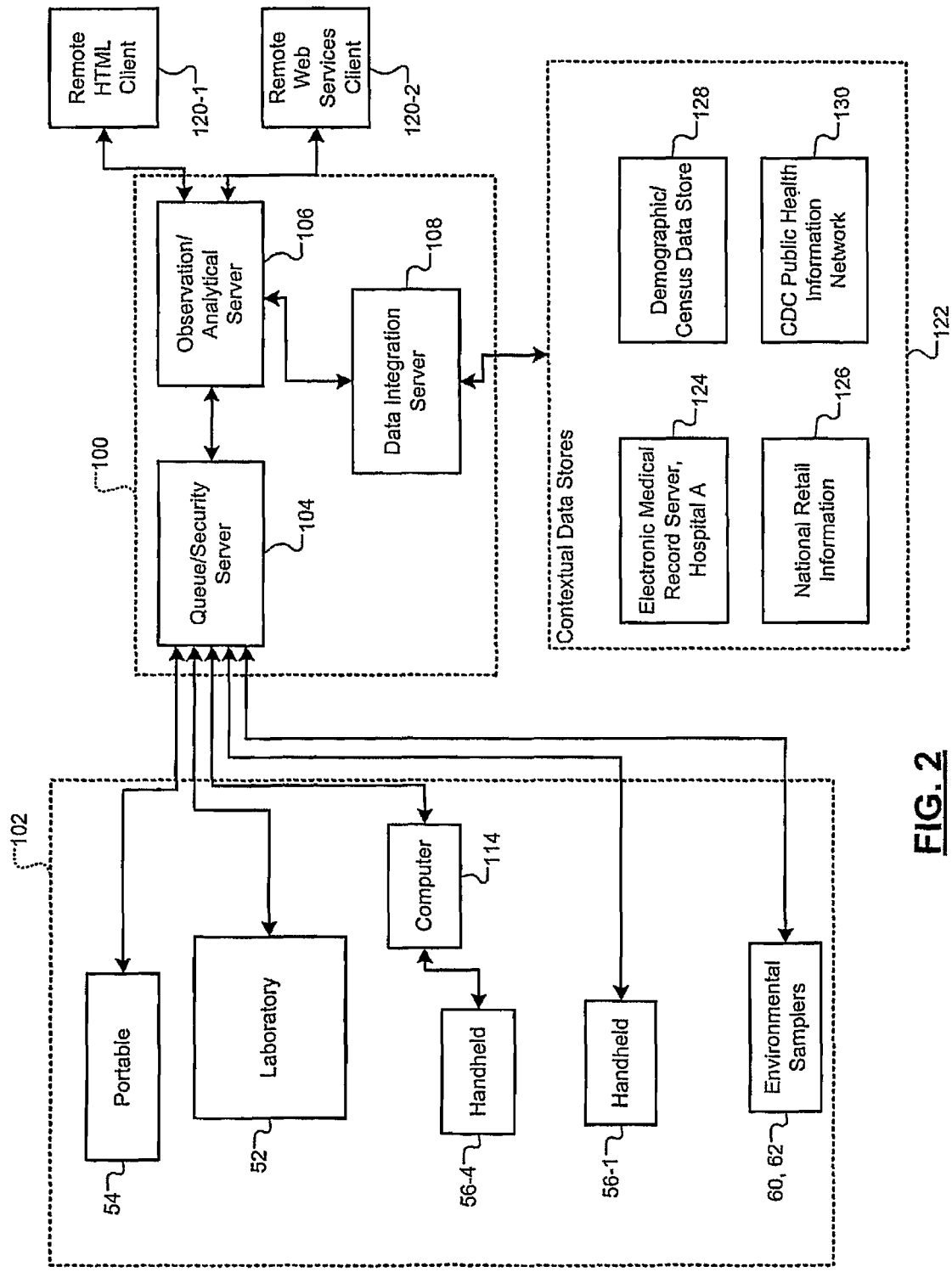
FIG. 2 is a data flow diagram useful in understanding some of the principles of the genetic surveillance and analysis system.

Referring now to FIG. 2, the genetic surveillance and analysis system 10 utilizes an EpiMonitor software platform 100 that integrates various reader-analyzer instruments 176 within a database system. The EpiMonitor software platform 100 organizes and supports bidirectional communication among a collection 102 of reader-analyzer instruments 176, each analyzing samples of genetic data.

The collection 102 provides reaction data and contextual data to a queue/security server 104 of the EpiMonitor software platform 100. In various embodiments, the queue/security server 104 can establish secure connections with the collection 102 of reader-analyzer instruments 176, verify that data has been received uncorrupted, and queue received data for processing. The queue/security server 104 can communicate with the collection 102 of reader-analyzer instruments 176 through a variety of intermediaries, including the public Internet, Virtual Private Networks, and private networks. The queue/security server 104 can also communicate information, such as sample preparation instructions, to the collection 102 of reader-analyzer instruments 176.

The queue/security server 104 provides data to an observation/analytical server 106 of the EpiMonitor software platform 100. In various embodiments, the observation/analytical server 106 can pre-process data, perform rules-based analysis, and discern data trends. Together, the servers 104 and 106 validate, collect, and analyze data, as described in more detail below. The servers 104 and 106 can be implemented as stand-alone servers, as a single unified server, or as a distributed system of multiple servers. In addition, various functions of the servers 104 and 106 can be distributed to the collection 102 of reader-analyzer instruments 176 or to computers associated with any of the collection 102 of reader-analyzer instruments 176.

The collection 102 of reader-analyzer instruments 176 depicted includes a portable instrument 54, a laboratory instrument 52, a handheld instrument 56-1, a handheld instrument 56-4, which communicates with the queue/security server 104 via a stand-alone computer 114, and environmental samplers 60, 62. The observation/analytical server 106 can store reaction and contextual data obtained from the collection 102 of reader-analyzer instruments 176 into a suitable database. The observation/analytical server 106 can provide access to this database via an HTML (hypertext markup language) web interface to a remote client 120-1. A web browser within the remote client 120-1 can display observations and analysis from the observation/analytical server 106. Examples of web browser displays include "Biomarker: ABC, Incidence during January 2003-December 2004: XX, Prevalence during January 2003-December 2004: XY," and "Date/Time: 11/19/2004, 8:00 AM, Region: Northern California, Biomarker: ABC, Current Incidence: XX, Current Prevalence: XY." Access to the database can also be provided programmatically via web services, such as to a second remote client 120-2.

The observation/analytical server 106 can integrate data from sources other than the collection 102 of reader-analyzer instruments 176. To convert external data sources into a standard form that the observation/analytical server 106 can process, the EpiMonitor software platform 100 includes, in various embodiments, a data integration server 108. The data integration server 108 communicates with contextual data stores 122. Contextual data stores 122 can include medical records, such as an electronic medical record server 124 located at hospital A. Contextual data stores 122 can also include national retail information 126, a demographic/census data store 128, such as provided by the U.S. Census Bureau, and a data store 130 of the CDC Public Health Information Network.

Figure 3:
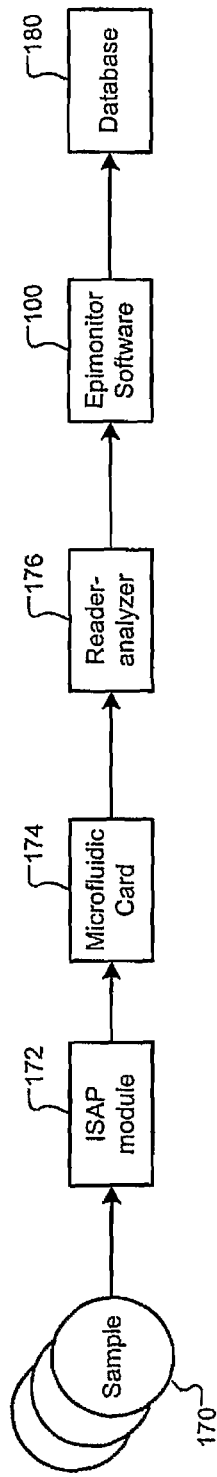
FIG. 3 is a high level process flow diagram illustrating components of an a genetic surveillance and analysis system.

FIG. 3 illustrates a functional flow diagram for a simple genetic surveillance and analysis system 10 implementation. One or more samples 170 are taken from human, plant or animal subjects (or from other sources such as environmental sampler units). The samples 170 are processed, for example, using a stand-alone Integrated Sample and Assay Preparation (ISAP) module 172. In this regard, the user provides the sample 170 as an input to the ISAP module 172, and the ISAP module 172 provides a standardized card, such as a microfluidic card 174, as its output. If desired, the ISAP module 172 can be integrated with the EpiMonitor software platform 100 and thus provide communication capability. Such communication capability and integration into the EpiMonitor software platform 100 allows the operating parameters of the ISAP module 172 to be updated or controlled remotely to conform its operation to rapidly changing analysis parameters and assays.

Once the microfluidic card 174 has been filled with properly prepared sample 170 and PCR reagents including at least one primer probe set, the card 174 can be then inserted into a reader-analyzer instrument 176. In some embodiments, reader-analyzer instrument 176 can be a genetic analysis platform such as, for example, a PCR system. In various embodiments, reader-analyzer instrument 176 may be any of those illustrated in FIG. 1 as instruments 52, 54, and 56. In various embodiments, the reader-analyzer instrument 176 may be capable of performing reverse transcription PCR (RT-PCR), further described below, either simultaneously with PCR or as a separate step.

In various embodiments, the output of the reader-analyzer instrument 176, either as raw data or processed data, can be processed by EpiMonitor software 100 and information extracted from this analysis can be stored in a suitable database 180. The database 180 can be at a central location or it can be distributed across multiple locations. In various embodiments, the EpiMonitor software 100 can mediate bidirectional communication between the components that make up the system such as, for example, the reader-analyzer instrument 176 and database 180, in some implementations also the ISAP module 172 and microfluidic card 174). Although a single data flow has been illustrated (from sample 170 to database 180), similar data flows can occur concurrently at multiple locations distributed throughout the world. The EpiMonitor software 100 coordinates this data gathering among a potentially large number of instruments 176 and ensures that the information extracted from a plurality of reader-analyzer instruments 176 can be stored in the database 180 in a consistent manner that facilitates further operations on the collected information such as, for example, statistical analysis.

Figure 4:
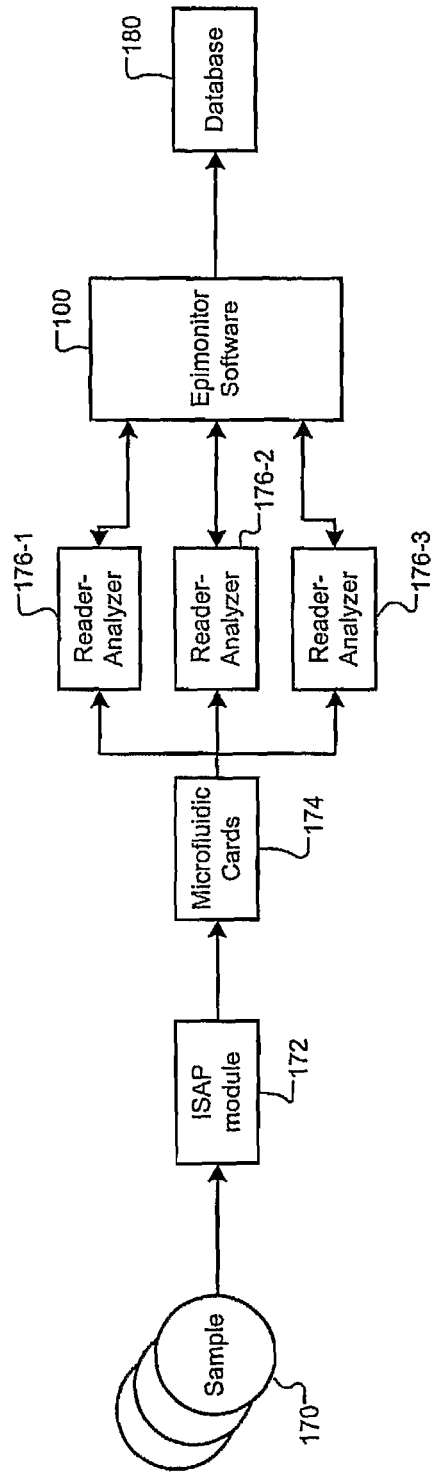
FIG. 4 is an information system that employs a plurality of reader-analyzer instruments.

FIG. 4 illustrates a flowchart of a parallel workflow implementation. In the workflow illustrated in FIG. 3, a single ISAP module 172 supplied microfluidic cards 174 serially to one reader-analyzer instrument 176. In FIG. 4, a single ISAP module 172 prepares a plurality of microfluidic cards 174 for a plurality of reader-analyzer instruments 176-1, 176-2, and 176-3, operating in parallel. This arrangement may be most useful when an analysis uses a short sample and assay preparation time by the ISAP module 172 to prepare a microfluidic card 174 as compared to the time required for analyzing the microfluidic card 174 by one of the plurality of reader-analyzer instrument 176. As such, a single ISAP module 172 can supply a plurality of reader-analyzer instruments 176 without delays.

Figure 5:
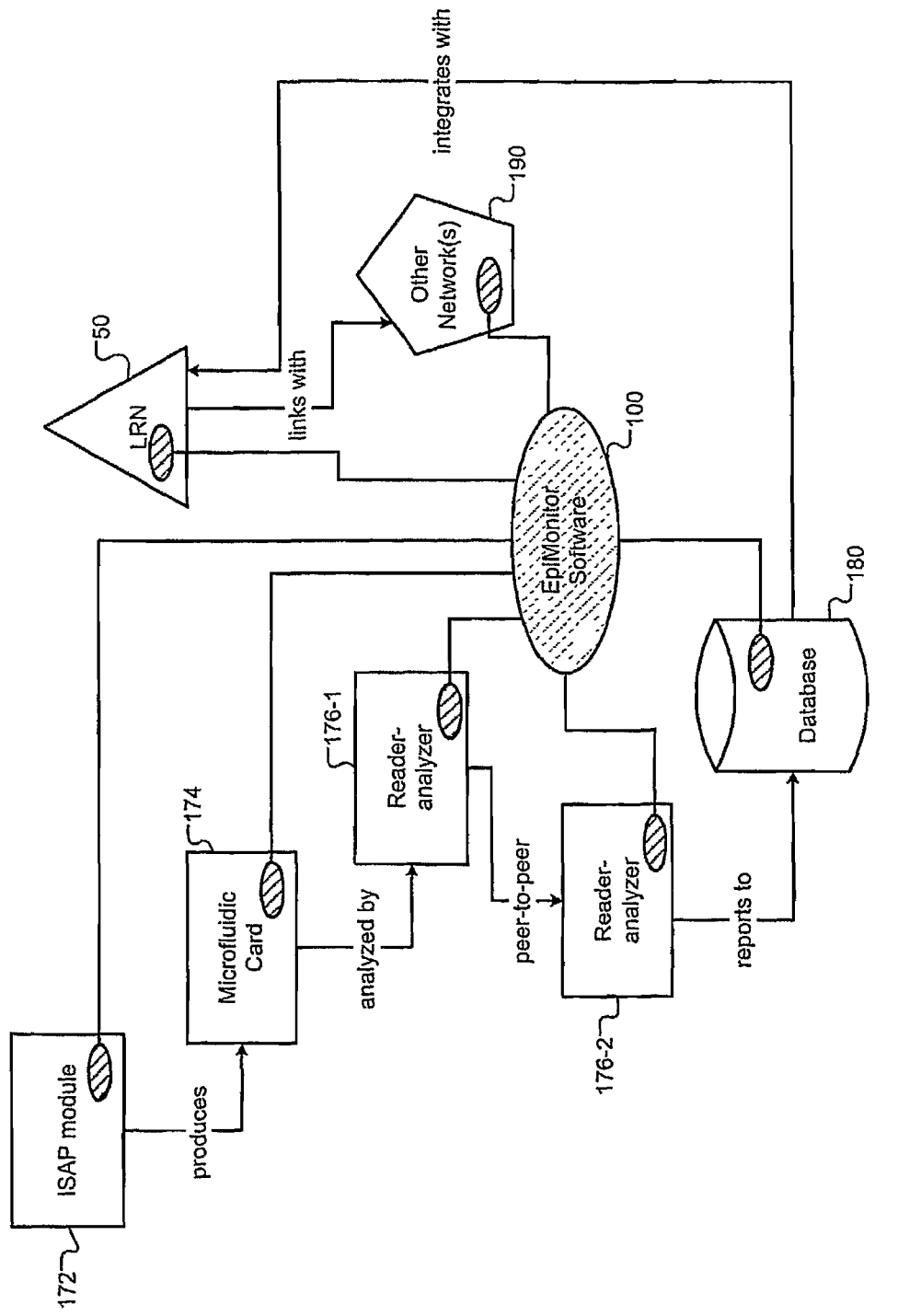
FIG. 5 is a more detailed view further illustrating how an EpiMonitor software platform may be distributed.

Referring to FIG. 5, each of the individual devices and instruments (ISAP module 172, microfluidic card 174, reader-analyzer instruments 176-1 and 176-2, and database 180) can be embedded or associated components of the EpiMonitor software platform 100. The reader-analyzer instruments 176-1 and 176-2 can establish a peer-to-peer relationship, where they communicate information between one another or through an associated network. The interconnecting lines (without arrowheads) of FIG. 5 represent communication pathways for data and/or control instructions made possible by the EpiMonitor software platform 100. The directed arrows show relationships among the interconnected components. Thus, as illustrated, the ISAP module 172 produces the microfluidic card 174. In various embodiments, the microfluidic card 174 can be analyzed by reader-analyzer 176-1, which communicates peer-to-peer with reader-analyzer 176-2. The reader-analyzer 176-2 reports to the database 180. The relationships among components, and the functions that they perform, are managed by the EpiMonitor software platform 100. The EpiMonitor software platform 100 can include components associated with the LRN 50, or with other networks 190, to coordinate analysis and response capabilities.

Figure 6:
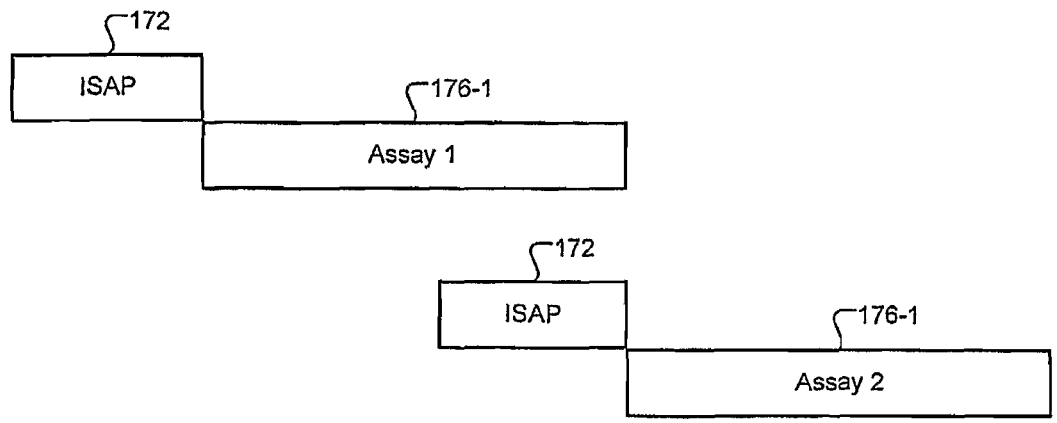
FIG. 6 illustrates one possible parallel processing timing diagram implementation for sample preparation.
Figure 7:
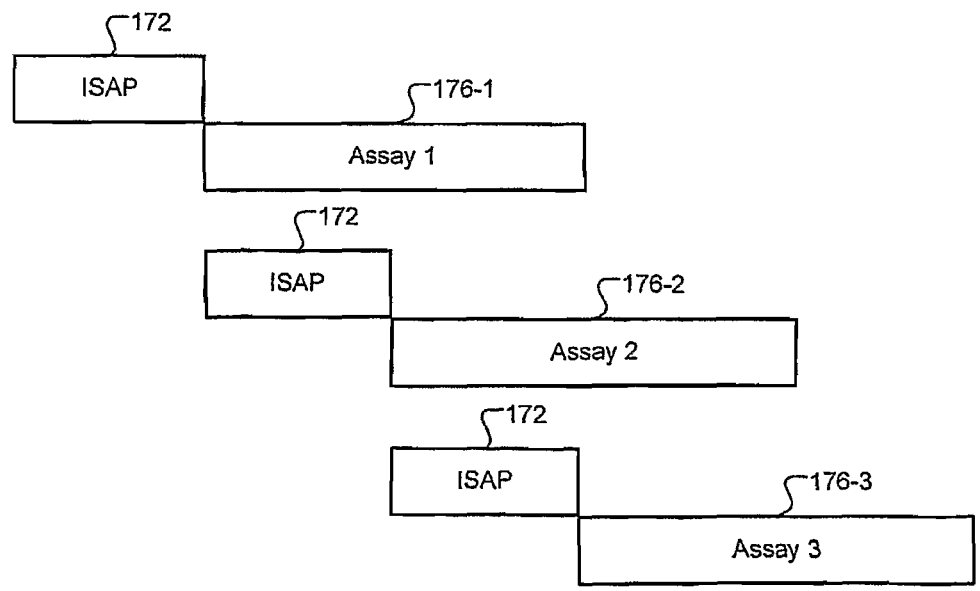
FIG. 7 illustrates another possible parallel processing timing diagram implementation for sample preparation.

FIGS. 6 and 7 each illustrate a possible parallel processing timing diagram. Referring to FIG. 6, the ISAP module 172 produces a first microfluidic card 174, which is then processed by the first reader-analyzer instrument 176-1. While processing is taking place within the first instrument 176-1, the ISAP module 172 prepares a second microfluidic card 174 so that it will be ready for processing by the instrument 176-1 once the first assay processing is completed. In a second parallel processing arrangement, illustrated in FIG. 7, the ISAP module 172 successively prepares three different assays (assay 1, assay 2, assay 3), which are individually processed by three different reader-analyzer instruments 176-1, 176-2, and 176-3.

In each of the reader-analyzer instruments 176 described above, the sample can be tested against a specific assay panel. In various embodiments, such a panel can include desired reagents (e.g., enzymes, primers, probes, etc., when using PCR as discussed below) that are used to perform an assay for target sequences of interest. In an exemplary full-featured system application, the reagents can include a compound set for detecting a plurality of selected bacterial spores, gram-positive or gram-negative bacteria, and/or viruses (whether DNA or RNA-based). A combination of these target sequences can define an assay panel particularly useful for a particular diagnosis.

In various embodiments, one example of such an assay panel can be an upper respiratory panel that includes several of the most common bacterial and viral pathogens responsible for, or associated with, upper respiratory infectious disease as shown in Table 1. The exemplary assay panel includes twenty-one distinct pathogens and five controls (GAPDH, IPC1, IPC10, IPC0.1, and buffer). In this example, six of the twenty-one pathogens are included a second time with the incorporation of an internal positive control (IPC).

TABLE 1

| Assay Name | Pathogen |
| --- | --- |
| B-pert/holm/1000x | *Bordetella pertussis* + 1000x IPC |
| C-pneu/100x | *Chlamydia pneumoniae* + 100x IPC |
| L-pneu/10x | *Legionella pneumophila* + 10x IPC |
| M-pneu/1x | *Mycoplasma pneumoniae* + 1x IPC |
| C-botu/0.1x | *Clostridium botulinum* + 0.1x IPC |
| S-pneu/0.01x | *Streptococcus pneumoniae* + 0.01x IPC |
| M-cata | *Moraxella catarrhalis* |
| N-meni | *Neisseria meningitidis* |
| H-infl | *Haemophilus influenzae* (Type B) |
| S-aure | *Stapphylococcus Aureus* |
| GAPDH | GAPDH control (for QC purposes) |
| M-tube | *Mycobacterium tuberculosis* |
| RSV-A | Respiratory Syncytial Virus (RSV) A |
| RSV-B | Respiratory Syncytial Virus (RSV) B |
| Hadv-1-2-5-6 | Human AdV (Types 1, 2, 5, 6) |
| EntV | Enterovirus |
| SARS3-CoV | SARS-CoV |
| Metapneu-V | Metapneumovirus |
| Infl-A | Influenza A |
| Infl-B | Influenza B |
| CMV | Cytomegalovirus |
| PIV | Parainfluenza Virus |
| B-pert/holm | *Bordetella pertussis* |
| C-pneu | *Chlamydia pneumoniae* |
| L-pneu | *Legionella pneumophila* |
| M-pneu | *Mycoplasma pneumoniae* |
| C-botu | *Clostridium Botulinum* |
| S-pneu | *Streptococcus pneumoniae* |
| IPC1 | Internal Positive control |
| IPC10 | Internal Positive control |
| IPC0.1 | Internal Positive Control |
| Buffer | Negative Control |

Multiple configurations of such assay panels can be created and other panels can be configured as desired. The number of target sequences in the panel may depend on factors, including the nature of the panel and the implementation of a specific instrumentation platform of reader-analyzer 176. In one exemplary application, a laboratory instrument 52 might perform between approximately 10-20 assays while a handheld instrument 56 may perform fewer, possibly just one assay. In addition to an assay panel that includes multiple pathogenic species, the assay panel can include multiple strains of a particular pathogen for purposes such as identifying potential drug resistances, thereby providing a potential guide to effective therapy. The assay panel can also contain multiple DNA targets or other target sequences for a single pathogen to potentially improve specificity in detection. Other potential assay panel combinations/formulations can be devised for numerous useful purposes. For example, an assay panel could include avian flu H5:N1 or a group of strains of pathogenic E. Coli which could include 0157:H7.

of liquid expressed from these swabs to facilitate lysis and ready the sample for purification. The nucleic acids produced are highly pure and free of cross-contamination. Purification reagents can also be added manually to the microfluidic card 174 by the ISAP module 172 operator. An optional graphical user interface incorporated to the ISAP module 172 can provide easy access to pre-programmed methods, and affords the ability to create, edit, and store custom purification routines. It should also be appreciated that the present teachings may be used in connection with microfluidic cards 174 and other principles, such as set forth in U.S. Pat. Nos. 6,124,138 and 6,126,899.

Table 2 depicts an exemplary layout of a microfluidic card 174, given the pathogen panel of Table 1. There are sixteen rows (A-P), and twenty-four columns (1-24), yielding 384 (16*24=384) wells. Because each target sequence/control can be repeated at least eight times in the card layout, this card can simultaneously process eight samples.

TABLE 2

| | 1 | 2 | 3 | 4 | 5 | 6 | 7 | 8 | 9 | 10 |
|---|---|---|---|---|---|---|---|---|---|---|
| A | B-pert/holm/1000x | C-pneu/100x | L-pneu/10x | M-pneu/1x | C-botu/0.1x | S-pneu/0.01x | M-cata | N-meni | H-infl | S-aure |
| B | B-pert/holm | C-pneu | L-pneu | M-pneu | C-botu | S-pneu | M-cata | N-meni | H-infl | S-aure |
| C | B-pert/holm/1000x | C-pneu/100x | L-pneu/10x | M-pneu/1x | C-botu/0.1x | S-pneu/0.01x | M-cata | N-meni | H-infl | S-aure |
| D | B-pert/holm | C-pneu | L-pneu | M-pneu | C-botu | S-pneu | M-cata | N-meni | H-infl | S-aure |
| E | B-pert/holm/1000x | C-pneu/100x | L-pneu/10x | M-pneu/1x | C-botu/0.1x | S-pneu/0.01x | M-cata | N-meni | H-infl | S-aure |
| F | B-pert/holm | C-pneu | L-pneu | M-pneu | C-botu | S-pneu | M-cata | N-meni | H-infl | S-aure |
| G | B-pert/holm/1000x | C-pneu/100x | L-pneu/10x | M-pneu/1x | C-botu/0.1x | S-pneu/0.01x | M-cata | N-meni | H-infl | S-aure |
| H | B-pert/holm | C-pneu | L-pneu | M-pneu | C-botu | S-pneu | M-cata | N-meni | H-infl | S-aure |
| I | B-pert/holm/1000x | C-pneu/100x | L-pneu/10x | M-pneu/1x | C-botu/0.1x | S-pneu/0.01x | M-cata | N-meni | H-infl | S-aure |
| J | B-pert/holm | C-pneu | L-pneu | M-pneu | C-botu | S-pneu | M-cata | N-meni | H-infl | S-aure |
| K | B-pert/holm/1000x | C-pneu/100x | L-pneu/10x | M-pneu/1x | C-botu/0.1x | S-pneu/0.01x | M-cata | N-meni | H-infl | S-aure |
| L | B-pert/holm | C-pneu | L-pneu | M-pneu | C-botu | S-pneu | M-cata | N-meni | H-infl | S-aure |
| M | B-pert/holm/1000x | C-pneu/100x | L-pneu/10x | M-pneu/1x | C-botu/0.1x | S-pneu/0.01x | M-cata | N-meni | H-infl | S-aure |
| N | B-pert/holm | C-pneu | L-pneu | M-pneu | C-botu | S-pneu | M-cata | N-meni | H-infl | S-aure |
| O | B-pert/holm/1000x | C-pneu/100x | L-pneu/10x | M-pneu/1x | C-botu/0.1x | S-pneu/0.01x | M-cata | N-meni | H-infl | S-aure |
| P | B-pert/holm | C-pneu | L-pneu | M-pneu | C-botu | S-pneu | M-cata | N-meni | H-infl | S-aure |

| | 11 | 12 | 13 | 14 | 15 | 16 | 17 | 18 | 19 | 20 | 21 | 22 | 23 | 24 |
|---|---|---|---|---|---|---|---|---|---|---|---|---|---|---|
| A | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| B | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| C | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| D | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| E | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| F | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| G | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| H | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| I | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| J | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| K | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| L | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| M | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| N | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |
| O | GAPDH | M-tube | RSV-A | RSV-B | Hadv-1-2-5-6 | EntV | SARS3-CoV | Metapneu-V | Infl-A | Infl-B | CMV | PIV | IPC10 | IPC1 |
| P | GAPDH | M-tube | RSV-A | RSV-B | Hadv-1-2-5-6 | EntV | SARS3-CoV | Metapneu-V | Infl-A | Infl-B | CMV | PIV | IPC0.1 | BL |

Figure 8:
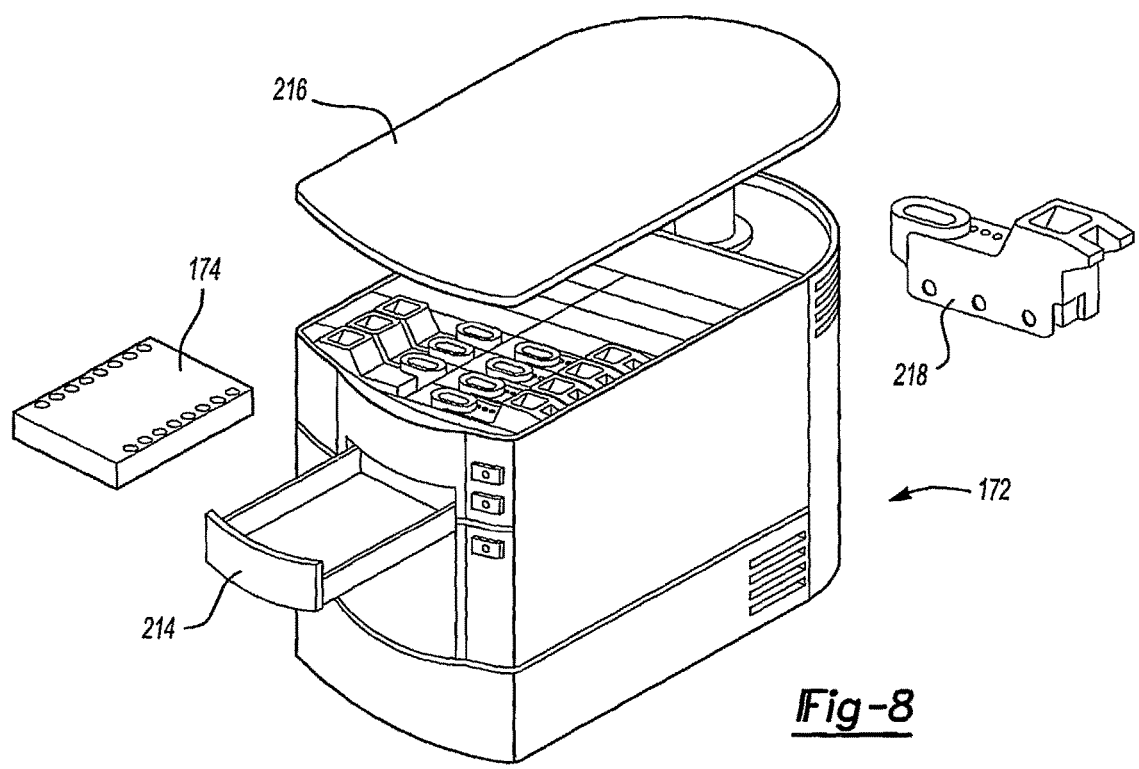
FIG. 8 illustrates an example of an integrated sample and assay preparation device.

In various embodiments, to create an assay panel, an ISAP module 172, such as that illustrated in FIG. 8, can be used. The ISAP module 172 can accept one or more microfluidic cards 174 into a loading tray 214. A lid 216 of the ISAP module 172 can be raised so that reagent holding devices 218 can be removed and inserted. These reagent holding devices 218 provide the ISAP module 172 with a supply of reagents that are selectively introduced to the microfluidic card 174.

The ISAP module 172 can accept samples 170 from the environment or from a patient, such as nasal, throat, and/or nasopharyngeal swabs. The ISAP module 172 treats samples In various embodiments, microfluidic card 174 may be other than the 384-well microfluidic card 174 layout and filling systems and/or microfluidics can also be used in implementing loading samples and reagents to the microfluidic card 174. By way of non-limiting illustration, a centrifugal filling system and microfluidic card system described in U.S. Pat. No. 6,627,159 can be used to fill the card from the loading ports. An exemplary centrifuge can be the Sorvall® Legend T Centrifuge with a 4-Place Swinging Bucket Rotor twist-on fixture, which does not require a tool to secure it to the centrifuge.

Figure 9:
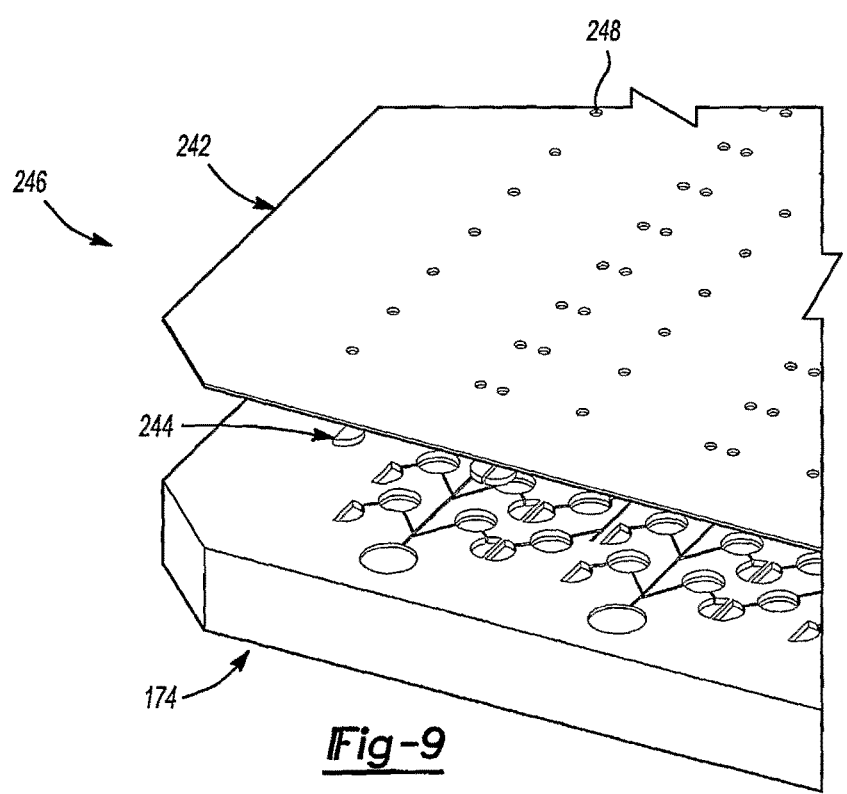
FIG. 9 is an exploded view of an assay card assembly.
Figure 10:
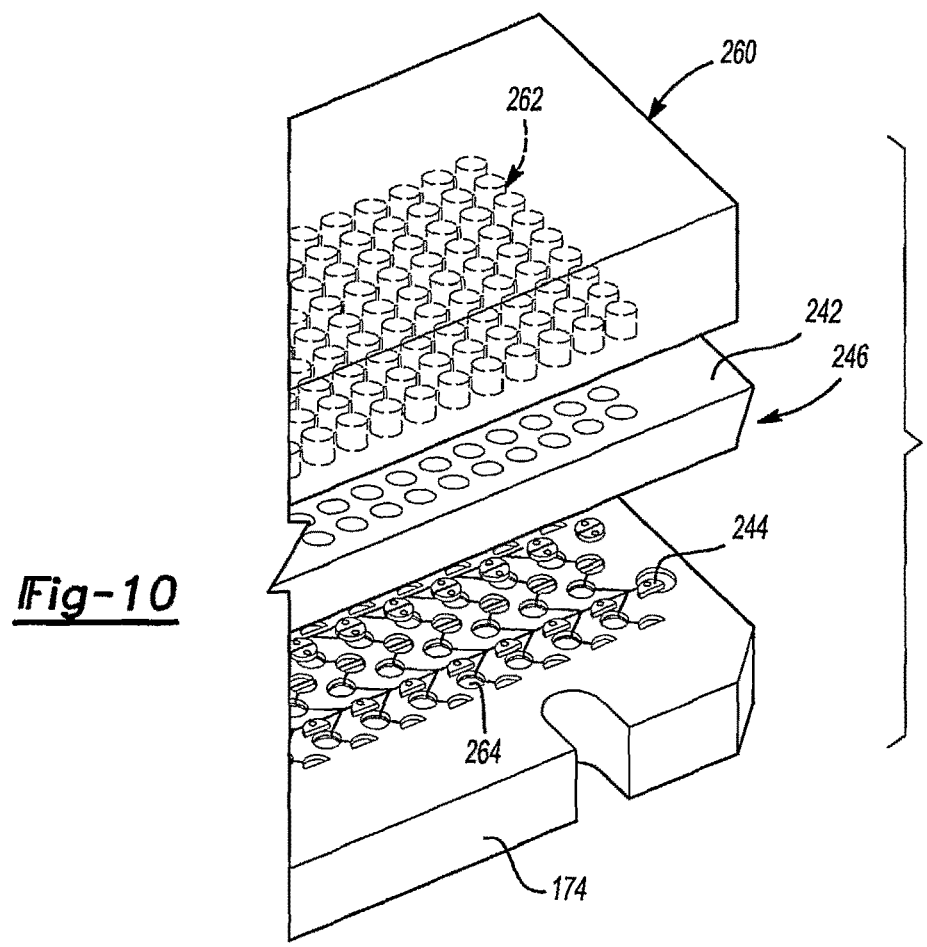
FIG. 10 is an exploded view of a thermal transfer plate.

Referring now to FIG. 9, an example of a microfluidic card 174, which may be injection molded, serves as the base for microfluidic card assembly 246. A gas-permeable membrane 244 can be placed onto the microfluidic card 174. Above the membrane 244 can be situated a thin film cover layer 242, including vent holes 248. Referring now to FIG. 10, a thermal transfer plate 260 can be demonstrated. The thermal transfer plate 260 can be interfaced with the microfluidic card assembly 246 of FIG. 9. The thermal transfer plate 260 seals inlet and outlet channels of the microfluidic card assembly 246 to isolate reaction chambers 264. Circular thermal dies 262 (which have an internal diameter of 2.5 mm in various embodiments) of the thermal transfer plate 260 create a heat seal around each reaction chamber 264.

Figure 11:
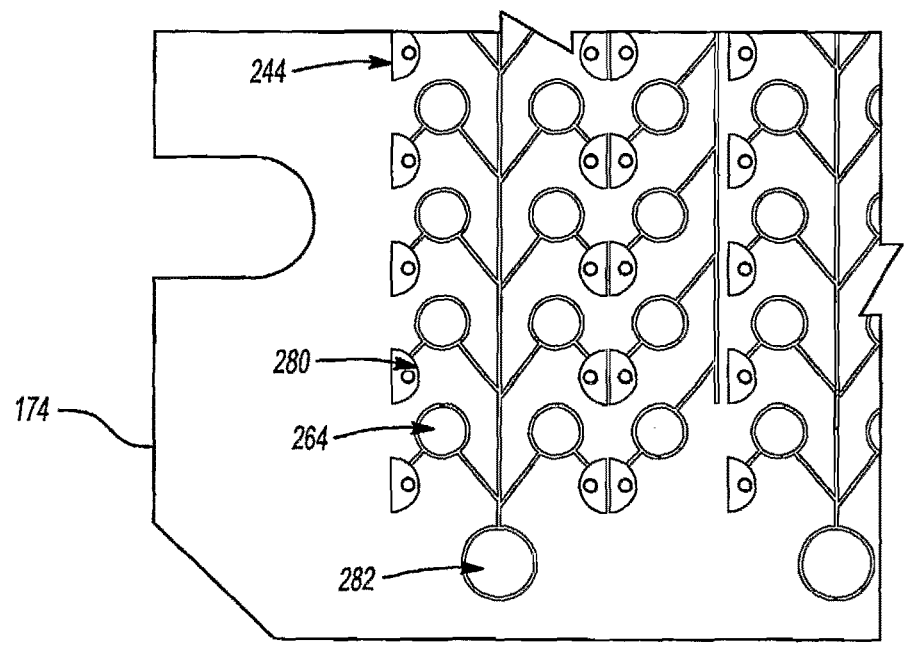
FIG. 11 is a top view of the assay card assembly of FIG. 9.

FIG. 11 illustrates a top view of the microfluidic card assembly 246. The gas permeable membrane 244 holds up liquid during filling. A vent hole 248 can be located above the gas permeable membrane 244. A reaction chamber 264 and a sample inlet port 282 is shown, into which samples can be loaded from an ISAP module 172, or manually with a syringe. In various embodiments, the microfluidic card 174 can be loaded with a volume of 100 µL, and each well has a volume of 1.5 µL.

Figure 12:
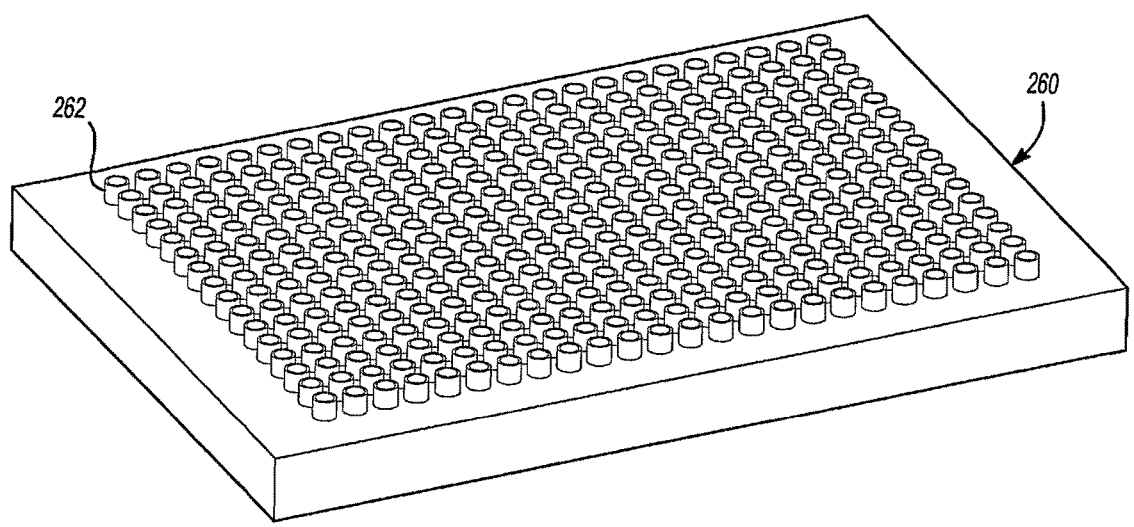
FIG. 12 is a perspective view of the thermal transfer plate of FIG. 10.
Figure 13:
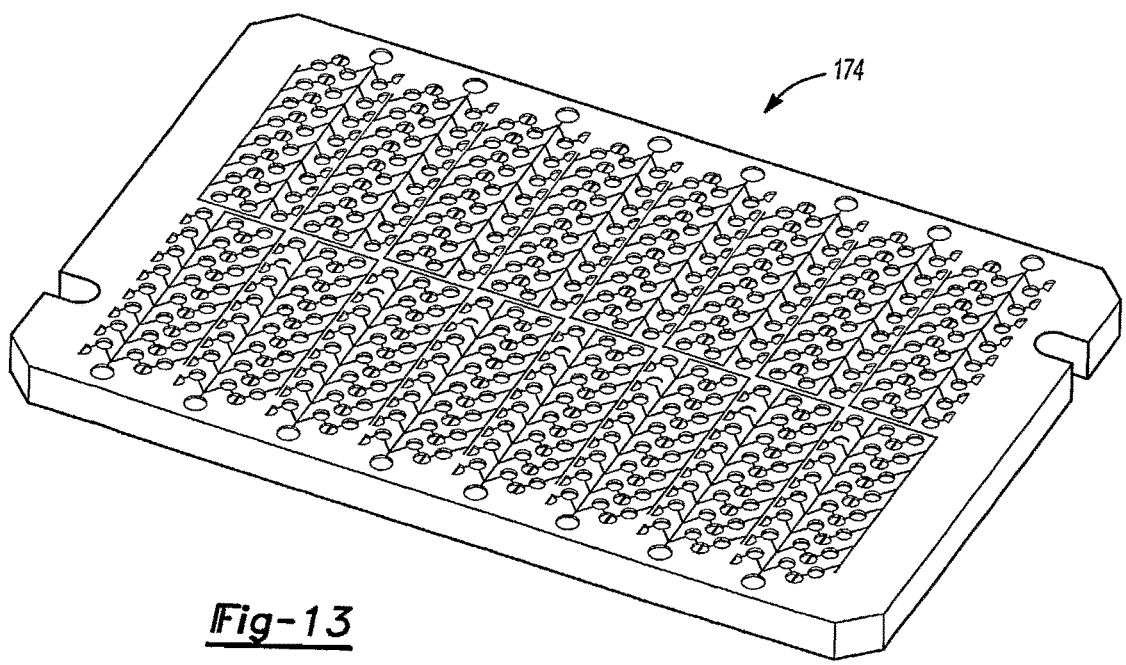
FIG. 13 is a perspective view of a 384-well assay card.
Figure 15:
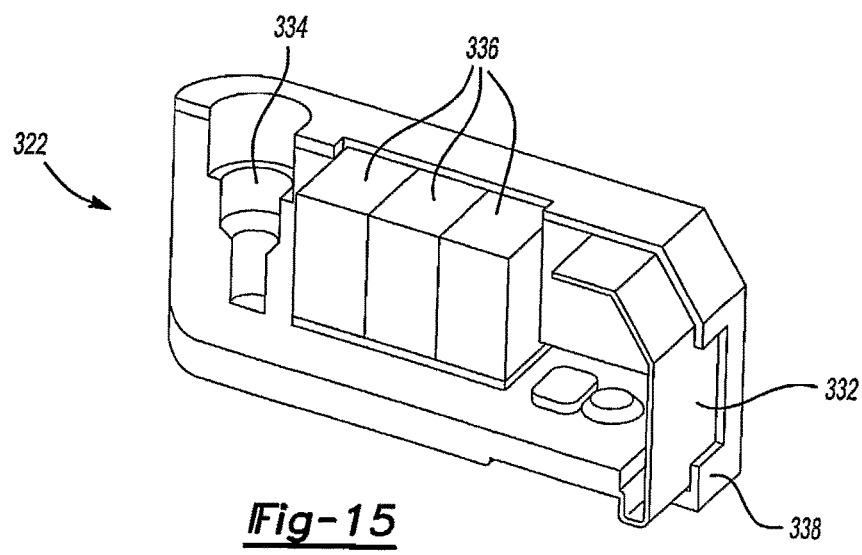
FIG. 15 is a perspective view of the cartridge usable by the portable medical device of FIG. 14.

FIG. 12 illustrates a perspective view of the thermal transfer plate 260 of FIG. 10. Each of the 384 thermal transfer dies 262 isolates reaction chambers 264 (not shown) in the microfluidic card 174. The size of the circular dies 262 depends upon reaction chamber 264 size, but in various embodiments, can be about a 2.5 mm inside diameter. Referring now to FIG. 15, a perspective view of the microfluidic card 174 comprising microchannels within the microfluidic card 174 can be routed to create any arbitrary layout desired. In various embodiments, the card can be about 85.7 mm in width and about 127.0 mm in length.

In various embodiments, microfluidic card 174 themselves can be provided with embedded processor capability. For example, the microfluidic card 174 can be provided with one or more thermal sensors, thereby allowing actual thermal data to be collected by the reader-analyzer instrument 176. In various embodiments, the EpiMonitor software platform 100 can supply the microfluidic card 174 with data, which can be used in the event that subsequent tests or quality control procedures may be needed. Such a capability can be provided by including a SmartCard, RFID, or other such semiconductor device mounted in the microfluidic card 174. In various embodiments, microfluidic card 174 can also communicate with the rest of the system 10 using the EpiMonitor software platform 100. In various embodiments, a reader-analyzer instrument 176 can perform PCR on prepared assay panels, and detect resulting fluorescence. The reader-analyzer instrument 176 can also process this data to estimate the number of copies of a target sequence initially present in a sample, or whether a particular target sequence may be present. In various embodiments, the reader-analyzer instrument 176 can be controlled by a computer or laptop, so that processing power can be A connection between the reader-analyzer instrument 176 and the computer can be wired or wireless, and the connection between the computer and the server hosting EpiMonitor software platform 100 may be wired or wireless. In various embodiments, reader-analyzer instrument 176 is connected to a computer that can be part of a client server system and, in various embodiments, at least part of the EpiMonitor software 100 host at a server may be downloaded to the chart for numbering crunching and/or data analysis at the client.

In various embodiments, a Fast real-time PCR option can give real-time PCR results in a 96-well format in approximately 35 minutes, inclusive of sample preparation. In various embodiments, reader-analyzer instruments 176 used for the amplification of polynucleic acids, such as by PCR. Briefly, by way of background, PCR can be used to amplify a sample of target Deoxyribose Nucleic Acid (DNA) for analysis. Typically, the PCR reaction involves copying the strands of the target DNA and then using the copies to generate additional copies in subsequent cycles. Each cycle doubles the amount of the target DNA present, thereby resulting in a geometric progression in the number of copies of the target DNA. The temperature of a double-stranded target DNA is elevated to denature the DNA, and the temperature is then reduced to anneal at least one primer to each strand of the denatured target DNA. In various embodiments, the target DNA can be a cDNA.

In various embodiments, primers are used as a pair—a forward primer and a reverse primer—and can be referred to as a primer pair or primer set. In various embodiments, the primer set comprises a 5' upstream primer that can bind with the 5' end of one strand of the denatured target DNA and a 3' downstream primer that can bind with the 3' end of the other strand of the denatured target DNA. Once a given primer binds to the strand of the denatured target DNA, the primer can be extended by the action of a polymerase. In various embodiments, the polymerase can be a thermostable DNA polymerase, for example, a Taq polymerase. The product of this extension, which sometimes may be referred to as an amplicon, can then be denatured from the resultant strands and the process can be repeated. Temperatures suitable for carrying out the reactions are well known in the art. Certain basic principles of PCR are set forth in U.S. Pat. Nos. 4,683,195, 4,683,202, 4,800,159, and 4,965,188, each issued to Mullis et al.

In various embodiments, PCR can be conducted under conditions allowing for quantitative and/or qualitative analysis of one or more target DNA. Accordingly, detection probes can be used for detecting the presence of the target DNA in an assay. In various embodiments, the detection probes can comprise physical (e.g., fluorescent) or chemical properties that change upon binding of the detection probe to the target DNA. Various embodiments of the present teaching can provide real time fluorescence-based detection and analysis of amplicons as described, for example, in PCT Publication No. WO 95/30139 and U.S. patent application Ser. No. 08/235,411.

In various embodiments, a sample can be analyzed as a homogenous polynucleotide amplification assay, for coupled amplification and detection, wherein the process of amplification generates a detectable signal and the need for subsequent sample handling and manipulation to detect the amplified product is minimized or eliminated. Homogeneous assays can provide for amplification that is detectable without opening a sealed well or further processing steps once amplification is initiated. Such homogeneous assays can be suitable for use in conjunction with detection probes. For example, in various embodiments, the use of an oligonucleotide detection probe, specific for detecting a particular target DNA can be included in an amplification reaction in addition to a DNA binding agent of the present teachings.

Homogenous assays among those useful herein are described, for example, in commonly assigned U.S. Pat. No. 6,814,934. In various embodiments, methods are provided for detecting a plurality of targets. Such methods include those comprising forming an initial mixture comprising an analyte sample suspected of comprising the plurality of targets, a polymerase, and a plurality of primer sets. In various embodiments, each primer set comprises a forward primer and a reverse primer and at least one detection probe unique for one of the plurality of primer sets. In various embodiments, the initial mixture can be formed under conditions in which one primer elongates if hybridized to a target.

In various embodiments, reagents are provided comprising a master mix comprising at least one of catalysts, initiators, promoters, cofactors, enzymes, salts, buffering agents, chelating agents, and combinations thereof. In various embodiments, reagents can include water, a magnesium catalyst (such as MgCl2), polymerase, a buffer, and/or dNTP. In various embodiments, specific master mixes can comprise AmpliTaq® Gold PCR Master Mix, TaqMan® Universal Master Mix, TaqMan® Universal Master Mix No AmpErase® UNG, Assays-by-DesignSM, Pre-Developed Assay Reagents (PDAR) for gene expression, PDAR for allelic discrimination and Assays-On-Demand®, (all of which are marketed by Applied Biosystems). However, the present teachings should not be regarded as being limited to the particular chemistries and/or detection methodologies recited herein, but may employ Taqman®; Invader®; Taqman Gold®; protein, peptide, and immuno assays; receptor binding; enzyme detection; and other screening and analytical methodologies.

In various embodiments, a solid support such as, for example, a microplate or a microfluidic card 174, can be covered with a sealing liquid prior to performance of analysis or reaction of assay. For example, in various embodiments, a sealing liquid can be applied to the surface of a microplate comprising reaction spots comprising an assay or for amplification of polynucleotides. In various embodiments, a sealing liquid can be a material which substantially covers the material retention regions (e.g., reaction spots) on the microplate so as to contain materials present in the material retention regions, and substantially prevent movement of material from one reaction region to another reaction region on the substrate. In various embodiments, the sealing liquid can be any material which is not reactive with assay under normal storage or usage conditions. In various embodiments, the sealing liquid can be substantially immiscible with assay.

In various embodiments, the sealing liquid can be transparent, have a refractive index similar to glass, have low or no fluorescence, have a low viscosity, and/or be curable. In various embodiments, the sealing liquid can comprise a flowable, curable fluid such as a curable adhesive selected from the group consisting of: ultra-violet-curable and other light-curable adhesives; heat, two-part, or moisture activated adhesives; and cyanoacrylate adhesives. In various embodiments, the sealing liquid can be selected from the group consisting of mineral oil, silicone oil, fluorinated oils, and other fluids that are substantially non-miscible with water. In various embodiments, the sealing liquid can be a fluid when it is applied to the surface of the microplate and in various embodiments, the sealing liquid can remain fluid throughout an analytical or chemical reaction using the microplate. In various embodiments, the sealing liquid can become a solid or semi-solid after it is applied to the surface of the microplate.

As should be appreciated from the discussion herein, the present teachings can find utility in a wide variety of amplification methods, such as PCR, Reverse-Transcription PCR (RT-PCR), Ligation Chain Reaction (LCR), Nucleic Acid Sequence Based Amplification (NASBA), self-sustained sequence replication (3SR), strand displacement activation (SDA), Q (3replicase) system, isothermal amplification methods, and other known amplification method or combinations thereof. Additionally, the present teachings can find utility for use in a wide variety of analytical techniques, such as ELISA; DNA and RNA hybridizations; antibody titer determinations; gene expression; recombinant DNA techniques; hormone and receptor binding analysis; and other known analytical techniques. Still further, the present teachings can be used in connection with such amplification methods and analytical techniques using not only spectrometric measurements, such as absorption, fluorescence, luminescence, transmission, chemiluminescence, and phosphorescence, but also colorimetric or scintillation measurements or other known detection methods.

In various embodiments, the reagents can comprise first and second oligonucleotides effective to bind selectively to adjacent, contiguous regions of target DNA and that can be ligated covalently by a ligase enzyme or by chemical means. Such oligonucleotide ligation assays (OLA) are described, for example, in U.S. Pat. No. 4,883,750; and Landegren, U., et al., *Science* 241:1077 (1988). In various embodiments, a detection probe comprises a moiety that facilitates detection of a nucleic acid sequence, and in various embodiments, quantifiably. In various embodiments, a detection probe can comprise, for example, a fluorophore such as a fluorescent dye, a hapten such as a biotin or a digoxygenin, a radioisotope, an enzyme, or an electrophoretic mobility modifier. In various embodiments, the level of amplification can be determined using a fluorescently labeled oligonucleotide. In various embodiments, a detection probe can comprise a fluorophore further comprising a fluorescence quencher.

In various embodiments, a detection probe can comprise a fluorophore and can be, for example, a 5'-exonuclease assay probe such as a TaqMan® probe (marketed by Applied Biosystems), a stem-loop Molecular Beacon (see, e.g., U.S. Pat. Nos. 6,103,476 and 5,925,517, *Nature Biotechnology* 14:303-308 (1996); Vet et al., *Proc Natl Acad Sci USA.* 96:6394-6399 (1999)), a stemless or linear molecular beacon (see., e.g., PCT Patent Publication No. WO 99/21881), a Peptide Nucleic Acid (PNA) Molecular Beacon™ (see, e.g., U.S. Pat. Nos. 6,355,421 and 6,593,091), a linear PNA Molecular Beacon (see, e.g., Kubista et al., *SPIE* 4264:53-58 (2001)), a flap endonuclease probe (see, e.g., U.S. Pat. No. 6,150,097), a Sunrise®/Amplifluor® probe (see, e.g., U.S. Pat. No. 6,548,250), a stem-loop and duplex Scorpion™ probe (see, e.g., Solinas et al., *Nucleic Acids Research* 29:E96 (2001), and U.S. Pat. No. 6,589,743), a bulge loop probe (see, e.g., U.S. Pat. No. 6,590,091), a pseudo knot probe (see, e.g., U.S. Pat. No. 6,589,250), a cyclicon (see, e.g., U.S. Pat. No. 6,383,752), an MGB Eclipse™ probe (Marketed by Epoch Biosciences), a hairpin probe (see, e.g., U.S. Pat. No. 6,596,490), a peptide nucleic acid (PNA) light-up probe, a self-assembled nanoparticle probe, or a ferrocene-modified probe described, for example, in U.S. Pat. No. 6,485,901; Mhlanga et al., *Methods* 25:463-471 (2001); Whitcombe et al., *Nature Biotechnology* 17:804-807 (1999); Isacsson et al., *Molecular Cell Probes* 14:321-328 (2000); Svanvik et al., *Anal. Biochem.* 281:26-35 (2000); Wolffs et al., *Biotechniques* 766:769-771 (2001), Tsourkas et al., *Nucleic Acids Research* 30:4208-4215 (2002); Riccelli et al., *Nucleic Acids Research* 30:4088-4093 (2002); Zhang et al., Sheng Wu Hua Xue Yu Sheng Wu Li Xue Bao (Shanghai) (*Acta Biochimica et Biophysica Sinica*) 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); Yu et al., *J. Am. Chem. Soc* 14:11155-11161 (2001).

In various embodiments, a detection probe can comprise a sulfonate derivative of a fluorescent dye, a phosphoramidite form of fluorescein, or a phosphoramidite forms of CY5. Detection probes among those useful herein are also disclosed, for example, in U.S. Pat. Nos. 5,188,934, 5,750,409, 5,847,162, 5,853,992, 5,936,087, 5,986,086, 6,020,481, 6,008,379, 6,130,101, 6,140,500, 6,140,494, 6,191,278, and 6,221,604. Energy transfer dyes among those useful herein include those described in U.S. Pat. Nos. 5,728,528, 5,800, 996, 5,863,727, 5,945,526, 6,335,440, 6,849745, U.S. Patent Application Publication No. 2004/0126763 A1, PCT Publication No. WO 00/13026A1, PCT Publication No. WO 01/19841A1, U.S. Patent Application Ser. No. 60/611,119, filed Sep. 16, 2004, and U.S. patent application Ser. No. 10/788,836, filed Feb. 26, 2004. In various embodiments, a detection probe can comprise a fluorescence quencher such as a black hole quencher (marketed by Metabion International AG), an Iowa Black™ quencher (marketed by Integrated DNA Technologies), a QSY quencher (marketed by Molecular Probes), and Dabsyl and Eclipse™ Dark Quenchers (marketed by Epoch).

In various embodiments, amplified sequences can be detected in double-stranded form by a detection probe comprising an intercalating or a crosslinking dye, such as ethidium bromide, acridine orange, or an oxazole derivative, for example, SYBR Green® (marketed by Molecular Probes, Inc.), which exhibits a fluorescence increase or decrease upon binding to double-stranded nucleic acids. In various embodiments, a detection probe comprises SYBR Green® or Pico Green® (marketed by Molecular Probes, Inc.). In various embodiments, a detection probe can comprise an enzyme that can be detected using an enzyme activity assay. An enzyme activity assay can utilize a chromogenic substrate, a fluorogenic substrate, or a chemiluminescent substrate. In various embodiments, the enzyme can be an alkaline phosphatase, and the chemiluminescent substrate can be (4-methoxyspiro[1,2-dioxetane-3,2'(5'-chloro)-tricyclo[3.3.1.13,7]decan]-4-yl)phenylphosphate. In various embodiments, a chemiluminescent alkaline phosphatase substrate can be CDP-Star® chemiluminescent substrate or CSPD® chemiluminescent substrate (marketed by Applied Biosystems).

In various embodiments, the present teachings provide methods and apparatus for Reverse Transcriptase PCR (RT-PCR), which include the amplification of a Ribonucleic Acid (RNA) target. In various embodiments, assay can comprise a single-stranded RNA target, which comprises the sequence to be amplified (e.g., an mRNA), and can be incubated in the presence of a reverse transcriptase, two primers, a DNA polymerase, and a mixture of dNTPs suitable for DNA synthesis. During this process, one of the primers anneals to the RNA target and can be extended by the action of the reverse transcriptase, yielding an RNA/cDNA doubled-stranded hybrid. This hybrid can be then denatured and the other primer anneals to the denatured cDNA strand. Once hybridized, the primer can be extended by the action of the DNA polymerase, yielding a double-stranded cDNA, which then serves as the double-stranded target for amplification through PCR, as described herein. RT-PCR amplification reactions can be carried out with a variety of different reverse transcriptases, and in various embodiments, a thermostable reverse-transcriptions can be used. Suitable thermostable reverse transcriptases can comprise, but are not limited to, reverse transcriptases such as AMV reverse transcriptase, MuLV, and Tth reverse transcriptase.

In various embodiments, assay can be an assay for the detection of RNA, including small RNA. Detection of RNA molecules can be, in various circumstances, very important to molecular biology, in research, industrial, agricultural, and clinical settings. Among the types of RNA that are of interest in various embodiments are, for example, naturally occurring and synthetic regulatory RNAs such as small RNA molecules (Lee, et al., Science 294: 862-864, 2001; Ruvkun, Science 294: 797-799; Pfeffer et al., 304: Science 734-736, 2004; Ambros, Cell 107: 823-826, 2001; Ambros et al., RNA 9: 277-279, 2003; Carrington and Ambros, *Science* 301: 336-338, 2003; Reinhart et al., *Genes Dev.* 16: 1616-1626, 2002 Aravin et al., Dev. Cell 5: 337-350, 2003, Tuschel et al., Science 294: 853-858, 2001; Susi P. et al., Plant Mol. Biol. 54: 157-174, 2004; Xie et al., PLoS Biol. 2: E104, 2004). Small RNA molecules, such as, for example, micro RNAs (miRNA), short interfering RNAs (siRNA), small temporal RNAs (stRNA) and short nuclear RNAs (snRNA), can be, typically, less than about 40 nucleotides in length and can be of low abundance in a cell.

With appropriate detection probes, reader-analyzer instrument 176 can detect miRNA expression found in, for instance, cell samples taken at different stages of development. In various embodiments, coexpression patterns can be analyzed across microfluidic card 174 with TaqMan® sensitivity, specificity, and dynamic range. In various embodiments, such methods obviate the need for running further assays to validate the expression levels. In various embodiments, reader-analyzer instrument 176 can be used to validate that siRNA molecules have successfully, post-translationally regulated the gene expression patterns of interest. In various embodiments, such methods may be useful during the manipulation of gene expression patterns using siRNAs in order to elucidate gene function and/or interrelationships amongst genes. In various embodiments, gene expression patterns can be introduced into living cells, cellular assays can be seen on reader-analyzer instrument 176 and can reveal gene functions. In various embodiments, analysis for small RNA can be run on reader-analyzer instrument 176 allowing for a high number of simultaneous assays on a single sample with performance that obviates the need for secondary assays to validate the gene expression results.

In various embodiments, multiplex methods are provided wherein assay comprises a first universal primer that binds to a complement of a first target, a second universal primer that binds to a complement of a second target, a first detection probe comprising a sequence that binds to the sequence comprised by the first target, and a second detection probe comprising a sequence that binds to a sequence comprised by the second target. In various embodiments, at least some of the plurality of wells of comprise a solution operable to perform multiplex PCR. The first and second detection probes can comprise different labels, for example, different fluorophores such as, in non-limiting example, VIC and FAM. Sequences of the first and second detection probes can differ by as little as one nucleotide, two nucleotides, three nucleotides, four nucleotides, or greater, provided that hybridization occurs under conditions that allow each detection probe to hybridize specifically to its corresponding detection probe.

In various embodiments, multiplex PCR can be used for relative quantification, where one primer set and detection probe amplifies the target DNA and another primer set and detection probe amplifies an endogenous reference. In various embodiments, the present teachings provide for analysis of at least four DNA targets in each of the plurality of wells and/or analysis of a plurality of DNA targets and a reference in each of a plurality of wells in microfluidic card 174.

In various embodiments, DNA applications such as, for example, PCR, may be detected using electrochemical detection methods. In various embodiments, a hand held pathogenic detection device utilizes electrochemical detection. In various embodiments, such electrochemical detection methods employ Taq polymerase and 5'-exonucleoase activity preamplification, as described below. In such electrochemical detection, the use of a fluorescent probe as described above may not be needed. In various embodiments, during the PCR extension step, a unique oligo probe may be cleaved by attack polymerase after completion of the PCR, the releasable oligo probe may be hybridized to a capture anti-sense oligo immobilized on the surface of the electrochemical detector. In various embodiments, the oligo probe which can be hybridized to a surface of the electrochemical detector may generate a yes answer and lack of hybridization may generate a no answer for the target related to a pathogen or virus for which it is being analyzed. In various embodiments, such a handheld may be able to multiplex several targets by designing a multiple of unique probes that may hybridize to a unique detector thus providing a yes/no answer for each of multiple targets for a group of pathogens or viruses being analyzed. Examples of use of DNA amplification assay employing electrochemical detection may be found in U.S. Provisional Patent Application No. 60/699,950, filed Jul. 7, 2005 and commonly assigned.

Figure 14:
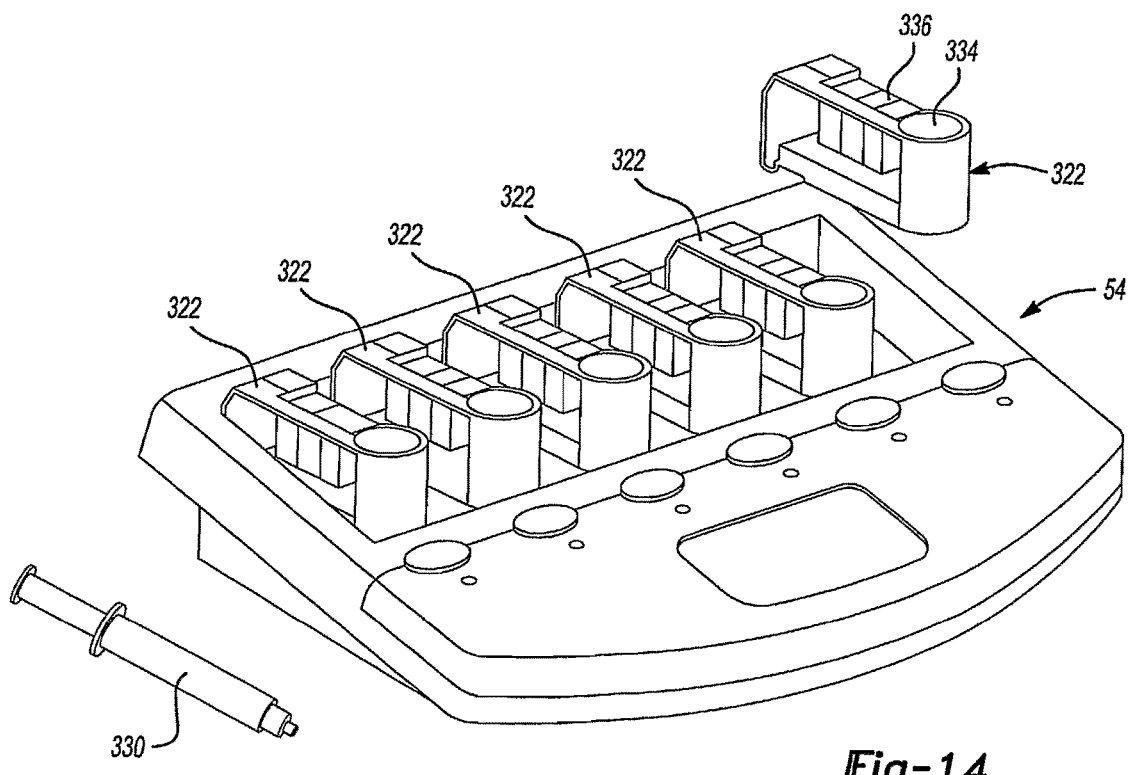
FIG. 14 illustrates a multiple cartridge portable medical device.

An example of a portable reader-analyzer instrument 54 is illustrated in FIG. 14 as an exemplary device. In various embodiments, portable instrument 54 can utilize six fluidic cartridges 322. The portable instrument 54 can be capable of analyzing a variety of different sample types. In various embodiments, it may be powered using AC power from a standard outlet, or by battery power, or by solar power. Further, the portable instrument 54 can have no processing ability, relying instead on connection to, and control by, a computer. This computer can be a laptop, so not to limit the portability of the portable instrument 54. In various embodiments, the portable instrument 54 can be configured to detect on the order of ten strains of bacteria or virus (although smaller and larger numbers of strains are also possible).

In various embodiments, the portable instrument 54 employs up to approximately 50 detection wells and can be capable of analyzing multiple samples per run. In various embodiments, portable instrument 54 can be configured to perform multiplex PCR (as discussed above) in at least one pre-filled reagent cartridges 336. For example, with 50 detection wells, five patient samples could be analyzed for ten agents each. One or more of the agents can be controls, which are used to calibrate the portable instrument. Calibration is discussed in more detail below. FIG. 15 illustrates a cutaway view of a fluidic cartridge 322, including a cartridge housing 338, a flexible printed circuit board (PCB) interconnect 332, a sample inlet 334 for a 5 mL syringe 330, and pre-filled reagent cartridges 336. In various embodiments, portable instrument 54 may perform PCR utilizing electrochemical detection.

Figure 16:
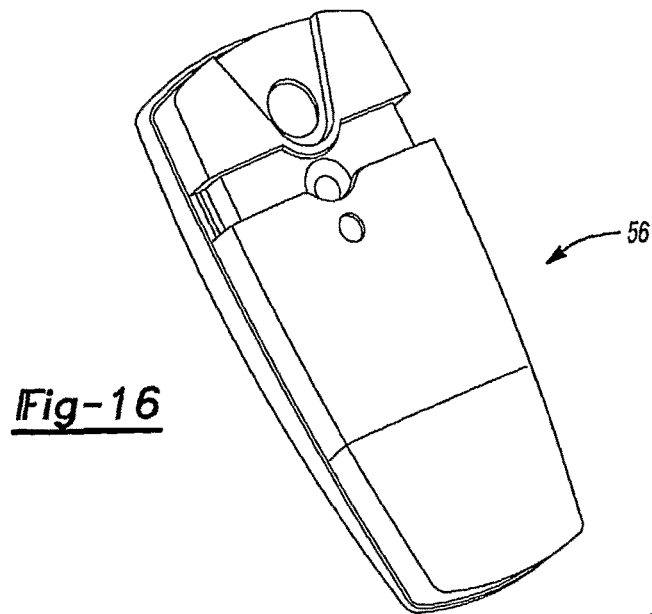
FIG. 16 is a perspective view of a handheld reader-analyzer instrument.

FIG. 16 shows a handheld instrument 56. The handheld instrument 56 can be configured to analyze a single sample per run. For example, this sample can be a sputum sample from a patient. The handheld instrument 56 can be pocket-sized or about the size of a deck of playing cards to allow for easy storage and portability. To this end, the processing ability of the handheld instrument 56 may be limited, relying on externally located resources for more sophisticated analysis.

The handheld instrument 56 can be configured to detect multi-drug-resistant tuberculosis, a very useful application in developing countries. The handheld instrument 56 may be capable of running on batteries for situations where electrical power may be not present or may not be reliable. An internal controller can automatically coordinate transfer of data acquired by the handheld instrument 56 to another device for further analysis such as P2P communication to another handheld instrument 56, a portable instrument 54, a laboratory instrument 52, a local computer, a network, or a distant server. Such communication may be wired, wireless, or a combination thereof. In various embodiments, handheld instrument 56 may include a GPS device to identify the location of the where the sample was analyzed and such resulting spatial data can be communication along with PCR results for further analysis.

Figure 17:
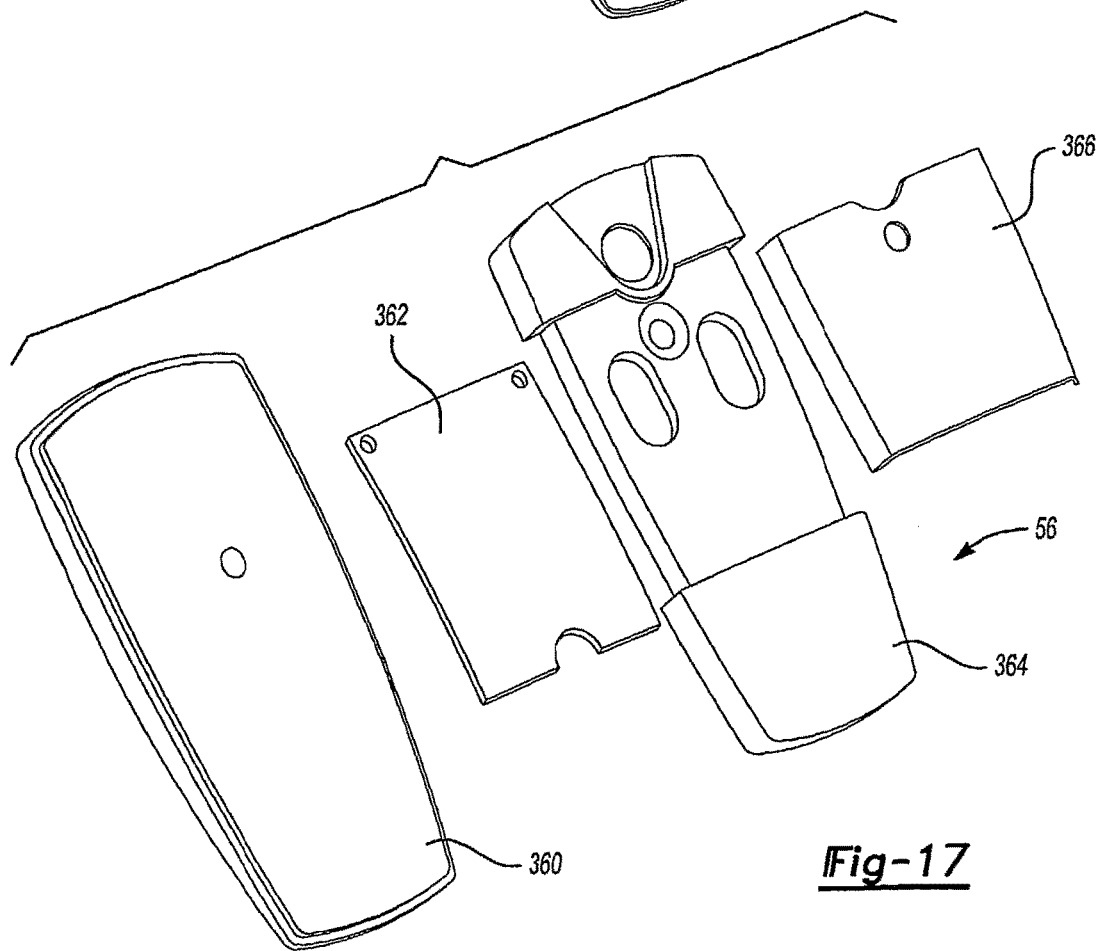
FIG. 17 is an exploded view of a handheld reader-analyzer instrument.
Figure 18:
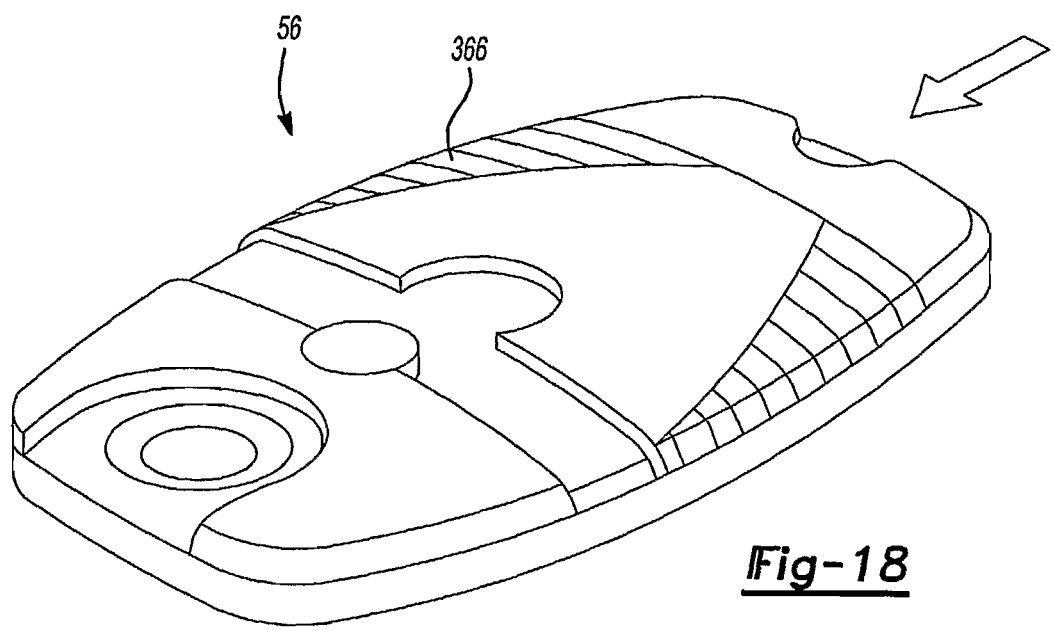
FIG. 18 illustrates an activation of a handheld reader-analyzer instrument for an analysis.
Figure 19:
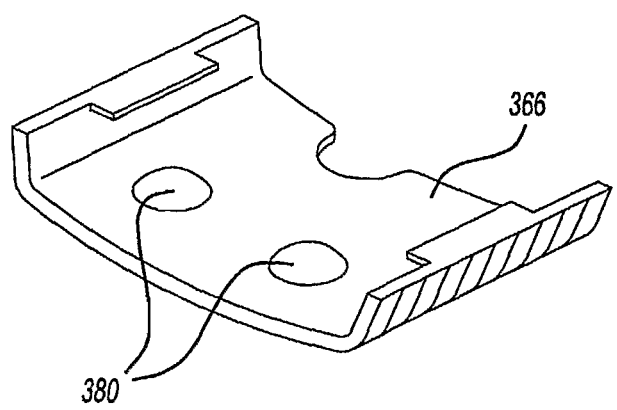
FIG. 19 is a perspective view of the inside of an activation slider of a handheld reader-analyzer instrument.

Referring to FIG. 17, components of handheld instrument 56 can include an enclosure back 360, microfluidic device 362, an enclosure front 364, and an activation slider 366. FIG. 18 demonstrates the activation of the handheld instrument 56 by sliding the activation slider 366 in the direction of the arrow toward the top of the handheld instrument 56. FIG. 19 demonstrates protusions 380 on the inside of the activation slider 366 that activate the PCR process. In various embodiments, handheld instrument 56 can be preloaded with PCR reagents. In various embodiments, handheld instrument 56 may perform PCR utilizing electrochemical detection, as discussed above.

Although not specifically illustrated, each of the above reader-analyzer instruments 176 can be provided with a visual readout. This readout can be used to display operating instructions or messages to the user, including alert messages about tests that should be performed on the reader-analyzer instrument 176. Such messages would be provided using the communication capability of the instrument. In various embodiments, reader-analyzer instrument 176 can include a MMI such as, for example, a keyboard. The MMI may be useful for entering spatial and/or demographic data, and/or confirming each step performed during an analysis, and/or to communicate with the network, a computer or another reader-analyzer instrument 176. In various embodiments, the MMI can be a computer in bi-directional communication with reader-analyzer instrument 176. In various embodiments, cellular phone capabilities may be included in the reader-analyzer instrument 176. In various embodiments, the reader-analysis instruments 176 utilize a common genetic assay analysis platform, such as a TaqMan® assay-based platform, as discussed herein, which utilizes PCR techniques. A collection 102 of reader-analyzer instruments 176 may include other types of analysis platforms can additionally or alternatively be used, such as, for example, hybridization array (microarray) platforms. In some applications, it may be beneficial to utilize both hybridization array and PCR platforms together. For example, a hybridization array technology can be employed first to screen a sample over a large number of different targets (e.g., different bacteria, viruses, pathogens, and/or other target sequences).

In various embodiments, the results of the initial hybridization array analysis can then indicate a PCR analysis to select for subsequent testing. As will be more fully explained herein, the reader-analyzer instruments 176 can be equipped with bidirectional communication capability such as P2P or through a network, and this communication capability can be utilized, for example, to send control instructions and/or data from a hybridization array system to the PCR system, so that the PCR system will know, as identified by hybridization array system, what specific bacteria, virus, pathogen, and/or target sequence to target.

Environmental samplers 60, 62, such as, for example, air sampler 60 and water sampler 62, can be used. In various embodiments, data collected from any environmental samples can be included in the spatial data that is uploaded to the system 10. In various embodiments, these environmental samplers 60, 62 can simply be a front-end to the PCR process detailed above, containing an apparatus to capture a sample, and suspend it in solution for processing by an ISAP module 172. In various embodiments, the samplers 60, 62 can include specific PCR instruments designed to perform PCR analysis on environmental samples. Similarly, PCR can be employed in medical diagnostics, environmental studies, clinical studies, food/agricultural analysis, animal/organism testing, and chemical content analysis.

In various embodiments, PCR can be adapted to perform quantitative PCR. In various embodiments, two different methods of analyzing data from PCR experiments can be used: absolute quantification and relative quantification. In various embodiments, absolute quantification can determine an input copy number of the target DNA of interest. This can be accomplished by relating a signal from a detection probe to a standard curve. In various embodiments, relative quantification can describe the change in expression of the target DNA relative to a reference or a group of references such as, for example, an untreated control, an endogenous control, a passive internal reference, a universal reference RNA, or a sample at time zero in a time course study. When determining absolute quantification, the expression of the target DNA can be compared across many samples, for example, from different individuals, from different tissues, from multiple replicates, and/or serial dilution of standards in one or more matrices.

In various embodiments of the present teachings, PCR can be performed using relative quantification and the use of standard curve may not be required. Relative quantification can compare the changes in steady state target DNA levels of two or more genes to each other with one of the genes acting as an endogenous reference, which may be used to normalize a signal from a sample gene. In various embodiments, in order to compare between experiments, resulting fold differences from the normalization of sample to the reference can be expressed relative to a calibrator sample. In various embodiments, the calibrator sample can be included in each sample well of the assay panel. The analysis system can determine the amount of target DNA, normalized to a reference, by determining $$\Delta C_T = C_{Tq} C_{Tendo}$$

where $C_T$ is the threshold cycle for detection of a fluorophore in real time PCR; $C_{Tq}$ is the threshold cycle for detection of a fluorophore for a target DNA in sample; and $C_{Tendo}$ is the threshold cycle for detection of a fluorophore for an endogenous reference or a passive internal reference in assay. In various embodiments, a gene expression analysis system can determine the amount of target DNA, normalized to a reference and relative to a calibrator, by determining:

$$\Delta\Delta C_T = \Delta C_{Tq} - \Delta C_{Tcb}$$

where $C_{Tq}$ is the threshold cycle for detection of a fluorophore for the target DNA in sample; $C_{Tcb}$ is the threshold cycle for detection of a fluorophore for a calibrator sample; $\Delta C_{Tq}$ is a difference in threshold cycles for the target DNA and an endogenous reference; and $\Delta C_{Tcb}$ is a difference in threshold cycles for the calibrator sample and the endogenous reference If $\Delta\Delta C_T$ is determined, the relative quantity of the target DNA can be determined using a relationship of relative quantity of the target DNA, which can be equal to $2^{-\Delta\Delta C_T}$. In various embodiments, $\Delta\Delta C_T$ can be about zero. In various embodiments, $\Delta\Delta C_T$ can be less than ±1. In various embodiments, the above calculations can be adapted for use in multiplex PCR (See, for example, Livak et al. Applied Biosystems User Bulletin #2, updated October 2001, and Livak and Schmittgen, Methods (25) 402-408 (2001). In various embodiments, once calibration has been performed on all target sequence $C_T$ values to produce their respective copy numbers, the data can be analyzed in various ways.

A knowledge base comprises a set of sentences (or rules, etc.) that assert something about the context within which they exist. For example, in the real-time PCR context, asserting that "a $C_T$ value less than twenty for a target sequence X means the target sequence level of X is high" is an application of knowledge that originates from data in the EpiMonitor domain. The knowledge being represented in this example is when a target sequence level is high. Knowledge base construction involves structuring the domain so that knowledge-creating methods or rules, which end users may devise, provide a framework for inference.

In various embodiments, a rules engine is described to flexibly create and process rules to apply a qualitative label or labels to quantitative results. Rules may be defined a priori by a user, or determined by the rules engine based upon a learning algorithm. A simple example of a rule is the application of a PLUS label when a $C_T$ value is less than 30 and a MINUS label when the $C_T$ value is greater than or equal to 30. Such a simple inequality may not fully encapsulate the logical procedure a skilled user would undertake to reach a qualitative result. For example, a user can perform other evaluations related to real-time PCR experiments to reach the conclusion that a PLUS label is appropriate. These evaluations include assessing data validity by looking at reaction controls, using quality control (QC) metrics to determine reproducibility, and looking at the $C_T$ data to see if the value falls within an expected numerical range.

Each of the steps in the process can be defined using first-order logic to automate the application of a qualitative label to quantitative data. This definition can be achieved by codifying each of the process steps as a Rule composed of Statements, building a ruleset that is a series of these rules, and examining the data against the ruleset (instantiation). Additional logical steps can be performed in the form of a decision tree or a forward- or backward-chaining program.

In various embodiments, a Pathogen Calculator software tool can implement such a rules engine, which can apply a label of high, medium, or low to PCR data. Additionally, error labels such as invalid, unrepeatable, or out of bounds can be applied. A label of invalid can be applied if measurement of reaction controls indicates a failure occurred in the reaction process. A label of unrepeatable can be applied if the data does not meet QC metrics, such as records of time and temperature recorded by the instrument performing PCR. A label of unrepeatable can also be applied if statistical parameters of the data, such as standard deviation, are outside of permissible boundaries. A label of out of bounds can be applied if the $C_T$ value is less than a lower limit, indicating too much fluorescence (or other indicator) at too early a stage, and thus invalid data. The label of out of bounds can also be applied if the $C_T$ value is too great, indicating a result beyond the accepted resolution of the instrument.

The Pathogen Calculator tool can define certain thresholds based upon the sample card 174 configuration to flag percentages, quantities, and/or qualitative results. Threshold violations and other results, whether qualitative or quantitative, can be demonstrated graphically to the user. In various embodiments, the Pathogen Calculator includes a percentage calculator that can be used to determine respective quantities of the various target sequences present. The target sequence percentage can be calculated by dividing the copy number of a selected target sequence by the sum of all target sequence copy numbers, then multiplied by 100%. This information can be displayed in various ways, including tables and bar charts. In various embodiments, the Pathogen Calculator tool may be implemented within one of the reader-analyzer instruments 176, or within a computer in communication with the reader-analyzer instrument 176. Data, qualitative or otherwise, that is generated by the Pathogen Calculator can be communicated to the EpiMonitor software platform 100, instead of, or in addition to, the reaction data. In various embodiments, the Pathogen Calculator can be located in a reader-analyzer instrument 176, or in a computer associated with a reader-analyzer instrument 176. The Pathogen Calculator can also be implemented in the EpiMonitor software platform 100 itself.

Because $C_T$ values may vary based upon a number of factors, including the reader-analyzer instrument 176 platform type, the assay type, and the genetic material sample type, a rules engine can take these factors into account. For instance, different rulesets can be defined for each platform, such as one ruleset for a BioRad LightCycler, and another for an ABI 7900. Within each platform ruleset, there can be groups of rules for each sample type, such as blood, sputum, hair, dirt, saliva, etc. Each group of sample type rules can contain individual rules for each assay type, such as a particular manufacturer's primer/probe set used for detecting *bordetella pertussis*. This linear model can be extrapolated to greater or fewer numbers of factors.

Other rules may be included for each individual target sequence, for example, different target sequences out of each of two pathogenic *E. coli* strains, such as O127:H7 and O157:H7. Still other rules can include normalizing to a variety of different endogenous controls that can be used in individual assays. Combinations of all or a subset of these rules can be used in various embodiments. Standardized chemistry and controls can be used to help limit the amount of rules to a manageable number.

In various embodiments, hierarchical rules can be defined. For example, a ruleset can be defined for platform type, a ruleset can be defined for sample type, and a ruleset can be defined for assay type. These rulesets can then be applied serially. For example, rules within the platform type ruleset can be applied based upon the type of platform used to acquire PCR data. Then rules within the sample type ruleset can be applied based upon the type of sample from which genetic information was extracted. Then rules within the assay type ruleset can be applied based upon the assay type, for example, controls, PCR chemistry, probes, etc.

In various embodiments, a global ruleset can be defined that operates on normalized values, whether normalized $C_T$ values, normalized copy count numbers, or other suitable values. Normalization, as described below, can account for variations in factors such as platform type, sample type, and assay type. Then a global ruleset can be applied equally to the normalized numbers, regardless of platform, sample type, assay type, etc.

The following exemplary XML (extensible markup language) code demonstrates a data structure containing rules that can be passed to the Pathogen Calculator. This data structure can be stored within the EpiMonitor platform 100 or communicated to reader-analyzer instruments 176. These rules can be used by the Pathogen Calculator to qualitatively label quantitative results from a real-time PCR run.

```
<?xml version="1.0" ?>
- <qualresult type="linearrulesresult">
    - <linearrulesresult owner ="B-pert" sample_name="Sample01" description="General Linear Evaluation">
        - <rulesresult owner ="B-pert" sample_name="Sample01" description="Poor Replicate Data Quality" true_result="Pathogen QC: Fail" false_result="ok" true_color="205,92,92" false_color="152,251,152" operators="NONE">
            - <rule owner ="B-pert" sample_name="Sample01" operators="AND" datatype="StdDev(Ct)">
                <statement operator="GREATER THAN" value="2" />
                <statement operator="NOT EQUAL" value="NaN" />
              </rule>
          </rulesresult>
        - <rulesresult owner ="B-pert" sample_name="Sample01" description="Low Pathogen Quality" true_result="low" false_result="not low" true_color="152,251,152" false_color="205,92,92" operators="NONE">
            - <rule owner ="B-pert" sample_name="Sample01" operators="OR" datatype="Mean(Ct)">
                <statement operator="GREATER THAN" value="35" />
                <statement operator="EQUAL" value="NaN" />
              </rule>
          </rulesresult>
        - <rulesresult owner ="B-pert" sample_name="Sample01" description="Medium Pathogen Quality" true_result="medium" false_result="not medium" true_color="238,221,130" false_color="152,251,152" operators="NONE">
            - <rule owner ="B-pert" sample_name="Sample01" operators="AND" datatype="Mean(Ct)">
                <statement operator="LESS THAN" value="35" />
                <statement operator="GREATER THAN" value="25" />
              </rule>
          </rulesresult>
        - <rulesresult owner ="B-pert" sample_name="Sample01" description="High Pathogen Quality" true_result="high" false_result="not high" true_color="238,92,66" false_color="152,251,152" operators="NONE">
            - <rule owner ="B-pert" sample_name="Sample01" operators="AND" datatype="Mean(Ct)">
                <statement operator="LESS THAN" value="25" />
              </rule>
          </rulesresult>
      </linearrulesresult>
  </qualresult>
```

This data structure defines a decision tree type of analysis for the B-pert assay for a sample named Sample01. Each rule is evaluated in order until a true result is found. The first rule defines "Poor Replicate Data Quality." This rule states that the replicate data is poor when this target sequence's standard deviation of $C_T$ is greater than 2 and not equal to "NaN." When true, the rules engine will return the qualitative result "Pathogen QC: Fail," which denotes a failure in the real-time PCR.

The second rule defines a "Low Pathogen Quantity," which is present when an arithmetic mean of $C_T$ values is greater than 35 or equal to "NaN." This will return a qualitative result of "Low" when true. The third rule defines a "Medium Pathogen Quantity," which is expressed by a mean($C_T$) less than 35 and greater than 25. This will return a qualitative result of "Medium" when true.

The last rule is a "High Pathogen Quantity," which is expressed by a mean $C_T$ value less than 25. This will return a qualitative result of "High" when true. This example demonstrates how knowledge of assay parameters can be codified, in this case knowledge of the *Bordetella pertussis* assay, and what sorts of qualitative results can be generated.

A ruleset data structure can be encoded to be easily readable by both humans and computer programs such as by using XML, as demonstrated above. Such a ruleset may be coded in any machine-readable language. In addition to the qualitative results returned by the decision tree, each rule can return other types of data such as strings (in this case, these rules also return text indices for RGB color in order to give a color representation along with the qualitative result), other rules, or other sets of rules.

Normalization allows data to be compared without regard to systematic variations. Such systematic variations include differences between platforms, between different sample types, and between different assay types. Each machine that performs PCR may have slightly different operating parameters, and differences between manufacturers may be even greater. Various sample types entail differences in the difficult of purifying the nucleic acid content in the sample, whether and to what extent PCR inhibitors are present, and quantity of nucleic acid per volume. Different assay types produce different reaction rates, and each may interact with a sample differently. The linear rules engine model described above is one approach to normalization. By generating a qualitative tag for each set of reaction data, disparate reaction data can be compared, regardless of PCR platform, symptoms, illness, etc. The normalization is accomplished by having rules specifically tailored to each combination of variable, such as assay X, taken on instrument Y, originating from sample Z.

Quantitative normalization is also possible. One approach is to convert $C_T$ to a genomic copy number. This conversion can be accomplished through the use of absolute or relative quantitation. Relative quantitation relies on comparing the fluorescence (or other indicia) of probes for the target sequence of interest to fluorescence (or other indicia) of probes for a genetic standard within the same reaction well. This standard can be genetic data assumed to be present in substantially consistent quantity (such as GAPDH, discussed below), or added to the sample. Absolute quantitation relies on forming a standard curve for an assay via a dilution series prepared a priori. The dilution series records fluorescence (or other indicia) data (often measured by $C_T$) at various starting copy numbers of the target sequence of interest. Then, a linear best fit is determined for $C_T$ vs. the logarithm (such as base 10) of copy number, yielding a line described by a slope and y-intercept. Unknown $C_T$s (those measured in the field) can be converted to copy number by interpolating the value from this line.

Each PCR assay and instrument platform can be described by standard curve parameters that convert threshold cycle to copy number. This copy number is then comparable across assays and instrument platforms. Copy number can further be normalized against sample type by adjusting to a standard sample type, such as blood. A similar procedure could be used, wherein levels of known genetic sequences are measured within each of the various sample types, such as blood and sputum. A correlation, such as a best-fit line, can then be fitted to the plot of copy number of each sample type of interest to copy number of the standard sample type. In various embodiments, triple delta $C_T$, or delta delta $C_T$, described below, can be used to normalize reaction data in the gene expression domain.

Benefits of normalization can include, for example, system 10 is not reliant on just one or two types of reader-analyzer instruments 176, or reader-analyzer instruments 176 exclusively from one manufacturer, or using one type of chemistry. Such benefits allow EpiMonitor software platform 100 to encompass a greater universe of reader-analyzer instruments 176 without additional capital expenditures or major instrument replacement, and thus allows for a greater quantity of data to be captured and participation of a larger group of labs.

Figure 20:
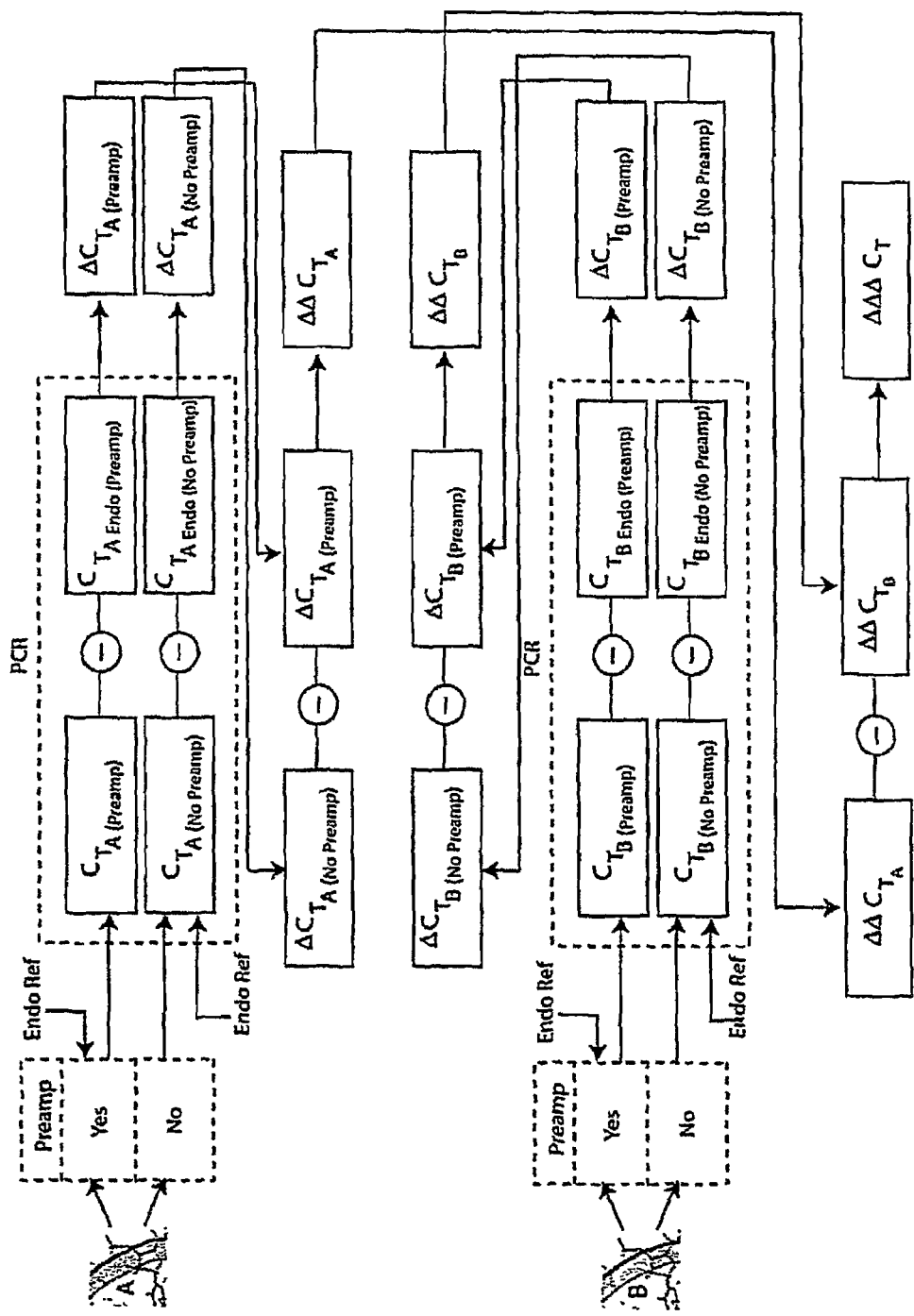
FIG. 20 is a flowchart illustrating a triple delta calculation.

In various embodiments of the present teachings, an analysis system can use $\Delta\Delta C_T$ values computed for the same target DNA but in different samples (Sample A ($S_A$) and Sample B ($S_B$)) in order to determine the accuracy of subsequent relative expression computations. This results in the equation as shown in FIG. 20, $$\Delta\Delta\Delta C_T T_x = \Delta\Delta C_T T_x S_A - \Delta\Delta C_T T_x S_B$$

In various embodiments, a value for $\Delta\Delta\Delta C_T T_x$ can be zero, or reasonably close to zero, which can indicate that the preamplified $\Delta C_T$ values for $T_x$ ($\Delta C_{T\ preamplified}\ T_x S_A$ and $\Delta C_{T\ preamplified}\ T_x S_B$) can be used for relative gene expression computation between different samples via a standard relative gene expression calculation. Such calculation may be useful in normalizing data from different instruments 176 or as a QC step to accept or reject normalized data.

In various embodiments, a standard relative gene expression calculation can determine the amount of the target DNA. In various embodiments, a standard relative gene expression calculation employs a comparative $C_T$. In various embodiments, the above methods can be practiced during experimental design and once the conditions have been optimized so that the $\Delta\Delta\Delta C_T T_x$ is reasonably close to zero, subsequent experiments only require the computation of the $\Delta C_T$ value for the preamplified reactions. In various embodiments, $\Delta\Delta C_T T_x S_A$ values can be stored in a database or other storage medium. In various embodiments, these values can then be used to convert $\Delta\Delta C_{Tpreamplified} T_x S_A$ values to $\Delta\Delta C_{T\ not\ preamplified} T_x S_A$ values. In various embodiments, the $\Delta\Delta C_{T\ preamplified} T_x S_y$ values can be mapped back to a common domain. In various embodiments, a not preamplified domain can be calculated using other gene expression instrument platforms such as, for example, a microarray. In various embodiments, the $\Delta\Delta C_T T_x S_A$ values need not be stored for all different sample source inputs ($S_A$) if it can be illustrated that the $\Delta\Delta C_{T\ preamplified} T_x$ is reasonably consistent over different sample source inputs.

In various embodiments, microarray technology, which can provide data to system 10. In various embodiments, a microarray can be a piece of glass or plastic on which single-stranded pieces of DNA are affixed in a microscopic array as probes. In various embodiments, thousands of identical probes can be affixed at each point in the array which can make effective detectors.

Typically, arrays can be used to detect the presence of mRNAs that may have been transcribed from different genes and which encode different proteins. The RNA can be extracted from many cells, ideally from a single cell type, then converted to cDNA. In various embodiments, the cDNA may be amplified in quantity by PCR. Fluorescent tags can be enzymatically incorporated into the or can be chemically attached to strands of cDNA. In various embodiments, a cDNA molecule that contains a sequence complementary to one of the probes will hybridize via base pairing to the point at which the complementary probes are affixed. In various embodiments, the point on the array can then fluoresce when examined using a microarray scanner. In various embodiments, the intensity of the fluorescence can be proportional to the number of copies of a particular mRNA that were present and calculates the activity or expression level of that gene.

In various embodiments, a microarray can be, for example, a cDNA array, a hybridization array, a DNA microchip, a high density sequence oligonucleotide array, or the like. In various embodiments, a microarray can be available from a commercial source such as, for example, Applied Biosystems, Affymetrix, Agilent, Illumina, or Xeotron. In various embodiments, a microarray can be made by any number of technologies, including printing with fine-pointed pins onto glass slides, photolithography using pre-made masks, photolithography using dynamic micromirror devices, or ink-jet printers. The lack of standardization in microarrays can present an interoperability problem in bioinformatics since it can limit the exchange of array data.

In various embodiments, microarray output data can be in a format of fluorescence intensity and in various embodiments, microarray output data may be in a format of chemiluminescence intensity. In various embodiments, an intensity value from a microarray output data can be globally normalized. In various embodiments, total difference values can be determined by subtracting background noise and normalizing the array signal intensity, then dividing experimental sample signal intensity by a control sample signal intensity yielding net sample intensity. In various embodiments, a control sample used to generate the control sample signal intensity can be, for example, Stratagene®, UHR, or the like. In various embodiments, a total difference can be converted to a $\log_2$ by the following equation:

$$2^{\Delta\Delta C_T} = 3.3 \log_{10}(\text{net intensity sample 1/net intensity sample 2})$$

In various embodiments, microarray output data is in a $\Delta\Delta C_T$ format. In various embodiments, microarray output data can be converted into a $\Delta\Delta C_T$ format by the following equation:

$$R = (\tfrac{1}{2})^{\Delta\Delta C_T}$$

where R is the resulting measurement from a microarray. Such calculations are available commercially, such as GeneSpring from Silicon Genetics. Various embodiments include converting microarray output data into a $\Delta\Delta C_T$ format using a Global Pattern Recognition (GPR) algorithm which can convert intensity values generated from microarrays from linear values to algorithmic values and can use transformed intensity cutoffs to affect gene and normalizer filters. In various embodiments, GPR software algorithm may be available from The Jackson Laboratory. In various embodiments, microarray output data can be in a standard language or format such as MAGE-ML (microarray and gene expression markup language), MAML (microarray markup language), or MIAME (minimum information about microarray experiments). In various embodiments, such standardized formats and language can be converted to a $\Delta\Delta C_T$ format.

Figure 21:
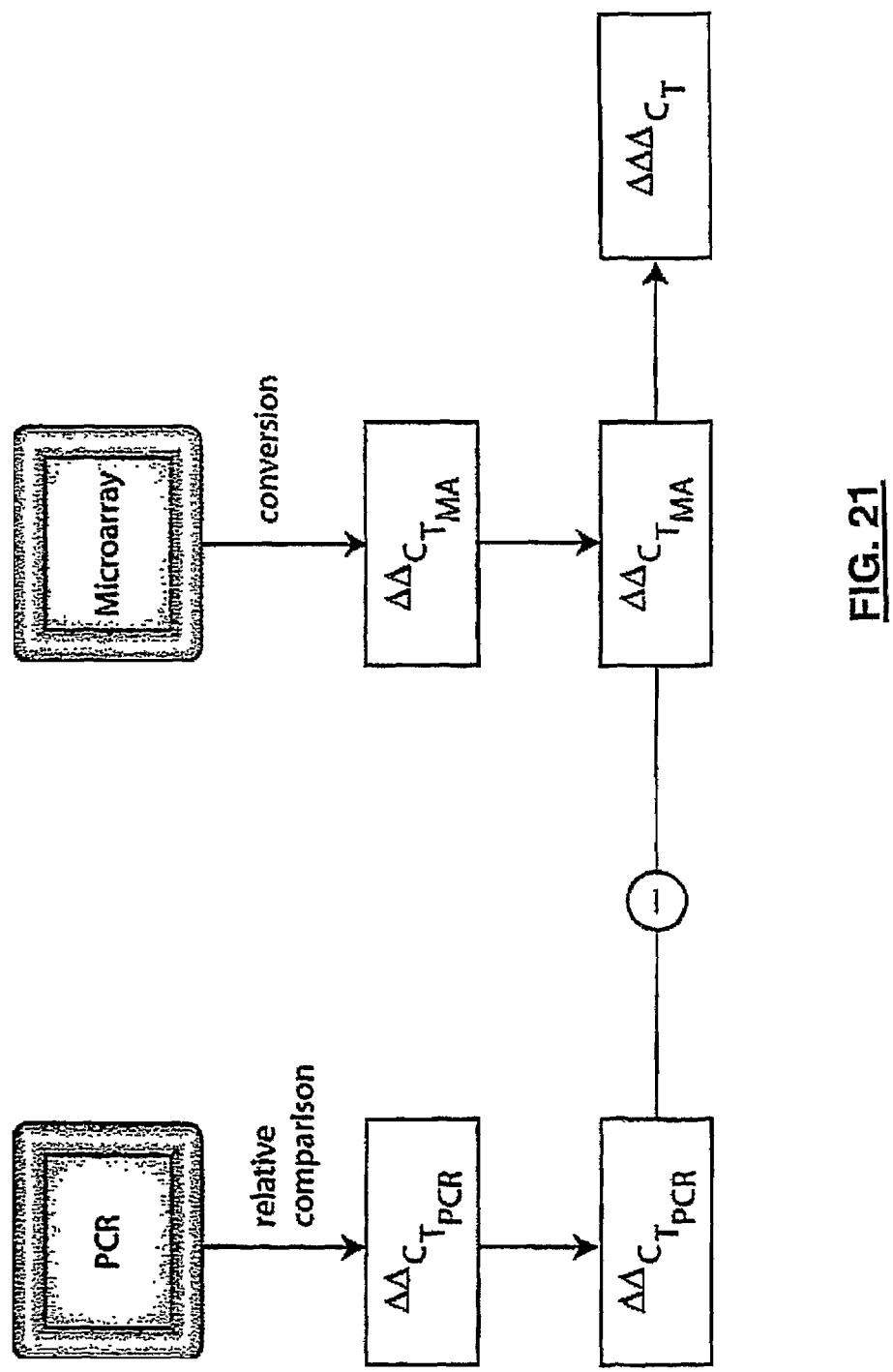
FIG. 21 is a flowchart illustrating a triple delta calculation using PCR and microarray generated data sets.

In various embodiments, microarray output data can be in a $\Delta\Delta C_T$ format, then PCR data can be directly compared to data from microarray platforms as shown in FIG. 21. In various embodiments, a $\Delta\Delta\Delta C_T$ calculation can be a validation tool to confirm that relative quantitation data can be compared from one amplification/detection process to another. In various embodiments, $\Delta\Delta\Delta C_T$ calculation can be a validation tool to confirm that relative quantitation data can be compared from one sample input source to another sample input source, for example, comparing a sample from liver to a sample from brain in the same individual. In various embodiments, $\Delta\Delta\Delta C_T$ calculation can be a validation tool to confirm that relative quantitation data can be compared from one high-density sequence detector system to another high-density sequence detection system.

In various embodiments, $M\Delta C_T$ calculation can be a validation tool to confirm that relative quantitation data can be compared from one platform to another, for example, data from real time PCR to data from a hybridization array is especially valuable for cross-platform validation. In various embodiments, real-time PCR and hybridization array data can be directly compared. In various embodiments, a Taq-Man® $\Delta\Delta C_T$ can be compared to a microarray output converted to the $\Delta\Delta C_T$ format. In various embodiments, the resultant $\Delta\Delta\Delta C_T$, if within +/−1 $C_T$ of zero, can determine a high-degree of confidence that the actual total difference observed within each of the two platforms is correlative and, as such, may be normalized for entry into system 10. Further discussion of $\Delta\Delta\Delta C_T$ can be found in commonly assigned U.S. patent application Ser. No. 11/086,253.

In various embodiments, a correction, which can be a quantity added to a calculated or observed value to obtain the true value, may be used so that data generated on two different platforms can be used together in further calculations and analysis. Various embodiments allow for larger and sometimes more complete data sets to be used in gene expression studies. In various embodiments, the correction can be calculated from a resulting $\Delta\Delta\Delta C_T$. In various embodiments, a correction can be a bias correction.

Figure 22:
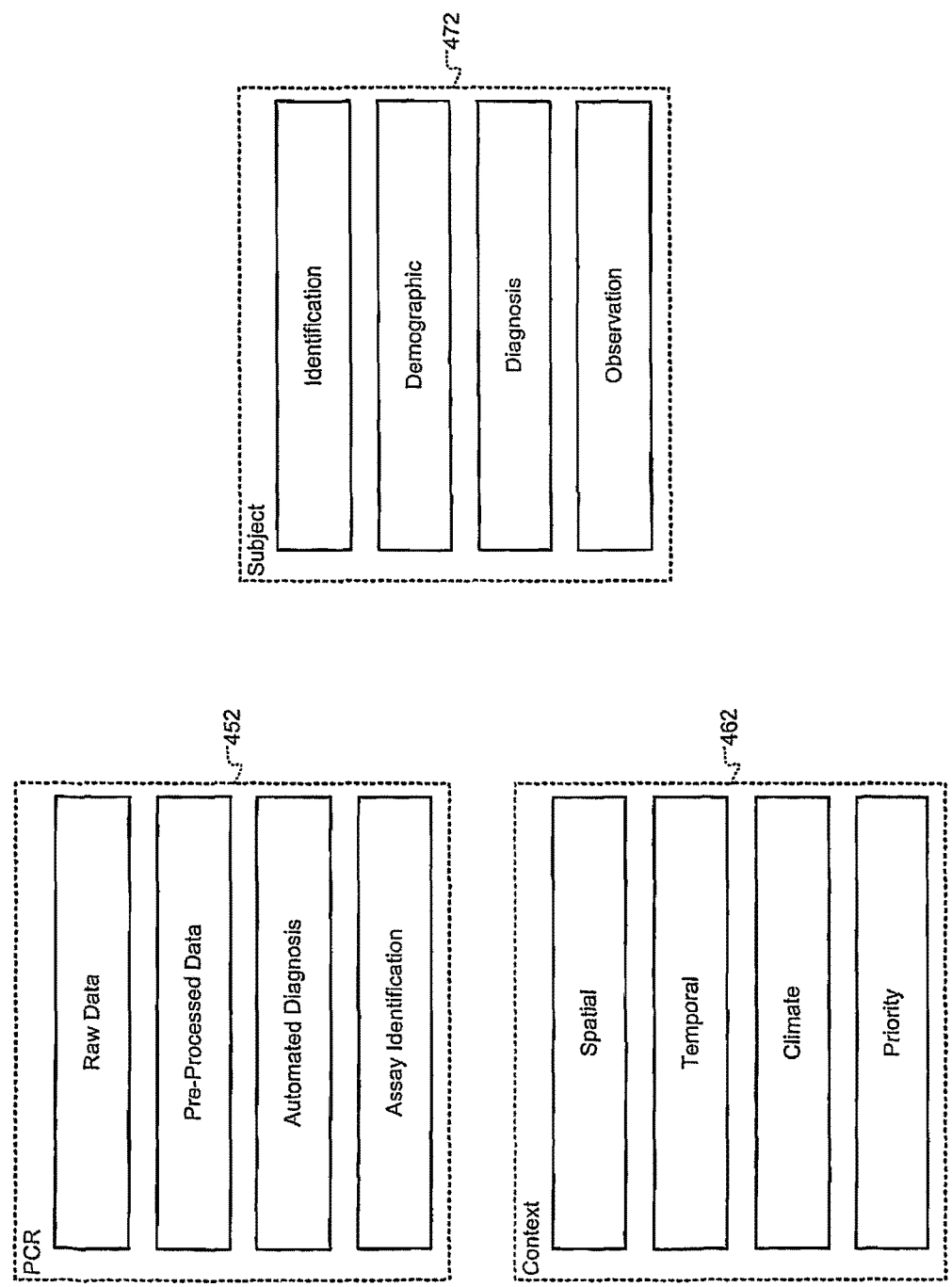
FIG. 22 is a graphical depiction of an example of a plurality of classes of information acquired and transmitted to the EpiMonitor platform.

Referring now to FIG. 22, a graphical representation illustrates some of the information that can be acquired and transmitted by the reader-analyzer instruments 176 to the EpiMonitor software platform 100. The reader-analyzer instruments 176 may provide PCR analysis results or other genetic data 452 to the EpiMonitor software platform 100. These analysis results can be in the form of raw data, can be pre-processed in some respect, or can even be a diagnosis (such as a determination that the patient is infected with a particular illness). Pre-processing possibilities are discussed in greater detail below.

EpiMonitor software platform 100 can also store an identifier for each assay performed on a sample as part of the PCR analysis results or other genetic data 452. This can be based upon Logical Observation Identifiers Names and Codes (LOINC), a standard that codifies laboratory and clinical observations and can be applied by the EpiMonitor administrator when creating a panel and a probe (see below).

Reader-analyzer instruments 176 can also capture contextual information 462, including spatial, temporal, climate, and priority information. Spatial (e.g., geographic) information describes where the sample was obtained, where the sample was prepared for processing, and/or where the sample analysis was performed. When analyzing genetic material of an entire population (whether of a community, a country, the world, etc.), this spatial component is useful for such purposes as analyzing how a target sequence is spreading through a population.

Spatial information can be provided by a user (including the patient or clinician) or automatically by the reader-analyzer instrument 176. In various embodiments, the reader-analyzer instrument 176 includes a system for ascertaining its geographic or spatial position. This can be provided by a GPS (Global Positioning System) device that is either embedded in, or in communication with, the reader-analyzer instrument 176. Additionally, the location of the reader-analyzer instrument 176 can be obtained by determining its IP (Internet Protocol) address and using a suitable lookup table to convert the IP address into a geographic location. While IP addresses are not uniformly accurate as indicators of physical location, the EpiMonitor software platform 100 can circumvent this limitation by requiring that the user or instrument register its geographic location once the instrument is connected to the communication network via the EpiMonitor software platform 100.

In addition to spatial information, temporal information can be retained for historical analysis. Reader-analyzer instruments 176 can synchronize their internal clocks with a reference clock of the EpiMonitor platform 100 to ensure accurate temporal information. As time-correlated historical data is accumulated, analysis can become increasingly powerful. For example, more thorough "baselines" can be collected to discern true signals from noise, and cyclical patterns may emerge that aid prediction or diagnosis.

Climate information can be useful to analyze results with regard to seasonal, weather, and/or pollution effects. Climate information includes temperature, humidity, precipitation, wind speed, and air quality. This information can be correlated with the temporal information to determine disease or other factors that might be more closely correlated with temperature than with season.

Priority level data can include information about conditions under which the reader-analyzer instrument 176 being used, as that information might be indicative of whether a positive detection of a particular bacteria, virus, pathogen or other target sequence should be used to trigger a public health warning or other action. In this regard, a positive detection from a single handheld instrument 56 might not warrant a public health alert; however, a single report from a laboratory instrument 52 associated with a reference laboratory or national laboratory might well warrant a public alert. The priority level data can be used to allow the laboratory response network 50 to interpret the reported information properly.

Subject information 472 can be recorded as well, and may include identification data, demographic data, diagnostic data, and clinical observations. Identification data, stored confidentially, is valuable for a number of reasons. A patient whose biological sample is later determined to contain a pathogen could be alerted to this fact. If the biological sample was taken from an animal, the animal may need to be quarantined or put down. If an infected patient visits multiple clinics or has multiple samples taken, it is useful to allow the system to identify that each of the samples came from the same subject. Any sample source can be recorded in the EpiMonitor software platform 100, including humans, animals, environmental samples, and plants. A population that can be analyzed on the EpiMonitor software platform 100 can be a group any living organism including plant for example filed of GMO crops. Identification information may differ for different types of sample sources, and such provision can be made in the database.

The Health Insurance Portability and Accountability Act (HIPAA) is the code of national standards for protecting the privacy of personal health information set forth by the U.S. Health and Human Services (HHS) department. In compliance with HIPAA, the EpiMonitor software 100 can store a unique key assigned to the patient by the clinician or physician. Certain applications, regulations, or privacy concerns may dictate that personal information not be obtained in particular circumstances. Demographic data, such as age and gender of the patient, can be stored. Correlating this data may lead to determinations of particular susceptibility of a certain age group or gender to a certain target sequence.

Diagnostic data includes information provided by the patient and information determined by the clinician by observing or analyzing the human or animal subject. In the case of a human subject, a chief complaint can be recorded. This is the complaint voiced by the patient and recorded by the clinician. The complaint can be coded by ICD-9 (International Classification of Diseases, ninth revision), a uniform code that can be used to tag each patient's syndrome or diagnosis (e.g., fever=12345, cough=12346, etc.), or can be stored as a physician's free text remarks (e.g., "fever," "cough," etc.). The physician's diagnosis of the patient can also be stored as an ICD-9 code or free text. Other storage possibilities are CPT (Current Procedural Terminology) code, commonly used for medical billing, and SNOMED (Systematized Nomenclature of Medicine) clinical terms.

To standardize input arriving as free text, natural language processing techniques can be used to convert free text into a code that can be used by a computer. For example, if the chief complaint reads "cough, sneezing, some fever," a text classifier can translate this into ICD-9 code 122.3 ("Respiratory Illness with Fever"). If samples are from plants and/or animals, observable characteristics can also be recorded. This can include, for instance, color, flowering patterns, yields, insect infestation, pesticide and/or herbicide application, and/or observed resistance to disease/pesticides.

Figure 23:
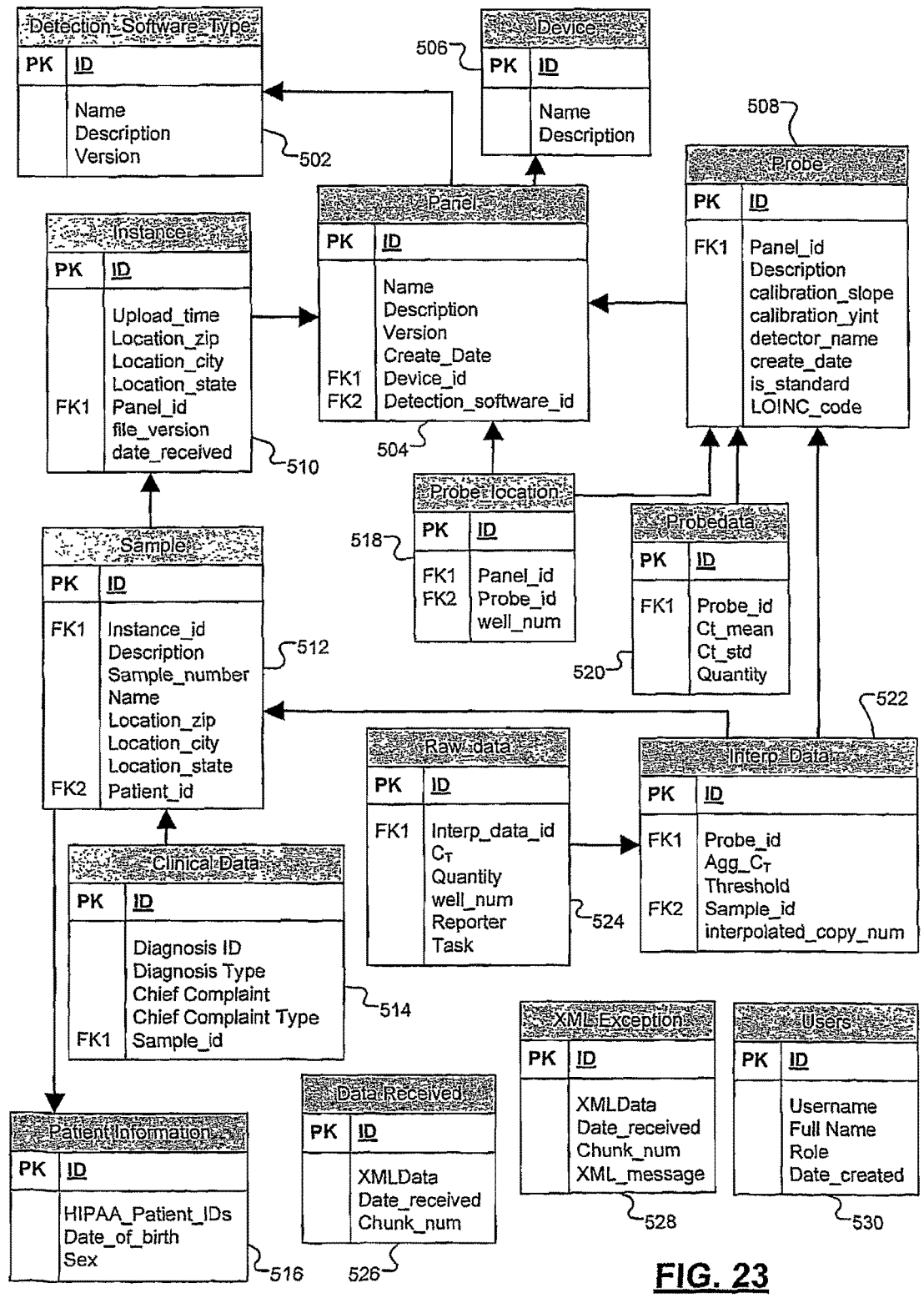
FIG. 23 illustrates a data structure and interaction of an exemplary database.

Referring now to FIG. 23, a database implementation capable of storing the above information is depicted. In the exemplary database implementation, a variety of interrelated tables can be used. These tables can include a Detection_Software_Type table 502 and a Panel table 504, which links to a Device table 506 and the Detection_Software_Type table 502. A Probe table 508 and a Probe_location table 518 link to the Panel table 504. An Instance table 510 also links to the Panel table 504. A Sample table 512 links to the Instance table 510 and to a Patient Information table 516. A Clinical Data table 514 and an Interp_Data table 522 link to the Sample table 512. A Raw_data table 524 links to the Interp_Data table 522. A Probedata table 520 and the Interp_Data table 522 link to the Probe table 508, A Data Received table 526, an XML Exception table 520, and a Users table 530 are unlinked.

The Data Received table 526 includes XMLData, Date_received, and Chunk_num. The XML Exception table 528 includes XMLData, Date_received, Chunk_num, and XML_message. The Users table 530 includes Username, Full Name, Role, and Date_created. The Detection_Software_Type table 502 includes Name, Description, and Version.

The Panel table 504 includes Name, Description, Version, Create_Date, Device_id, which links to the Device table 506, and Detection_software_id, which links to the Detection_Software_Type table 502. The Device table 506 includes Name and Description. The Patient Information table 516 includes HIPAA_Patient_IDs, Date_of_birth, and Sex. The Raw_data table 524 includes Interp_data_id, which links to the Interp_Data table 522, $C_T$, Quantity, well_num, Reporter, and Task.

The Interp_Data table 522 includes Probe_id, which links to the Probe table 508, Agg_$C_T$, Threshold, Sample_id, which links to the Sample table 512, and interpolated_copy_num. The Probedata table 520 includes Probe_id, which links to the Probe table 508, Ct_mean, Ct_std, and Quantity. The Probe_location table 518 includes Panel_id, which links to the Panel table 504, Probe_id, which links to the Probe table 508, and well_num. The Probe table 508 includes Panel_id, which links to the Panel table 504, Description, calibration_slope, calibration_yint, detector_name, create_date, is_standard, and LOINC_code.

The Clinical Data table 514 includes Diagnosis ID, Diagnosis Type, Chief Complaint, Chief Complaint Type, and Sample_id, which links to the Sample table 512. The Sample table 512 includes Instance_id, which links to the Instance table 510, Description, Sample_number, Name, Location_zip, Location_city, Location_state, and Patient_id, which links to the Patient Information table 516. The Instance table 510 includes Upload_time, Location_zip, Location_city, Location_state, Panel_id, which links to the Panel table 504, file_version, and date_received. The Panel table 504 includes Name, Description, Version, Create_Date, Device_id, which links to the Device table 506, and Detection_software_id, which links to the Detection_Software_Type table 502.

The Data Received table 526 and XML Exception table 528 serve as temporary data stores for XML uploads used for authentication and debugging. The Users table 530 contains the names of users allowed access to the system and the roles, or user access rights, that they have (discussed in more detail below). Mapping the data types of FIG. 23 to those adopted by other institutions, such as the Public Health Information Network (PHIN) allows others, such as the CDC, to incorporate EpiMonitor data into their analysis.

The EpiMonitor platform 100 allows users to log in to the system and define assay panels, configure individual gene probes, and view uploaded instances. Instance is the term used for the information related to the PCR analysis of a biological sample. A web interface provides a convenient and widely accessible mode of operation. In various embodiments, the EpiMonitor web interface includes a home page that provides a navigation index of other pages, including panels, probes, PCR devices, detection software types, and instances.

The home page can also display whether there are any identified outbreaks or system warnings. Statistics can also be displayed regarding timing of data uploads to the system, such as time of last upload, number of uploads for the current day, and total number of uploads. Clicking on the panel's link displays a list of currently defined panels. Clicking on one of the panels produces a "view panel" page. The information including the panel includes a description, a unique identifier, a version number, the number of wells per sample, the PCR detection software type (such as Sequence Detection Systems v. 2.2), the associated PCR device type, the date of panel creation, and the probes assigned to the panel. The view panel page can also display the uploaded instances that were based upon this panel.

A possible XML data structure that describes the panel is shown with exemplary data:

```
<?xml version="1.0" ?>
<panel id="3" description="Tony's Smaller Panel"
    device_name="7900" device_description="AB7900"
    software_name="SDS" software_version="2.2" version="1.0"
    wellspersample="48" create_date="2005-
    07-22 07:07:02">
    <probe id="9" name="B-pert" slope="-3.3547" yint="35.9770"
        description="Bordetella pertussis"
create_date="2005-07-22 07:07:02" is_standard="false" />
    <probe id="10" name="M-pneu" slope="-3.4563" yint="43.9540"
        description="Mycoplasma
pneumoniae" create_date="2005-07-22 07:07:02" is_standard="false" />
    <probe id="11" name="S-pneu" slope="-3.5956" yint="43.0410"
        description="Streptococcus
pneumoniae" create_date="2005-07-22 07:07:02" is_standard="false" />
    <probe id="12" name="IPC" slope="0" yint="0"
        description="Internal Positive Control"
create_date="2005-07-22 07:07:02" is_standard="true">
<probedata probeid="9" quantity="0.10" ctmean="27.6030"
ctstd="0.4180" />
<probedata probeid="9" quantity="1" ctmean="24.6630"
ctstd="0.2350" />
<probedata probeid="9" quantity="10" ctmean="21.0340"
ctstd="0.1840" />
    </probe>
</panel>
```

A subset of this data is transferred to the reader-analyzer instrument 176 so that it can accurately report back the PCR data. An Assay Information File (AIF) includes the sample name, detector, task (either a standard or an unknown), and copy number quantity (known a priori for standards) for each well of the microfluidic card 174. The first ten rows of an exemplary AIF are depicted in Table 3:

TABLE 3

| Well | Sample Name | Detector | Task | Quantity |
| --- | --- | --- | --- | --- |
| 1 | Sample01 | B-pert | UNKN | 0 |
| 2 | Sample01 | C-pneu | UNKN | 0 |
| 3 | Sample01 | L-pneu | UNKN | 0 |
| 4 | Sample01 | M-pneu | UNKN | 0 |
| 5 | Sample01 | C-botu | UNKN | 0 |
| 6 | Sample01 | S-pneu | UNKN | 0 |
| 7 | Sample01 | M-cata | UNKN | 0 |
| 8 | Sample01 | N-meni | UNKN | 0 |
| 9 | Sample01 | H-infl | UNKN | 0 |
| 10 | Sample01 | S-aure | UNKN | 0 |

In the database, each probe can be defined by a number of criteria. By clicking on one of the probes listed in the view panel page, a respective view probe page appears. The probe information includes a description, a unique identifier, a calibration slope and y-intercept, the detector name, whether the probe is a standard, and creation date. Probe data is stored to allow conversion from $C_T$ to copy number. This probe data can be stored and viewed in a table with columns for copy number (or quantity), mean value of $C_T$, and standard deviation of $C_T$. The view probe page can also display the panels that employ this probe.

The view instance page, which can be accessed from a listing of instances linked to from the home page, or from one of the instances listed in a view panel page, indicates which samples correspond to the instance. Instance information includes upload time, upload location (such as city, state, and zip code), version number, and time received. The view instance page can indicate which panel this instance used in performing PCR. Further, a list of samples corresponding to this instance is presented.

A possible XML data structure for storing instance data is presented with exemplary data:

```xml
<?xml version="1.0" ?>
<epimonitor time="2005-08-01 09:09:20" zipcode ="94404" version="1">
    <sample number="1" name="Sample01" description="Sample01" zipcode="94404" />
    <sample number="2" name="Sample02" description="Sample02" zipcode="94404" />
    <sample number="3" name="Sample03" description="Sample03" zipcode="94404" />
    <sample number="4" name="Sample04" description="Sample04" zipcode="94404" />
    <sample number="5" name="Sample05" description="Sample05" zipcode="94404" />
    <sample number="6" name="Sample06" description="Sample06" zipcode="94404" />
    <sample number="7" name="Sample07" description="Sample07" zipcode="94404" />
    <sample number="8" name="Sample08" description="Sample08" zipcode="94404" />
    <panel id="1" detection_software_id="0" device_id="0">
        <probe id="2" name="B-pert" slope="-3.3547" yint="35.977" is_standard="false" />
        <probe id="3" name="L-pneu" slope="-3.1568" yint="41.495" is_standard="false" />
        <probe id="4" name="M-pneu" slope="-3.4563" yint="43.954" is_standard="false" />
        <probe id="5" name="S-pneu" slope="-3.5956" yint="43.041" is_standard="false" />
        <probe id="6" name="M-cata" slope="-3.3986" yint="43.766" is_standard="false" />
        <probe id="7" name="N-meni" slope="-3.6138" yint="45.285" is_standard="false" />
        <probe id="8" name="S-aure" slope="-3.4853" yint="45.472" is_standard="false" />
        <probe id="1" name="IPC" slope=NaN yint="NaN" is_standard="true">
            <probedata quantity="0.1" ctmean="27.603" ctstd="0.418" />
            <probedata quantity="1.0" ctmean="24.6663" ctstd="0.235" />
            <probedata quantity="10.0" ctmean="21.034" ctstd="0.184" />
        </probe>
    </panel>
    <datum samplenumber="1" probeid="2" ct="17.651617" threshold="0.2" quantity="290134.75">
        <sdsfile ct="19.225842" quantity ="NaN" task="Unknown" reporter="FAM" well_num="1" />
        <sdsfile ct="16.077393" quantity="NaN" task="Unknown" reporter="FAM" well_num="25" />
    </datum>
    <datum samplenumber="2" probeid="2" ct="22.861122" threshold="0.2" quantity="8122.7397">
        <sdsfile ct="26.811136" quantity="NaN" task="Unknown" reporter="FAM" well_num="49" />
        <sdsfile ct="18.911108" quantity="NaN" task="Unknown" reporter="FAM" well_num="73" />
    </datum>
    <datum samplenumber="3" probeid="2" ct="22.423084" threshold="0.2" quantity="10971.777">
        <sdsfile ct="NaN" quantity=" NaN" task="Unknown" reporter="FAM" well_num="97" />
        <sdsfile ct="22.423084" quantity="NaN" task="Unknown" reporter=" FAM" well_num="121" />
    </datum>
    <datum samplenumber="4" probeid="2" ct="25.692785" threshold="0.2" quantity="1163.0924">
        <sdsfile ct="NaN" quantity="NaN" task="Unknown" reporter="FAM" well_num="145" />
        <sdsfile ct="25.692785" quantity="NaN" task ="Unknown" reporter="FAM" well_num="169" />
    </datum>
    <datum samplenumber="5" probeid="2" ct="28.389887" threshold="0.2" quantity="182.65738">
        <sdsfile ct="NaN" quantity="NaN" task="Unknown" reporter="FAM" well_num="193" />
        <sdsfile ct="28.389887" quantity="NaN" task="Unknown" reporter="FAM" well_num="217" />
    </datum>
```

Clicking on one of the samples from the view instance page calls up a view sample page. The view sample page includes the number of the sample, the name and description of the sample, and the instance to which the sample corresponds. The sample data can be presented in a table, listed by probe name. The threshold, $C_T$ value, and computed copy number are presented for each probe.

This web interface can be implemented with hierarchical access rights granted to different users. A class called Administrators can create and edit panels, probes, devices, and instruments. Administrators and a lower privileged group, Viewers, can view the panel, probe, device, and instrument data, as well as the $C_T$ information collected by these devices. Data deemed proprietary, such as calibration parameters, could be hidden from various users, and entered into the EpiMonitor database directly from a private database, inaccessible even to Administrators. Instances can only be viewed, not edited, as they represent acquired data, not settings.

Figure 24:
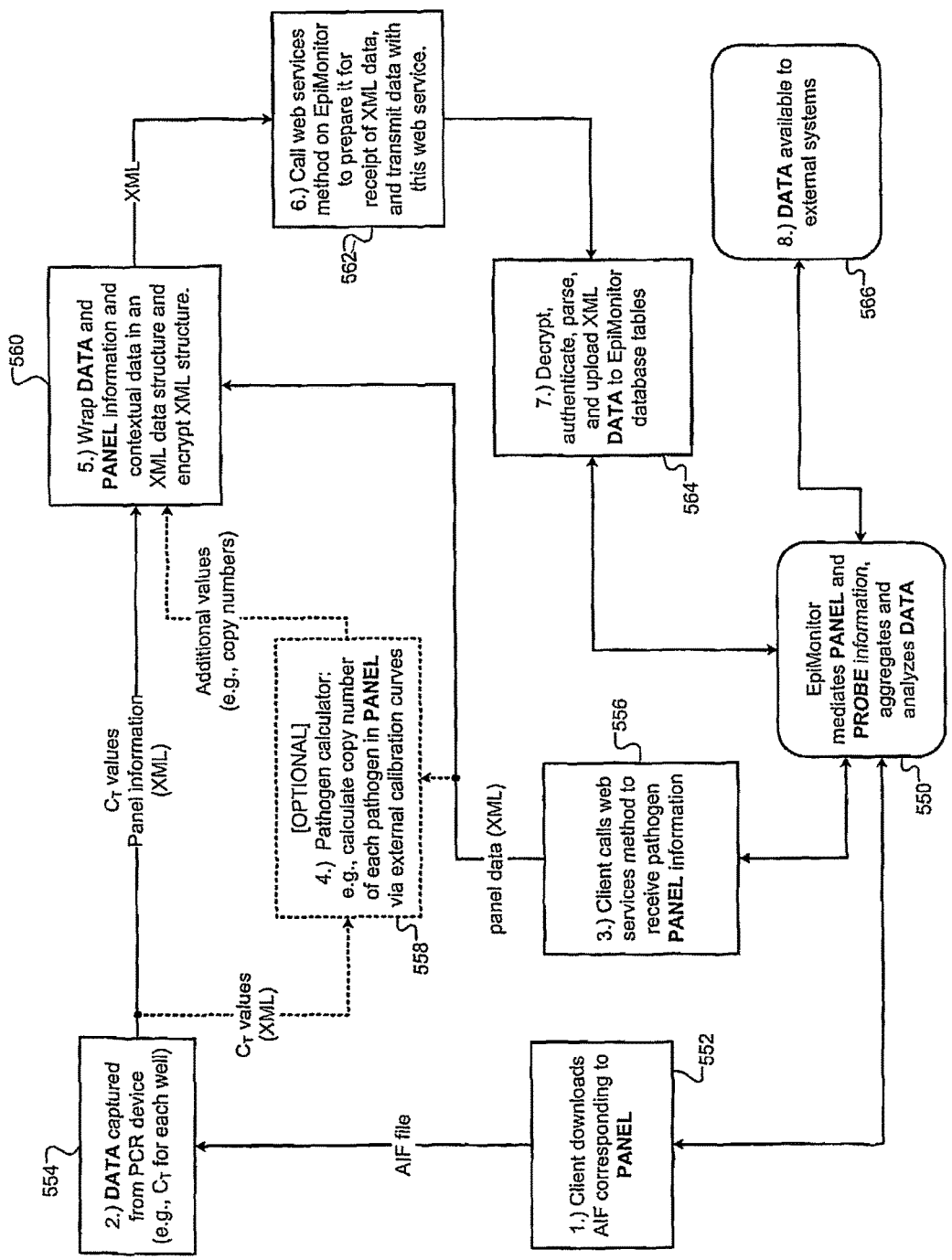
FIG. 24 is a functional flow diagram of an exemplary communication strategy between an EpiMonitor server and an EpiMonitor client.

Referring now to FIG. 24, a functional flow diagram of an exemplary communication strategy between the EpiMonitor server 550 and a reader-analyzer instrument (EpiMonitor client) 176 is presented. In step 552, the EpiMonitor client requests information from the EpiMonitor server 550 through a web services method regarding the panel to be run, and the EpiMonitor server 550 sends the corresponding information back to the client. This information identifies probe data for each well location. The information returned by the EpiMonitor server 550 can be embodied in an Assay Information File (AIF), described above. This panel information can be used in sample preparation to generate a microfluidic card 174 arranged according to the panel information.

Web services provide a standard means of interoperating between different software applications running on a variety of platforms and/or frameworks. Web services are characterized by their great interoperability and extensibility, and can be combined in a loosely coupled way in order to achieve complex operations. Programs providing simple services can interact with each other in order to deliver sophisticated services. With web services, methods on other computer systems can be invoked through a request over HTTP. The web services can be accessed in a variety of ways, including over the public Internet, Virtual Private Networks, and private networks. In addition, data can be passed through HTTP, structured as an XML In step 554, after PCR has been performed, raw data is available. In some embodiments, a cycle threshold ($C_T$) can be computed for each probe and sample combination by detection software. This data can be further processed by the EpiMonitor client. For example, if more than one $C_T$ value exists for a probe and sample combination (when there are replicates, for example), an aggregate statistic (mean, median, standard deviation, etc.) can be determined instead of reporting each $C_T$ value. In step 556, the client calls a web services method on the EpiMonitor server 550 to obtain target sequence panel data.

If implemented, the Pathogen Calculator, as described above, receives $C_T$ values in step 558. Based upon probe calibration parameters, the Pathogen Calculator can transform $C_T$ values into copy numbers. The calibration parameters can include parameters describing a linear relationship between $C_T$ value and copy number, such as a slope and an intercept. The Pathogen Calculator can also perform other analysis of target sequence presence in a sample. A flexible rules-based embodiment of qualitative analysis performed by the Pathogen Calculator is described above. This analysis can be provided to a user of the client device and/or communicated to the EpiMonitor server 550.

In step 560, PCR data (e.g., $C_T$ data, raw fluorescence or other TaqMan® data), copy number and other information computed by the Pathogen Calculator, corresponding panel information, and spatial/temporal/subject context information are integrated into an XML data structure by the EpiMonitor client. This data can be encoded and formatted according to Health Level 7 (a Standards Developing Organization accredited by the American National Standards Institute) standards. The data structure can also be encapsulated in a suitable transmission protocol, such as the Simple Object Access Protocol (SOAP).

In step 562, the client calls the web services method on the EpiMonitor server 550 that facilitates data upload, encrypts the XML data, and uploads the encrypted data. This data is logged by the EpiMonitor server 550 as an instance of the panel. In various embodiments, a manually entered zip or postal code can serve as the spatial record, and the time of execution of step 562 of the client can be recorded as the temporal component of the instance. In step 564, the XML data is decrypted, authenticated, parsed by EpiMonitor 100, and loaded into the EpiMonitor database tables. In step 566, information from the database tables is made available to external systems, such as those compliant with the PHIN (Public Health Information Network).

When transporting data, Secure Sockets Layer (SSL) can be used. In various embodiments, the encryption-decryption standard algorithm for SSL will be based on the RSA algorithm. A Public Key Infrastructure (PKI) can be used for end-user or nodal authentication. The PKI provides for third party vetting of user identities. PKI arrangements enable users to be authenticated to each other, and to use the information in identity certificates (i.e., each other's public keys) to encrypt and decrypt messages. Once authenticated, a symmetric key system can be used to transmit data in which the EpiMonitor server 550 and clients share a common encryption-decryption method outside of the public key infrastructure to provide a layer of greater security beyond authentication. In various embodiments, a certificate is issued to each end-user upon their receipt of an EpiMonitor client device.

If desired, the EpiMonitor software platform 100 can be configured to load, install, or download software to each client device. This software can share a unique encryption key with the EpiMonitor for every transaction. Resultantly, the key will differ from transaction to transaction, and from device to device. This encryption key can use the current time, in milliseconds, to encode data differently every time data is sent to the server, making it extremely difficult to intercept.

As discussed above, a hybridization array can be used to prescreen a sample to focus PCR testing upon specific bacteria, viruses, pathogens, or other target sequences. PCR testing from one instrument 176 can likewise be used in focusing the analysis of other instruments 176. A message from a client detecting a certain target sequence can be used by the EpiMonitor software platform 100 to automatically configure other clients to begin testing for this detected target sequence. Depending upon the circumstances of the detection, all units, or only selected ones, could be given instructions to begin testing for that target sequence. Thus, for example, detection of a pathogen at a local airport might cause messages to be sent to other airports that are connected by flight path with that airport. In this way, the potential spread of an epidemic can be intelligently tracked without having to alert all labs throughout the nation.

The communication capability of the EpiMonitor clients (reader-analyzer instruments 176) can be employed in paradigms other than strict client-server. Clients can communicate directly with other clients to provide input on what target sequences to be on alert for. Environmental measuring instruments, such as air sampler 60, can also be of assistance in this function. For example, if an air sampler 60 at a particular location begins measuring higher than normal concentrations of a particular substance, the air sampler 60 could communicate with other clients (reader-analyzer instruments 176) to alert their respective operators that they should begin testing for presence of a respective target sequence.

In most cases, the EpiMonitor clients provide processed cycle threshold information to the EpiMonitor server 550. If desired, however, EpiMonitor software 100 allows for raw data obtained from PCR (such as optical image or current flow information) to be transmitted. The server 550 can send a message to the client that will cause that instrument to transmit its raw data to the database system. This might be done, for example, when analytic techniques are desired that the individual instrument is not equipped to perform. Moreover, because the EpiMonitor software platform 100 can support peer-to-peer cooperation, one instrument 176 could send its raw data output to another instrument 176, allowing that other instrument 176 to perform the analysis. This might be done, for example, when a small handheld unit 56 that does not have the sophisticated processing capability of a larger laboratory instrument 52 performs the original analysis.

Figure 25:
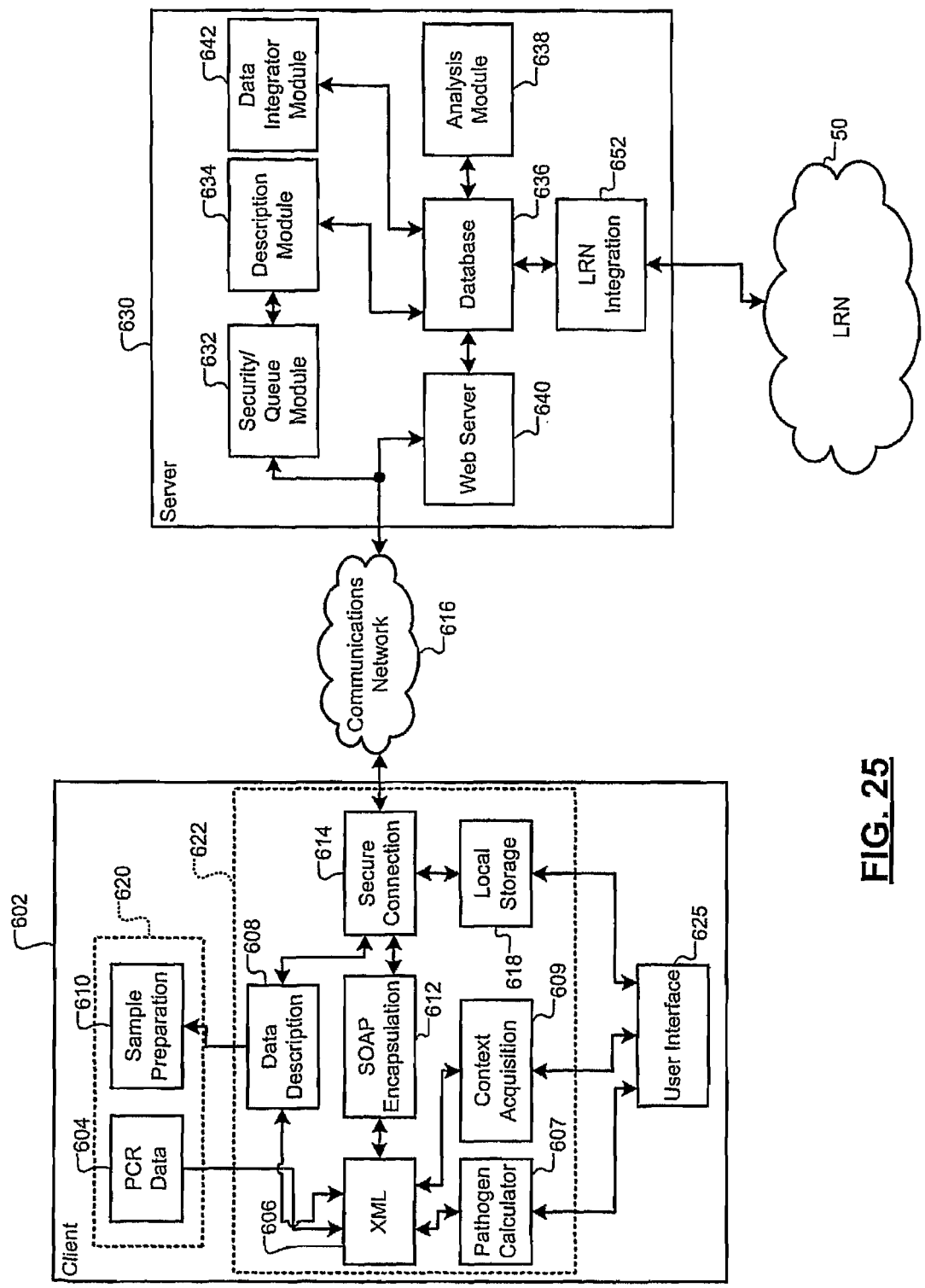
FIG. 25 is a functional block diagram of EpiMonitor client and EpiMonitor server components for a genetic surveillance and analysis system.

FIG. 25 is a functional block diagram of EpiMonitor client and server components used in aid of communication. Within a client system 602, data is acquired from PCR (such as fluorescence or current data) by a PCR data module 604. This data is transmitted to an XML processing module 606, which organizes the data according to rules from a data description module 608. The XML processing module 606 can also receive data from a pathogen calculator module 607 and a context acquisition module 609. The pathogen calculator module 607 receives PCR data from the XML module 606 (or possibly directly from the PCR data module 604), and can also receive calibration information from the XML module 606. The pathogen calculator module 607 can calibrate the PCR data, and can perform qualitative or quantitative analysis on the data before or after calibration.

The context acquisition module 609 determines contextual data (such as the spatial/temporal/climate/priority data described with respect to FIG. 25 at 462). The data description module 608 can also provide data rules to a sample preparation module 610, which is in communication with a sample assay preparation device (not shown). In this way, the data description module 608 can control which samples are prepared for which locations within the microfluidic card 174, and thus the PCR data from the microfluidic card 174 can be correctly interpreted.

Once the data has been transformed into an XML-based description, the XML module 606 forwards it to a SOAP (originally, Simple Object Access Protocol) encapsulation module 612. The SOAP encapsulation module 612 operates as a protocol for exchanging XML messages between computers, primarily via HTTP (HyperText Transfer Protocol). The SOAP message (envelope) is encrypted in an encryption module 614 for transmission over a communications network 616. The communications network 616 can be the Internet, a private network, or any other suitable network structure, whether local- or wide-area. Before or after encryption, the XML data can be stored in a local storage module 618 for later transmission or for on-board processing. The local storage module 618 can also store logs of successful transmissions.

The PCR data module 604 and sample preparation module 610 include a data gathering group 620, while the XML module 606, data description module 608, SOAP encapsulation module 612, encryption module 614, and local storage module 618 include a client-synchronizing group 622. The data gathering group 620 and client-synchronizing group 622 can be located within a single device. Alternately, the client-synchronizing group 622 can be implemented in a separate computer, which connects to the data gathering group 620 via a localized network, such as Bluetooth, Ethernet, or infrared. This configuration can be useful when the data gathering group 620 is desired to be as portable as possible, as extra processing can be off-loaded to a separate computer.

A user interface module 625 communicates with the pathogen calculator module 607, the context acquisition module 609, and the local storage module 618. The user interface module 620 can include a display, a keypad, a touchscreen, a keyboard, a mouse, and/or any other suitable forms of input and output. The user can provide the user interface module 625 with instructions for where to send acquired data, information about the samples undergoing PCR analysis, and directions for further processing. The user interface module 625 can display process control information, PCR results, and/or qualitative analysis determined by the pathogen calculator module 607.

Within a server system 630, a security/queue module 632 communicates with the communications network 616. The security/queue module 632 decrypts incoming data, validates data, and queues data for processing by a description module 634. The security/queue module 632 can also be responsible for establishing a secure connection with the secure connection module 614 of the client system 602. The description module 634 parses the received data for storage in a database 636. This parsing can include such functions as preprocessing (discussed below), natural language processing (described above), and data type conversion. Once data is stored in the database 636, an analysis module 638 can identify trends and determine if triggering conditions are present.

A web server 640 communicates with the database 636, and also with the communications network 616. If the communications network 616 is not connected to the Internet, the web server 640 can also communicate with the Internet. The web server 640 allows for remote control and viewing of the database 636 and control of the analysis module 638, as described above. The web server 640 can include data visualization and summarization responses to queries, or can provide customizable real-time streaming of data and alerts.

A data integrator module 642 communicates with the database 636. Beyond contextual data obtained from the client system 602 is contextual data that further describes the environment in which the sample was taken or that the host existed in. This information includes environmental/climate data (such as that provided by the National Oceanic and Atmospheric Administration), demographic data (such as that provided by the U.S. Census Bureau). Much of this data may be acquired from data stores distributed throughout the internet or other computer systems. Patient information, such as hospital and/or doctor records, may also exist in a digital format on a computer system.

Additionally, confirmatory data may be generated after positive results are detected via PCR. Confirmatory data includes microbiology culture tests and genetic resequencing assays/instruments. After identification of an agent via a rapid biological assay such as real-time PCR, a confirmatory test can be performed using "gold standard" procedures such as viral/microbial cultures or Applied Biosystem's MicroSeq microbial identification system.

The data integrator module 642 can incorporate this additional contextual data to help describe and analyze the PCR results collected by EpiMonitor. The data integrator module 642 locates the physical source of the additional contextual dataset, parses that information, and associates the contextual data with uploaded instance data from client systems. To facilitate operation of the data integrator module 642, an EpiMonitor interface standard can be made publicly available so that a publisher of a new data store can design their data store accordingly, or write their own private embodiment of a data integrator module so that EpiMonitor 100 can attain the new data.

While useful results are obtained by populating and analyzing the EpiMonitor database 636, integrating the database with the above-described laboratory response network (LRN), pictured diagrammatically at 50, provides additional benefit. To accomplish this integration, the LRN 50 includes a component of the EpiMonitor software platform 100, which allows the information stored in the database 636 to be made available to the LRN 50 and also to integrate with the hierarchical reporting rules defined by the LRN 50. The EpiMonitor software platform 100 includes a set of programmable business rules 652 that define how the database 636 integrates with the LRN 50. With the knowledge of the governing rule set of the LRN 50, the EpiMonitor software platform 100 integrates its database 636 into the LRN schema.

The EpiMonitor software platform 100 is designed to be highly efficient in gathering data from a diverse collection of instruments, potentially located across a widely dispersed geographic area. As the results are reported from each instrument, they are stored in the database 636 and linked with the LRN 50 according to the LRN business rules 652. In this way, if a suspected target sequence is detected in a statistically significant amount, the LRN 50 receives instant notification. The LRN 50 can then immediately forward an alert to other networks, such as a military network, and also to other systems connected through the EpiMonitor software platform 100. The response to a positive detection of statistical significance can be to send messages, possibly through the EpiMonitor software platform, to instruments at other geographic locations to begin testing for the target sequence as well.

Integration is not limited only to the LRN 50 (in its present form or future forms). Rather, the EpiMonitor software platform 100 is flexible and will allow integration of database 636 into any information system. If that information system employs predefined rules, the EpiMonitor software platform 100 can be configured to embed those rules in its business rules database 652.

A general framework for acquiring knowledge is useful as the distribution of instruments 176, data types (originating from real-time PCR, sequencing, etc.), end-users (epidemiologists, clinicians), geographical and temporal points/places of interest, target sequences, data distribution, etc. may be constantly changing. EpiMonitor 100 can provide a framework for data analysts to codify automated ways of creating knowledge most important to them and their distributions-of-interest.

Specific examples include an analyst in China who may want to "weight" "high" findings captured in Shanghai greater than those from New York. Another end-user may want to assign greater "weight" to data from assays that target a certain target sequence. To a clinician, the "co-variation" of a target sequence X with target sequence Y during the month of December may be of clinical importance. Additionally, data values produced by a more sophisticated detection instrument, such as a portable pMD, may be deemed more "sensitive" than that from a handheld pMD. Further, statistical rules can be envisioned, such as ruling data from a small-sampled population as less "important" or "critical" than data originating from a population that is more highly sampled.

The qualifiers and conclusions shown above in quotation marks are examples of assertions in the EpiMonitor knowledge framework that give qualitative, abstract meaning to the quantitative data. EpiMonitor provides a framework for codifying this knowledge and an engine to instantiate this knowledge on the aggregated data and results fed to EpiMonitor. The framework consists of an ontology to structure the ideas of the domain (where ideas such as "assays," "weights," "threshold cycle," "instrument," "environment," and "sample" are defined in a computable environment). A rules engine/interface allows users to code their assertions and knowledge about the domain using ideas in the ontology, and an inference engine applies the rules to the data to produce knowledge.

In addition, statements, rules, or sentences can be proposed by EpiMonitor software platform 100 itself after learning how users shape and codify their own rules. For example, if a user asserts a statement in the knowledge base such as "a covariation of target sequence X and Y leads to a clinical implication of Z," then EpiMonitor software platform 100 can search the space of all X and Y for other clinical implications of Z. Another example, if a user asserts that "Influenza A and Human Adenovirus vary in distribution in a co-variate manner," EpiMonitor software platform 100 could suggest rules for other pairs of target sequences that appear to co-vary together given the aggregated results.

Further examples of the operation of the knowledge framework within the EpiMonitor software platform 100 are as follows. EpiMonitor software platform 100 can use statistics to judge whether or not new data is valid. A simple illustration is that if only one data point is collected, the confidence of the measured statistic is very low; as more measurements are collected, the confidence estimate may go up, and the software can tag the outcome appropriately (such as by attaching confidences that sampled results are not false positives or false negatives). The software can be adapted to use other statistical/machine learning techniques for anomaly detection as well, including those developed by the Centers for Disease Control (CDC).

Weighting techniques can also take into account spatial and temporal information. For example, if the flu intensifies cyclically every December, for example, those findings of flu that occur in the middle of the cycle can be weighted lower than findings from other seasons because the in-season incidences are expected. Higher flu detection rates outside of the expected cycle may point to a pending outbreak. An example of spatial processing is when an event with international draw, such as a soccer tournament, is hosted in a city. The influx of people from diverse locales may cause a target sequence to be detected that is not commonly found in the city. Spatial recognition might weight this finding lower because it has a known source. The data is not discarded, however, and can be used in later analysis. Data can further be processed using quality-control metrics. Data collected across laboratories and instruments may be of different quality. For example, a sample may be PCR-inhibitory, the instrument may not be calibrated correctly, etc. A quality score reflecting these deficiencies can be used to appropriately weight or normalize data.

Further, EpiMonitor software platform 100 provides a framework to mine data such as, for example to apply probabilities and classify trends. Statistical and machine pattern recognition techniques can accept as input the current body of quantitative and qualitative results and the contextual variables collected along with it. The pattern recognition techniques then classify and assign Bayesian-type probabilities to new data given the present corpus of data. A real-life exercise involving probabilities includes gauging a result in a particular context. For example: "What is the probability of a 'positive response' given that the real-time PCR result=X and the sample collection location is 'San Francisco, Calif.,' the temperature when the sample was collected was 60 degrees, the instrument was an ABI 7900, the assay performance characteristics are X, Y, and Z, and the period of collection is December-January?"

In various embodiments, EpiMonitor software 100 can identify trends in previous outbreaks, identify trends in current data, and compare current trends with previous trends to recognize possible outbreaks. Real-life examples of data mining include using temporal analysis techniques to enable the classification of the next outbreak given the prior temporal data of outbreaks, or classifying where influenza may spread given the prior spatial distribution of an influenza epidemic. The sensitivity and specificity of predictive measures improve, as a function of data and time, as the distribution of data acquired by EpiMonitor software 100 more closely resembles the actual population. Further, as temporal and spatial data points increase, the EpiMonitor software 100 will be able to better predict yearly, seasonal, migratory, and regional trends.

Data mining analysis can also evaluate the effectiveness of countermeasures, such as travel restrictions, prescribed drugs, etc., when applied to an outbreak scenario. Much of the information regarding countermeasures can be found in the public domain: for example, travel restrictions and medication sales (such as the National Retail Data Monitor). Another source of information to make data mining more accurate and powerful can be the inclusion of syndromic data (such as chief complaints by patients, lab results, a clinician's findings) captured by syndromic surveillance systems, such as RODS (Real-time Outbreak and Disease Surveillance). For example, a positive result for the Influenza A assay in EpiMonitor software 100 can be bolstered by the patient's chief complaint of Influenza A-caused syndromes or by the population's collective syndromic trends presented by these other systems.

In various embodiments, the EpiMonitor software platform 100 supports learning rules to apply to new data. For example, a ruleset that is assigned to a particular assay X, instrument Y, or sample Z, can be labeled XYZ. The aggregated data pertaining to XYZ may have a certain distribution, such as Gaussian, with parameters such as mean and variance. In this way, algorithms that are abstract to distributions can be used, such as support vector machines. Algorithms can be specific for distributions, such as expectation-maximization, which uses a labeled data set for a particular sample as a training set to learn how to label an unlabeled set. Such algorithms may also suggest alternative labels for distributions already labeled. More simply, a maximum-likelihood approach may be taken, whereby a probability is estimated based on distributions of the existing data set. In various embodiments, neural-network type classifiers can also be implemented.

In various embodiments, the EpiMonitor software platform 100 can determine cyclical patterns of disease migration through time. Given real-time PCR qualitative data over a period of time (e.g., the number of PLUS *Bordetella pertussis* results in a given period), an outbreak can be predicted. Relevant knowledge includes how copy counts of *Bordetella pertussis* are associated with illness (i.e., did a PLUS count of *Bordetella pertussis* really cause respiratory disease X?). Seasonal effects are also helpful; for example, whether copy counts of *Bordetella pertussis* may be generally higher during the month of January. Without prior knowledge of an outbreak's distribution, time domain signal processing techniques can be used, such as discussed below. In various embodiments, the EpiMonitor software platform 100 can be populated with historic data of disease outbreaks, which may or may not include disease data.

Methodologies presented here can operate on numerical data (such as threshold cycles or gene copy numbers) and/or clinical data. In addition to time-domain processes, information can be transformed into the frequency domain using common tools such as the Fourier transform. Then, the frequency content can be filtered according to the needs of the EpiMonitor platform 100 and the data transformed back to the time domain. A selection of time domain techniques that can be employed includes CUSUM (cumulative sum), Generalized Linear Model, Exponential Weighted Moving Average, and ARIMA (Auto-Regressive Integrated Moving Average).

CUSUM, implemented in the CDC's Early Aberration Reporting System (EARS), involves the following calculation:

$$S\_t = \max\left\{0, S\_t-1 + \frac{X\_t - (\text{mean}\_t + k * s\_t)}{s\_t}\right\}.$$

S_t is the CUSUM calculation on day t, X_t is the signal on day t, mean_t and s_t are the mean and standard deviation, respectively, of the baseline signal reading (a period, possibly a week, in which no outbreak has occurred), and k is the shift from the mean to be detected.

The Generalized Linear Model, implemented in the CDC's BioSense program (as part of the Public Health Information Network) attempts to take into account day-of-week and other temporal, such as seasonal, factors. It can be calculated as follows: E(X_t)=B_0+B_1(Sunday)+ . . . +B_6 (Friday)+B_7(January)+ . . . +B_17(November)+ . . . +B_19 (Holiday)+ . . . +B_19(time trend). The expected counts on day t are defined using a generalized linear model with a particular distribution. The test statistic is the probability of observing at least X_t cases given E(X_t).

The Exponential Weighted Moving Average, implemented in the Department of Defense's ESSENCE (Electronic Surveillance System for the Early Notification of Community-based Epidemics) system, can be calculated using the equation Y_t=omega*X_t+(1−omega)*Y_t−1, where Y_1=X_1. The test statistic is (Y_t−mean_t)/(s_t* [omega/(2−omega)]^0.5). Y_t is the smoothed daily value for some smoothing parameter omega, and X_t, s_t, and mean_t are defined in the same manner as for the CUSUM method.

ARIMA (Auto-Regressive Integrated Moving Average). Auto regression is a linear regression of the current value of a series against one or more prior values of the series. A moving average can be calculated as shown above for the Exponential Weighted Moving Average. ARIMA combines both the auto regression and moving average methods, which appears to more effectively correct for seasonal effects.

In various embodiments, the EpiMonitor software platform 100 can also analyze disease through location data. Spatial domain techniques include SaTScan and WSARE (What's Strange About Recent Events). SaTScan software has been developed to analyze spatial, temporal, and space-time count data using the spatial, temporal, or space-time scan statistics. In other words, it is used to test spatial clusters of disease outbreaks to distinguish between random and statistically significant data. SaTScan relies on events being defined, which can include whether a patient carries a particular syndrome based on their PCR data being over a certain threshold for a particular target sequence. SaTScan can use a Poisson-based model, where the number of events in an area is Poisson-distributed according to a known underlying population at risk, a Bernoulli model with 0/1 event data such as cases and controls, a space-time permutation model using only case data, an ordinal model for categorical data, or an exponential model for survival time data with or without censored variables.

WSARE searches for uniqueness using a combination of values (co-variate) under a set of rules. For example, a rule could be "Gender=Male and Home Location=94404." This rule determines whether male patients whose location (postal code) is 94404 have a particularly high reading for some target sequence X. WSARE searches among possible rules and selects the most statistically significant rule for the current time period.

In various embodiments, the EpiMonitor software platform 100 can associate disease diagnoses and symptoms to multivariate PCR results. When EpiMonitor software platform 100 is first installed, prior knowledge and archival data will be limited, thus limiting the effectiveness of the learning methods that rely on a set of learning data. EpiMonitor software platform 100 can then begin associating diagnoses and symptoms to PCR results through correlation. Because EpiMonitor software platform 100 provides an infrastructure to collect this data about disease, symptoms, context, and PCR results, this correlation-type of study may be achieved.

In various embodiments, the EpiMonitor software platform 100 can be employed to determine the effects of platform and assay on copy count. Aggregating data over many permutations of assay, sample, and platform types can yield knowledge of how sensitive/specific a particular detection combination is within the context of confirmatory results or patient syndromic information. Statistically significant numbers of analyses can also be performed, creating more trustworthy normalization data. Other factors that the EpiMonitor software platform 100 can analyze include the host-susceptibility or host-resistance of populations and regions to a certain pathogen, response of a population to therapeutics, and mitigation measures. Mitigation measures can include travel restrictions, prescribed drugs, vaccines, etc.

The EpiMonitor software platform 100 can be configured into different layers. For example, if systems using the EpiMonitor software platform 100 exist for different entities, such as the CDC, the Army, Navy, private hospitals, etc., the EpiMonitor software 100 can be readily configured to add another computational layer to those already utilized by each entity. This higher layer would have the capability to utilize information from lower layers (i.e., systems deployed by the different entities) to analyze data at a higher level of abstraction for an entity such as an overseeing federal agency, the World Health Organization (WHO), etc. Because information about assays, targets, and experimental methods are stored in EpiMonitor databases, the data can be related between these distinct sources.

An example application of the EpiMonitor software platform 100 is presented merely to illustrate some of the possibilities of the software platform. In this example, the Laboratory Research Network (LRN) 50 is in communication with a military network. The military network, through methods that do not need to be disclosed to the LRN 50, may detect an increased probability that a terrorist group intends to release a pathogen into the United States at a certain port of entry. Even though the precise nature of the pathogen may not be known, certain parameters (which may be associated with efficacy or transportability) might be associated with several known viral agents. Based on this information, the LRN 50 and/or the EpiMonitor software platform 100 can determine a battery of genetic assay tests that would be most effective in detecting the pathogen, should it be introduced.

Using the EpiMonitor software platform 100, the LRN 50 communicates with reader-analyzer instruments 176 in the geographic vicinity of the targeted port of entry. The reader-analyzer instruments 176 can include displays that instruct instrument operators to begin testing using a prescribed assay panel. The assay panels can be kept in storage (such as freezers) at central distribution points and forwarded as needed. In various embodiments, a library of different assay panels may be available at the lab or a smaller library may be carried by an operator of a handheld instrument 56 or portable instrument 54. If ISAP modules 172 are provided with communication capability and able to custom-fill microfluidics cards, information to assemble suitable assays can be sent directly to the ISAP modules 172 from the EpiMonitor software platform 100. Because the EpiMonitor software platform 100 supports peer-to-peer communication, as well as communication through a central network (e.g., the Internet), the alert can propagate quickly. Peer-to-peer communication among instruments provides further assurance that all instruments receive the alert, even those that are not communicating directly with the LRN.

Once the microfluidics card 174 has been prepared and inserted into the reader-analyzer instrument 176, the reader-analyzer instruments 176 will collect data, typically by optical analysis of fluorescence signals, to determine if the target sequences are present. In a real-time PCR system, individual data collection steps can occur after each thermal cycle and these individual data sets can be analyzed to produce quantitative information about the suspected target sequence. As data is collected concerning individual samples, the LRN 50 can construct an accurate picture of where certain target sequences are occurring. This information can be fed back to the military network to improve its understanding of an emerging terrorist incident.

For example, assay panels can be developed that can test for DNA regions of interest within plants. This is useful to analyze whether DNA introduced into genetically modified organisms (GMOs) is spreading to other non-GMO crops, or even into indigenous plant species. Additionally, panels can be created that can test for DNA regions of interest within bacteria or insects. Such regions of interest can be DNA corresponding to drug or pesticide resistance. Samples can be obtained by farmers and/or agricultural workers, and can be processed on-site or submitted to a central or regional testing center. In various embodiments, PCR may be used to analyze samples. The information from each sample can be used by EpiMonitor software platform 100 to assess the spread and prevalence of sequences of interest.

In various embodiments, the present teachings can employ any of a variety of universal detection approaches involving real-time PCR and related approaches. For example, the present teachings contemplate various embodiments in which an encoding ligation reaction is performed in a first reaction vessel (such as for example, an eppendorf tube), and a plurality of decoding reactions are then performed in microfluidic card 174 described herein. For example, a multiplexed oligonucleotide ligation reaction (OLA) can be performed to query a plurality of target DNA, wherein each of the resulting reaction products is encoded with, for example, a primer portion, and/or, a universal detection portion. By including a distinct primer pair in each of a plurality of wells of microfluidic card 174 corresponding to the primers sequences encoded in the OLA, a given encoded target DNA can be amplified by that distinct primer pair in a given well of plurality of wells. Further, a universal detection probe (such as, for example, a nuclease cleavable TaqMan® probe) can be included in each of plurality of wells of microfluidic card 174 to provide for universal detection of a single universal detection probe.

Such approaches can result in a universal microfluidic card 174 with its attendant benefits including, among other things, one or more of economies of scale, manufacturing, and/or ease-of-use. The nature of the multiplexed encoding reaction can comprise any of a variety of techniques, including a multiplexed encoding PCR pre-amplification or a multiplexed encoding OLA. Further, various approaches for encoding a first sample with a first universal detection probe, and a second sample with a second universal detection probe, thereby allowing for two sample comparisons in a single microfluidic card 174, can also be performed according to the present teachings. Illustrative embodiments of such encoding and decoding methods can be found for example in PCT Publication No. WO2003U.S. Pat. No. 0,029,693 to Aydin et al., PCT Publication No. WO2003U.S. Pat. No. 0,029,967 to Andersen et al., U.S. Provisional Application Nos. 60/556,157 and 60/630,681 to Chen et al., U.S. Provisional Application No. 60/556,224 to Andersen et al., U.S. Provisional Application No. 60/556,162 to Livak et al., and U.S. Provisional Application No. 60/556,163 to Lao et al.

In various embodiments, the detection probes can be suitable for detecting single nucleotide polymorphisms (SNPs). A specific example of such detection probes comprises a set of four detection probes that are identical in sequence but for one nucleotide position. Each of the four detection probes comprises a different nucleotide (A, G, C, and T/U) at this position. The detection probes can be labeled with probe labels capable of producing different detectable signals that are distinguishable from one another, such as different fluorophores capable of emitting light at different, spectrally resolvable wavelengths (e.g., 4-differently colored fluorophores). In various embodiments, for example SNP analysis, two colors can be used for two known variants.

In various embodiments, at least one of the forward primer and the reverse primer can further comprise a detection probe. A detection probe (or its complement) can be situated within the forward primer between the first primer sequence and the sequence complementary to the target DNA, or within the reverse primer between the second primer sequence and the sequence complementary to the target DNA. A detection probe can comprise at least about 10 nucleotides up to about 70 nucleotides and, more particularly, about 15 nucleotides, about 20 nucleotides, about 30 nucleotides, about 50 nucleotides, or about 60 nucleotides. In various embodiments, a detection probe (or its complement) can further comprise a Zip-Code™ sequence (marketed by Applied Biosystems). In various embodiments, a detection probe can comprise an electrophoretic mobility modifier, such as a nucleobase polymer sequence that can increase the size of a detection probe, or in various embodiments, a non-nucleobase moiety that increases the frictional coefficient of the detection probe, such as those mobility modifier described in commonly-owned U.S. Pat. Nos. 5,470,705, 5,514,543, 5,580,732, and 5,624,800 to Grossman.

A detection probe comprising a mobility modifier can exhibit a relative mobility in an electrophoretic or chromatographic separation medium that allows a user to identify and distinguish the detection probe from other molecules comprised by the sample. In various embodiments, a detection probe comprising a sequence complementary to a detection probe and an electrophoretic mobility modifier can be, for example, a ZipChute™ detection probe (marketed by Applied Biosystems). In various embodiments, hybridization of a detection probe with an amplicon, followed by electrophoretic analysis, can be used to determine the identity and quantity of the target DNA. In various embodiments, the methods of the present teachings can include forming a detection mixture comprising a detection probe set ligation sequence, and a primer set.

In various embodiments, any detection probe set ligation sequence comprised by the detection mixture can be amplified using PCR on reader-analyzer instrument 176 and thereby form an amplification product. In various embodiments, detection of amplification of any detection probe ligation sequence of an analyte. In various embodiments, detection of amplification by reader-analyzer instrument 176 can comprise detection of binding of a detection probe to a detection probe hybridization sequence comprised by a probe set ligation sequence or an amplification product thereof. In various embodiments, detecting can comprise contacting a PCR amplification product such as an amplified probe set ligation sequence with a detection probe comprising a label under hybridizing conditions.

In various embodiments for amplification of a polynucleotide, assay can comprise a preamplification product, wherein one or more polynucleotides in an analyte have been amplified prior to being deposited in at least one of the plurality of wells. In various embodiments, these methods can further comprise forming a plurality of preamplification products by subjecting an initial analyte comprising a plurality of polynucleotides to at least one cycle of PCR to form a detection mixture comprising a plurality of preamplification products. The detection mixture of preamplification products can be then used for further amplification using microfluidic card 174 and reader-analyzer instrument 176. In various embodiments, preamplification comprises the use of isothermal methods.

In various embodiments, a two-step multiplex amplification reaction can be performed wherein the first step truncates a standard multiplex amplification round to boost a copy number of the DNA target by about 100-1000 or more fold. Following the first step, the resulting product can be divided into optimized secondary single amplification reactions, each containing one or more of the primer sets that were used previously in the first or multiplexed booster step. The booster step can occur, for example, using an aqueous target or using a solid phase archived nucleic acid. See, for example, U.S. Pat. No. 6,605,452, Marmaro.

In various embodiments, preamplification methods can employ in vitro transcription (IVT) comprising amplifying at least one sequence in a collection of nucleic acids sequences. The processes can comprise synthesizing a nucleic acid by hybridizing a primer complex to the sequence and extending the primer to form a first strand complementary to the sequence and a second strand complementary to the first strand. The primer complex can comprise a primer complementary to the sequence and a promoter region in anti-sense orientation with respect to the sequence. Copies of anti-sense RNA can be transcribed off the second strand. The promoter region, which can be single or double stranded, can be capable of inducing transcription from an operably linked DNA sequence in the presence of ribonucleotides and a RNA polymerase under suitable conditions. Suitable promoter regions may be prokaryote viruses, such as from T3 or T7 bacteriophage.

In various embodiments, the primer can be a single stranded nucleotide of sufficient length to act as a template for synthesis of extension products under suitable conditions and can be poly(T) or a collection of degenerate sequences. In various embodiments, the methods involve the incorporation of an RNA polymerase promoter into selected cDNA molecule by priming cDNA synthesis with a primer complex comprising a synthetic oligonucleotide containing the promoter. Following synthesis of double-stranded cDNA, a polymerase generally specific for the promoter can be added, and anti-sense RNA can be transcribed from the cDNA template. The progressive synthesis of multiple RNA molecules from a single cDNA template results in amplified, anti-sense RNA (aRNA) that serves as starting material for cloning procedures by using random primers. The amplification, which will typically be at least about 20-40, typically to 50 to 100 or 250-fold, but can be 500 to 1000-fold or more, can be achieved from nanogram quantities or less of cDNA.

In various embodiments, a two stage preamplification method can be used to preamplify assay in one vessel by IVT and, for example, this preamplification stage can be 100× sample. In the second stage, the preamplified product can be divided into aliquots and preamplified by PCR and, for example, this preamplification stage can be 16,000× sample or more. Although the above preamplification methods can be used in microfluidic card 174, these are only examples and are non-limiting.

In various embodiments, the preamplification can be a multiplex preamplification, wherein the analyte sample can be divided into a plurality of aliquots. Each aliquot can then be subjected to preamplification using a plurality of primer sets for DNA targets. In various embodiments, the primer sets in at least some of the plurality of aliquots differ from the primer sets in the remaining aliquots. Each resulting preamplification product detection mixture can then be dispersed into at least some of the plurality of wells of microfluidic card 174 comprising an assay having corresponding primer sets and detection probes for further amplification and detection according to the methods described herein. In various embodiments, the primer sets of assay in each of the plurality of wells can correspond to the primer sets used in making the preamplification product detection mixture. The resulting assay 1000 in each of the plurality of wells 26 thus can comprise a preamplification product and primer sets and detection probes for amplification for DNA targets, which, if present in the analyte sample, have been preamplified.

Since a plurality of different sequences can be amplified simultaneously in a single reaction, the multiplex preamplification can be used in a variety of contexts to effectively increase the concentration or quantity of a sample available for downstream analysis and/or assays. In various embodiments, because of the increased concentration or quantity of target DNA, significantly more analyses can be performed with multiplex amplified samples than can be performed with the original sample. In various embodiments, multiplex amplification further permits the ability to perform analyses that require more sample or a higher concentration of sample than was originally available. In various embodiments, multiplex amplification enables downstream analysis for assays that could not have been possible with the original sample due to its limited quantity.

In various embodiments, the plurality of aliquots can comprise 16 aliquots with each of the 16 aliquots comprising about 1536 primer sets. In various embodiments, a sample comprising a whole genome for a species, for example a human genome, can be preamplified. In various embodiments, the plurality of aliquots can be greater than 16 aliquots. In various embodiments, the number of primer sets can be greater than 1536 primer sets. In various embodiments, the plurality of aliquots can be less than 16 aliquots and the number of primer sets can be greater than 1536 primer sets. For examples of various embodiments, see PCT Publication No. WO 2004/051218 to Andersen and Ruff.

In various embodiments, assay can be preamplified, as discussed herein, in order to increase the amount of target DNA prior to distribution into a plurality of wells of a microplate. In various embodiments, assay can be collected, for example, via a needle biopsy that typically yields a small amount of sample. Distributing this sample across a large number of wells can result in variances in sample distribution that can affect the veracity of subsequent gene expression computations. In such situations, assay can be preamplified using, for example, a pooled primer set to increase the number of copies of all target DNA simultaneously.

In various embodiments, preamplification processes can be non-biased, such that all target DNA are amplified similarly and to about the same power. In various embodiments, each target DNA can be amplified reproducibly from one input sample to the next input sample. For example, if target DNA X is initially present in sample A at 100 target molecules, then after 10 cycles of PCR amplification (1000-fold), 100,000 target molecules should be present. Continuing with the example, if target DNA X is initially present in sample B at 500 target molecules, then after 10 cycles of PCR amplification (1000-fold), 500,000 target molecules should be present. In this example, the ratio of target DNA X in samples A/B remains constant before and after the amplification procedure.

In various embodiments, a minor proportion of all target DNA can have an observed preamplification efficiency of less than 100%. In various embodiments, if the amplification bias is reproducible and consistent from one input sample to another, then the ability to accurately compute comparative relative quantitation between any two samples containing different relative amounts of target can be maintained. Continuing the example from above and assuming 50% reproducible amplification efficiency, if target DNA X is initially present in sample A at 100 target molecules, then after 10 cycles of PCR amplification (50% of 1000-fold), 50,000 target molecules should be present. Further continuing the example, if target X is initially present in sample B at 500 target molecules, then after 10 cycles of PCR amplification (50% of 1000-fold), 250,000 target molecules should be present. In this example, the ratio of template X in samples A/B remains constant before and after the amplification procedure and is the same ratio as the 100% efficiency scenario.

In various embodiments, an unbiased amplification of each target DNA (x, y, z, etc.) can be determined by calculating the difference in CT value of the target DNA (x, y, z, etc.) from the $C_T$ value of a selected endogenous reference, and such calculation is referred to as the $\Delta C_T$ value for each given target DNA, as described above. In various embodiments, a reference for a bias calculation can be non-preamplified, amplified target DNA and an experimental sample can be a preamplified amplified target DNA. In various embodiments, the standard sample and experimental sample can originate from the same sample, for example, same tissue, same individual and/or same species. In various embodiments, comparison of $\Delta C_T$ values between the non-preamplified amplified target DNA and preamplified amplified target DNA can provide a measure for the bias of the preamplification process between the endogenous reference and the target DNA (x, y, z, etc.).

In various embodiments, the difference between the two $\Delta C_T$ values ($\Delta\Delta C_T$) can be zero and as such there is no bias from preamplification. This is explained in greater detail below with reference to FIG. 20. In various embodiments, the gene expression analysis system can be calibrated for potential differences in preamplification efficiency that can arise from a variety of sources, such as the effects of multiple primer sets in the same reaction. In various embodiments, calibration can be performed by computing a reference number that reflects preamplification bias. Reference number similarity for a given target DNA across different samples is indicative that the preamplification reaction $\Delta C_T$s can be used to achieve reliable gene expression computations.

In various embodiments of the present teaching, a gene expression analysis system can compute these reference numbers by collecting a sample (designated as Sample A ($S_A$)) and processing it with one or more protocols. A first protocol comprises running individual PCR gene expression reactions for each target DNA ($T_x$) relative to an endogenous reference (endo), such as, for example, 18s or GAPDH. These reactions can yield cycle threshold values for each target DNA relative to the endogenous control; as computed by:

$$\Delta C_{T\,not\,preamplified}T_xS_A = C_{T\,not\,preamplified}T_xS_A - C_{T\,not preamplified}endo$$

A second protocol can comprise running a single PCR preamplification step on assay with, for example, a pooled primer set. In various embodiments, the pooled primer set can contain primers for each target DNA. Subsequently, the preamplified product can be distributed among a plurality of wells of a microplate. PCR gene-expression reactions can be run for each preamplified target DNA ($T_x$) relative to an endogenous reference (endo). These reactions can yield cycle threshold values for each preamplified target DNA relative to the endogenous control, as computed by:

$$\Delta C_{T\,preamplified} T_x S_A = C_{T\,preamplified} T_x S_A - C_{T\,preamplified\,endo} T_x S_A$$

A difference between these $\Delta C_{T\,not\,preamplified}\,T_x S_A$ and $\Delta C_{T\,preamplified}\,T_x S_A$ can be computed by:

$$\Delta\Delta C_T T_x S_A = \Delta C_{T\,not\,preamplified} T_x S_A - \Delta C_{T\,preamplified} T_x S_A$$

In various embodiments, a value for $\Delta\Delta C_T T_x S_A$ can be zero or close to zero, which can indicate that there is no bias in the preamplification of target DNA $T_x$. In various embodiments, a negative $\Delta\Delta C_T T_x S_A$ value can indicate the preamplification process was less than 100% efficient for a given target DNA ($T_x$). For example, when using an IVT preamplification process, a percentage of target DNA with a $\Delta\Delta C_T$ of +/−1 $C_T$ of zero can be ~50%. In another example, when using a multiplex preamplification process, a percentage of target DNA with a $\Delta\Delta CT$ of +/−1 $C_T$ of zero can be ~90%.

In various embodiments, amplification efficiency can be less than 100% for a particular target DNA, therefore $\Delta\Delta C_T$ is less than zero for the particular target DNA. An example can be an evaluation of $\Delta\Delta C_T$ values for a group of target DNA from a 1536-plex for the multiplex preamplification process including four different human sample input sources: liver, lung, brain and an universal reference tissue composite. In this example, most $\Delta\Delta C_T$ values are near zero, however, some of the target DNA have a negative $\Delta\Delta C_T$ value but these negative values are reproducible from one sample input source to another. In various embodiments, a gene expression analysis system can determine if a bias exists for target DNA analyzed for different sample inputs. Other apparatus, compositions, and methods that may be useful herein can be found in commonly assigned U.S. patent application Ser. No. 11/086,261.

Some embodiments and the examples described herein are exemplary and not intended to be limiting in describing the full scope of compositions and methods of these teachings. Equivalent changes, modifications, and variations of some embodiments, materials, compositions, and methods can be made within the scope of the present teachings, with substantially similar results.

What is claimed is:

1. A method of performing genetic surveillance, comprising:
   performing genetic assay analysis of a sample obtained from an individual member of a population using a reader-analyzer instrument, said reader-analyzer instrument comprising an integrated sample and assay preparation apparatus configured to capture said sample, suspend said sample in solution, and process said sample;
   generating sample genetic data based on said genetic assay analysis using said reader-analyzer instrument, said reader-analyzer configured to capture said sample genetic data using optical analysis of fluorescent signals;
   capturing contextual information associated with said sample using said reader-analyzer instrument, said contextual information comprising spatial information and temporal information;
   communicating said spatial information and temporal information associated with said genetic sample data over a network using said reader-analyzer instrument to effect said communication; and
   communicating targeting instructions over a network to said reader-analyzer instrument, said targeting instructions identifying at least one of a bacteria, virus, pathogen, and target sequence for targeting by the reader-analyzer instrument.

2. The method of claim 1 further comprising communicating said spatial information and temporal information associated with said sample genetic data to a laboratory response network.

3. The method of claim 1 further comprising using at least one portable reader-analyzer instrument to perform genetic assay analysis of said sample.

4. The method of claim 1 further comprising communicating said spatial information and temporal information associated with said sample genetic data from a first reader-analyzer instrument to a second reader-analyzer instrument.

5. The method of claim 1, further comprising performing sample preparation steps on said sample based on information received over said network, said sample preparation steps including manipulation of at least one assay.

6. The method of claim 1 and wherein said manipulation is performed based on information received over said network.

7. The method of claim 1 wherein comprising generating said sample data comprises collecting data that identifies a presence or an absence of at least one pathogenic organism.

8. The method of claim 7 wherein said collecting data step is performed by analyzing at least one target sequence related to the at least one pathogenic organism.

9. The method of claim 1 further comprising collecting demographic information from said individual member of a population.

10. The method of claim 9 wherein said demographic information is associated with said spatial information, said temporal information and said sample genetic data.

11. The method of claim 1 wherein said reader-analyzer instrument is associated with an automatic sensing device and the sample obtaining step is performed automatically by said automatic sensing device.

12. The method of claim 1 wherein said sample obtaining step is performed by the user of said reader-analyzer instrument.

13. The method of claim 1, wherein the integrated sample and assay preparation module is a microfluidics card.

14. The method of claim 13, wherein the microfluidics card comprises of a reaction chamber and a sample inlet port.

15. The method of claim 13, wherein the microfluidics card is configured to provide for detection of a detection probe.

16. The method of claim 15, wherein the detection probe is suitable for detecting single nucleotide polymorphisms.

17. The method of claim 1, wherein the reader-analyzer instrument is configured to retrieve said spatial information based on at least one of a global positioning device or a geographic lookup table using an internet protocol address.

* * * * *